United States Patent
Alli et al.

(10) Patent No.: US 11,958,923 B2
(45) Date of Patent: *Apr. 16, 2024

(54) COMPOSITIONS WITH HIGH REFRACTIVE INDEX AND ABBE NUMBER

(71) Applicant: Johnson & Johnson Surgical Vision, Inc., Irvine, CA (US)

(72) Inventors: Azaam Alli, Jacksonville, FL (US); Bart Johnson, Laguna Beach, CA (US); Scott L. Joslin, Ponte Vedra Beach, FL (US); Ghulam Maharvi, Jacksonville, FL (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/190,018

(22) Filed: Mar. 24, 2023

(65) Prior Publication Data

US 2023/0265230 A1  Aug. 24, 2023

Related U.S. Application Data

(63) Continuation of application No. 16/865,055, filed on May 1, 2020, now Pat. No. 11,667,742.

(60) Provisional application No. 62/843,054, filed on May 3, 2019.

(51) Int. Cl.
   *C08F 220/40* (2006.01)
   *G02B 1/04* (2006.01)

(52) U.S. Cl.
   CPC ............ *C08F 220/40* (2013.01); *G02B 1/041* (2013.01)

(58) Field of Classification Search
   CPC ...................................... G02B 1/041
   See application file for complete search history.

(56) References Cited

U.S. PATENT DOCUMENTS

| | | |
|---|---|---|
| 4,131,729 A | 12/1978 | Schmitt et al. |
| 4,573,998 A | 3/1986 | Mazzocco |
| 4,731,079 A | 3/1988 | Stoy |
| 5,233,007 A | 8/1993 | Yang |
| 5,290,892 A | 3/1994 | Namdaran et al. |
| 5,357,024 A | 10/1994 | Leclaire |
| 5,403,901 A | 4/1995 | Namdaran et al. |
| 5,424,339 A | 6/1995 | Zanka et al. |
| 5,433,746 A | 7/1995 | Namdaran et al. |
| 5,541,278 A | 7/1996 | Raleigh et al. |
| 5,648,402 A | 7/1997 | Nunez et al. |
| 5,674,960 A | 10/1997 | Namdaran et al. |
| 5,693,095 A | 12/1997 | Freeman et al. |
| 5,694,195 A | 12/1997 | Engardio et al. |
| 5,861,031 A | 1/1999 | Namdaran et al. |
| 5,910,537 A | 6/1999 | Feingold et al. |
| 5,913,898 A | 6/1999 | Feingold |
| 6,140,438 A | 10/2000 | Ojio et al. |
| 6,313,187 B2 | 11/2001 | LeBoeuf et al. |
| 6,313,251 B1 | 11/2001 | Toh et al. |
| 6,353,069 B1 | 3/2002 | Freeman et al. |
| 6,367,929 B1 | 4/2002 | Maiden et al. |
| 6,416,550 B2 | 7/2002 | Freeman |
| 6,491,721 B2 | 12/2002 | Freeman et al. |
| 6,699,953 B2 | 3/2004 | Oshikiri et al. |
| 6,770,735 B2 | 8/2004 | Tanaka et al. |
| 6,852,793 B2 | 2/2005 | Salamone et al. |
| 7,009,024 B2 | 3/2006 | Salamone et al. |
| 7,169,874 B2 | 1/2007 | Salamone et al. |
| 7,217,778 B2 | 5/2007 | Verbruggen |
| 7,279,538 B2 | 10/2007 | Lai et al. |
| 7,295,749 B2 | 11/2007 | Kitamura et al. |
| 7,297,160 B2 | 11/2007 | Salamone et al. |
| 7,301,705 B2 | 11/2007 | Yoshimura et al. |
| 7,423,108 B2 | 9/2008 | Kunzler et al. |
| 7,632,904 B2 | 12/2009 | Salamone et al. |
| 7,714,090 B2 | 5/2010 | Wamoto et al. |
| 7,763,682 B2 | 7/2010 | Lowery et al. |
| 7,767,779 B2 | 8/2010 | Jallouli et al. |
| 7,928,171 B2 | 4/2011 | Makker et al. |
| 8,148,445 B1 | 4/2012 | Laredo |
| 8,293,858 B1 | 10/2012 | Laredo |
| 8,323,799 B2 | 12/2012 | Hu et al. |
| 8,329,763 B2 | 12/2012 | Werner |
| 8,449,610 B2 | 5/2013 | Laredo et al. |
| 8,470,948 B2 | 6/2013 | Stiegman |
| 8,681,428 B1 | 3/2014 | Brown |
| 8,759,414 B2 | 6/2014 | Muller-Lierheim et al. |
| 9,012,566 B2 | 4/2015 | Buhler et al. |
| 9,289,531 B2 | 3/2016 | Jiang et al. |
| 9,427,493 B2 | 8/2016 | Kahook et al. |
| 9,475,967 B2 | 10/2016 | Lipscomb et al. |

(Continued)

FOREIGN PATENT DOCUMENTS

| | | |
|---|---|---|
| AU | 734097 B2 | 6/2001 |
| CA | 2059328 A1 | 10/1992 |
| CA | 2752046 A1 | 8/2010 |
| CA | 2802793 A1 | 2/2012 |
| CN | 102822217 A | 12/2012 |
| CN | 102140149 B | 3/2013 |
| CN | 109337591 A | 2/2019 |
| CN | 105985749 B | 6/2019 |
| CN | 105985750 B | 6/2019 |
| CN | 106459316 B | 3/2020 |
| CN | 111512227 A | 8/2020 |
| CN | 107429129 B | 9/2020 |
| CN | 109438614 B | 1/2021 |
| DE | 4010784 C2 | 11/1994 |
| EP | 1003795 B1 | 2/2004 |
| EP | 2906970 B1 | 11/2016 |
| EP | 3627212 A1 | 3/2020 |

(Continued)

*Primary Examiner* — Michael F Pepitone
(74) *Attorney, Agent, or Firm* — Johnson & Johnson Surgical Vision, Inc.

(57) ABSTRACT

Disclosed are co-polymers which are produced from reactive monomer mixtures and which have both high refractive index and a high Abbe number. These materials are well suited for use as implantable ophthalmic devices and have a refractive index which may be edited through application of energy. When used for an intraocular lens, the high refractive index allows for a thin lens which compresses to allow a small incision size.

25 Claims, 11 Drawing Sheets

(56) References Cited

U.S. PATENT DOCUMENTS

| | | |
|---|---|---|
| 9,622,853 B2 | 4/2017 | Argal |
| 9,820,850 B2 | 11/2017 | Mentak |
| 9,864,102 B2 | 1/2018 | Laredo et al. |
| 9,921,341 B2 | 3/2018 | Laredo et al. |
| 10,053,249 B2 | 8/2018 | Stutz et al. |
| 10,117,965 B1 | 11/2018 | Suganuma et al. |
| 10,155,349 B2 | 12/2018 | Pruitt et al. |
| 10,408,947 B2 | 9/2019 | Beacham et al. |
| 10,408,974 B2 | 9/2019 | Schlueter |
| 10,626,206 B2 | 4/2020 | Terrisse |
| 10,722,612 B2 | 7/2020 | Jiang et al. |
| 11,667,742 B2 * | 6/2023 | Alli .................. G02B 1/041 523/106 |
| 2002/0049290 A1 | 4/2002 | Vanderbilt |
| 2004/0248038 A1 | 12/2004 | Yokoyama et al. |
| 2005/0254003 A1 | 11/2005 | Jani et al. |
| 2007/0004863 A1 | 1/2007 | Mentak |
| 2007/0222095 A1 | 9/2007 | Zanini et al. |
| 2007/0249794 A1 | 10/2007 | Evans et al. |
| 2008/0200582 A1 | 8/2008 | Craciun et al. |
| 2011/0177256 A1 | 7/2011 | McAneney et al. |
| 2012/0202916 A1 | 8/2012 | Laredo et al. |
| 2012/0309919 A1 | 12/2012 | Laredo |
| 2013/0253159 A1 | 9/2013 | Benz et al. |
| 2013/0345364 A1 | 12/2013 | Alli et al. |
| 2014/0163130 A1 | 6/2014 | Zhang et al. |
| 2015/0299500 A1 | 10/2015 | Haraguchi et al. |
| 2015/0321991 A1 | 11/2015 | Ponrathnam et al. |
| 2016/0235886 A1 | 8/2016 | Jiang et al. |
| 2017/0072601 A1 | 3/2017 | Akasaki |
| 2018/0009922 A1 | 1/2018 | Alli et al. |
| 2018/0011222 A1 | 1/2018 | Alli et al. |
| 2018/0011223 A1 | 1/2018 | Alli et al. |
| 2018/0319901 A1 | 11/2018 | Hampson et al. |
| 2019/0000364 A1 | 1/2019 | Balaconis et al. |
| 2019/0225726 A1 | 7/2019 | DeSousa et al. |
| 2019/0314547 A1 | 10/2019 | Sui et al. |
| 2019/0338092 A1 | 11/2019 | Reit et al. |
| 2019/0339419 A1 | 11/2019 | Schlueter |
| 2020/0038548 A1 | 2/2020 | Suganuma et al. |
| 2020/0038549 A1 | 2/2020 | Stoy et al. |
| 2020/0123410 A1 | 4/2020 | Reit et al. |
| 2020/0165411 A1 | 5/2020 | Takagi et al. |
| 2020/0255709 A1 | 8/2020 | Reit et al. |
| 2020/0347166 A1 | 11/2020 | Alli et al. |
| 2020/0347167 A1 | 11/2020 | Alli et al. |
| 2022/0135720 A1 | 5/2022 | Alli et al. |

FOREIGN PATENT DOCUMENTS

| | | |
|---|---|---|
| FR | 2774998 A1 | 8/1999 |
| JP | H05202346 A | 8/1993 |
| JP | H0726193 A | 1/1995 |
| JP | 2004075879 A | 3/2004 |
| JP | 2006328094 A | 12/2006 |
| JP | 2007016141 A | 1/2007 |
| JP | 2007077215 A | 3/2007 |
| JP | 2007091921 A | 4/2007 |
| JP | 2007169560 A | 7/2007 |
| JP | 2007186630 A | 7/2007 |
| JP | 2007262175 A | 10/2007 |
| JP | 2009227778 A | 10/2009 |
| JP | 2009256275 A | 11/2009 |
| JP | 2009256662 A | 11/2009 |
| JP | 2011038050 A | 2/2011 |
| JP | 2012052098 A | 3/2012 |
| JP | 2012082386 A | 4/2012 |
| JP | 2013010842 A | 1/2013 |
| JP | 2013234127 A | 11/2013 |
| KR | 20080023016 A | 3/2008 |
| KR | 20110109938 A | 10/2011 |
| WO | 9727223 A1 | 7/1997 |
| WO | 0011097 A1 | 3/2000 |
| WO | 0064956 A1 | 11/2000 |
| WO | 2006043409 A1 | 4/2006 |
| WO | 2011125956 A1 | 10/2011 |
| WO | 2012004744 A2 | 1/2012 |
| WO | 2012167124 A1 | 12/2012 |
| WO | 2013048993 A1 | 4/2013 |
| WO | 2015016363 A1 | 2/2015 |
| WO | 2015068839 A1 | 5/2015 |
| WO | 2015132605 A1 | 9/2015 |
| WO | 2015170278 A1 | 11/2015 |
| WO | 2017072186 A1 | 5/2017 |
| WO | 2018212063 A1 | 11/2018 |
| WO | 2018229653 A1 | 12/2018 |

* cited by examiner

Comparative Example 2

Comparative Example 1

Example 35

Example 70

Example 66

COMPOSITIONS WITH HIGH REFRACTIVE INDEX AND ABBE NUMBER

CROSS-REFERENCE TO RELATED APPLICATIONS

This application is a continuation of U.S. patent application Ser. No. 16/865,055, filed May 1, 2020, now U.S. Pat. No. 11,667,742, issued on Jun. 6, 2023, which claims priority to U.S. Provisional Patent Application No. 62/843,054, filed on May 3, 2019, the entire contents of which are hereby incorporated by reference.

FIELD OF THE DISCLOSURE

This disclosure is directed to co-polymers produced from reactive monomer mixtures which, when polymerized, form acrylic materials having high refractive indexes and high Abbe numbers. These materials, which may have an editable refractive index, are designed for use in ophthalmic devices, such as intraocular implants or lenses.

BACKGROUND OF THE DISCLOSURE

Cataract surgery is commonly performed to replace the natural eye lens that has become opaque. Materials that are used to replace the natural crystalline lens must be soft and have excellent flexibility so that, once formed into a lens, they may be folded and passed through an incision which is typically about 2 mm. Furthermore, the material must have excellent transparency and little to no glistening. Having a high refractive index allows for a thinner lens to be used. A material with a high Abbe number demonstrates less dispersion. This, in turn, allows for improved optical results and less light scattering. Combining a high refractive index with a high Abbe number provides preferable optical characteristics for a material.

One of the first patents in this area, U.S. Pat. No. 4,573,998, to Mazzocco, discloses a deformable intraocular lens that can be rolled to fit through a relatively small incision. The deformable lens is inserted into the eye while it is held in its rolled configuration, then released inside the chamber of the eye. The elastic properties of the lens cause it to resume its molded shape after insertion into the eye. Mazzocco discloses polyurethane elastomers, silicone elastomers, hydrogel polymer compounds, organic or synthetic gel compounds and combinations thereof as suitable materials for the deformable lens.

Friction from inside the delivery device and physician force during delivery can damage the lens. To overcome this issue, some delivery devices are coated to provide extra lubricity. For example, U.S. Pat. No. 8,323,799, to Hu, discloses a soft, flexible highly lubricious coatings for polymeric IOL insertion cartridges that allow IOLs to be easily inserted through small bore cartridges suitable for use with small (less than 3 mm) incisions. While such coatings are helpful, there is a need to further reduce friction forces imposed on the lens during insertion.

Accordingly, there is a need for a material, with a relatively high refractive index and Abbe number, which can be used to form a flexible intraocular lens which can be simply rolled or folded into a configuration which will fit through a small incision. There is further need for such a material to have internal lubricity.

SUMMARY OF THE DISCLOSURE

In certain embodiments, the present disclosure relates a composition made by free radical polymerization of a reactive monomer mixture comprising:

(A) (i) at least one cycloaliphatic (meth)acrylate; (ii) at least one aromatic (meth)acrylate; (iii) at least one aliphatic (meth)acrylate; and (iv) at least one cross-linking agent; wherein the composition exhibits a refractive index of at least 1.45 and an Abbe number of at least 39 ("Composition (A)"); or (B) (i) at least one cycloaliphatic (meth)acrylate; (ii) at least one aliphatic (meth)acrylate; and (iii) at least one cross-linking agent; wherein the composition exhibits a refractive index of at least 1.45 and an Abbe number of at least 39 ("Composition (B)");

(C) (i) at least one hydrophobic monomer; (ii) at least one acrylate monomer of the following formula (I):

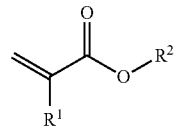

wherein $R^1$ is selected from hydrogen and methyl, and wherein $R^2$ is a non-aromatic moiety having at least one carbon-carbon double bond; and (iii) at least one cross-linking agent ("Composition (C)");

(D) (i) at least one cycloaliphatic (meth)acrylate monomer containing more than one cycloaliphatic ring; (ii) at least one monomer selected from hydrophilic monomers and hydroxyalkyl (meth)acrylate monomers, and any combinations thereof; and (iii) at least one cross-linking agent; wherein the composition exhibits a refractive index of at least 1.45 and an Abbe number of at least 39 ("Composition (D)"); or (E) (i) at least one hydrophobic monomer; (ii) at least one monomer selected from hydrophilic monomers and hydroxyalkyl (meth)acrylate monomers, and any combinations thereof; and (iii) a tricyclo[5.2.1.0$^{2,6}$]decanedimethanol di(meth)acrylate cross-linking agent; wherein the composition exhibits a refractive index of at least 1.45 and an Abbe number of at least 39 ("Composition (E)").

In certain embodiments, the present disclosure provides a device comprising Composition (A), Composition (B), Composition (C), Composition (D), or Composition (E). In certain other embodiments, the device is an ophthalmic device. In particular embodiments, the ophthalmic device comprises a lens, inlay, outlay, or insert selected from an intraocular implant or lens, a contact lens, a corneal inlay, a corneal outlay, and a corneal insert. In specific embodiments, the ophthalmic device is an intraocular implant or lens. More specifically, the present disclosure also provides intraocular implants and/or lenses made at least partially or completely from Composition (A), Composition (B), Composition (C), Composition (D), or Composition (E).

In still yet other embodiments, the present disclosure provides a method for making an ophthalmic device, the method comprising the steps of: (a) providing any one of Composition (A), Composition (B), Composition (C), Composition (D), or Composition (E); and (b) forming an ophthalmic device from any of said compositions. In other embodiments, the presently disclosed subject matter provides a method for making an ophthalmic device, the method comprising: (a) preparing a blank from any one of Composition (A), Composition (B), Composition (C), Composition (D), or Composition (E); and (b) machining an ophthalmic device from the blank. In other embodiments, the presently disclosed subject matter provides a method for making an ophthalmic device, the method comprising molding an ophthalmic device from any one of Composition (A), Composition (B), Composition (C), Composition (D), or Composition (E).

In still other embodiments, the presently disclosed subject matter provides a method for making an ophthalmic device, the method comprising (a) molding an ophthalmic device from any one of Composition (A), Composition (B), Composition (C), Composition (D), or Composition (E), and (b) refining the molded lens surface via machining.

In certain embodiments of either method, the method further comprises the step of extracting the ophthalmic device with a solvent. In certain embodiments, the method further comprises the step of hydrating the extracted ophthalmic device with at least one aqueous solution. In particular embodiments, the method further comprises an irradiation step using a laser. In more particular embodiments, the method further comprises a step of sterilizing the ophthalmic device.

DETAILED DESCRIPTION OF THE DISCLOSURE

Figure 1:
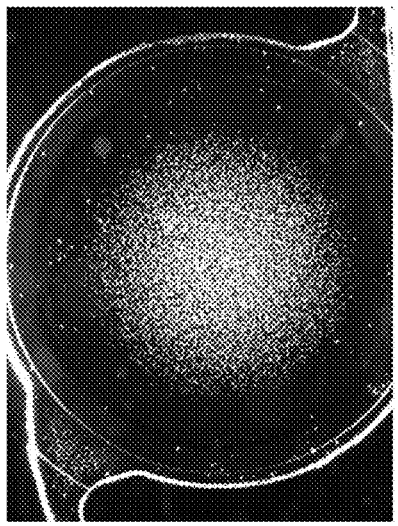
FIG. 1 shows the levels of micro-glistening by dark field microscopy.
Figure 1:
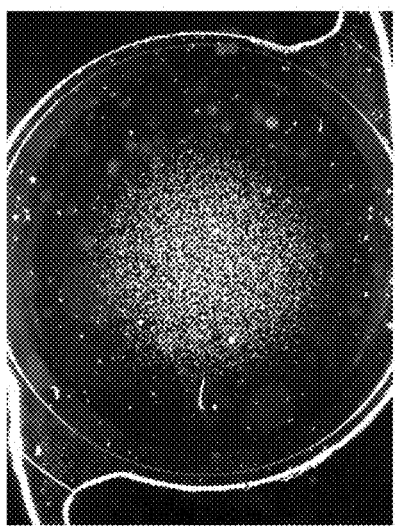
Figure 1:
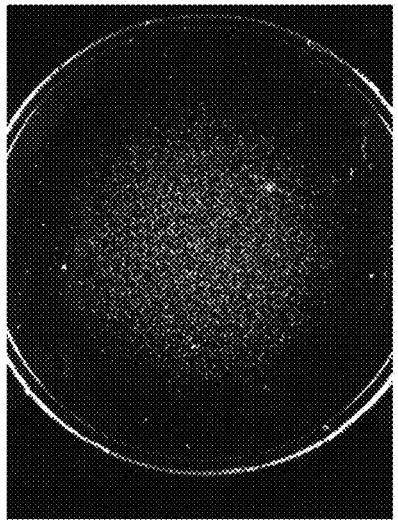

It is to be understood that the disclosure is not limited to the details of construction or process steps set forth in the following description. The disclosure is capable of other embodiments and of being practiced or being carried out in various ways using the teaching herein.

A. Definitions

With respect to the terms used in this disclosure, the following definitions are provided.

Unless defined otherwise, all technical and scientific terms used herein have the same meaning as commonly understood by one of ordinary skill in the art to which the disclosure belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

The term "reactive monomer mixture" refers to a mixture of components (both reactive and non-reactive) which are mixed together and when subjected to polymerization conditions, form the presently disclosed compositions and ophthalmic devices. The reactive mixture may include reactive components such as monomers, macromers, prepolymers, cross-linkers, initiators, diluents, and additional components, including, but not limited to, wetting agents, release agents, dyes, light absorbing compounds, such as ultraviolet-high energy visible light (UV/HEV) absorbers, pigments, dyes and photochromic compounds, any of which may be reactive or non-reactive but are capable of being retained within the resulting biomedical device, e.g., an ophthalmic device, as well as active components, including pharmaceutical and nutraceutical compounds, and any diluents. It will be appreciated that a wide range of additives may be added based upon the biomedical device which is made, and its intended use. In some embodiments, concentrations of components of the reactive mixture are given in weight % of all components in the reaction mixture, excluding diluent. When diluents are used their concentrations are given as weight % based upon the amount of all components in the reaction mixture and the diluent.

"Reactive components" are the components in the reactive monomer mixture which become part of the structure of the polymeric network of the resulting composition, by covalent bonding or hydrogen bonding. Diluents and processing aids which do not become part of the structure of the polymer are not reactive components.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula [***]$_n$, is used to depict the number of repeating units in a polymer's chemical formula, the formula should be interpreted to represent the number average molecular weight of the macromolecule.

The term "individual" includes humans and non-human vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular implants, intraocular lenses, and contact lenses. The biomedical devices may be ophthalmic devices, particularly ophthalmic implants or ophthalmic lenses made from the reactive monomer compositions described herein.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise an intraocular implant, intraocular lens, or contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet (UV) light absorbing, visible (VIS) light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

"Intraocular lens" refers to a lens implanted in an eye. In some embodiments, the intraocular lens is implanted in the eye to replace an existing crystalline lens (such as, for example, because the existing lens has been clouded over by a cataract, or as a form of refractive surgery to change the eye's optical power).

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or ionic polymerization (e.g., cationic polymerization), for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyllactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500 Daltons and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and cross-linkers may be used interchangeably.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer. The terms "reactive mixture" and "reactive monomer mixture" refer to the mixture of components (both retained and non-retained) which are mixed together and, when subjected to polymerization conditions, result in formation of a polymeric network as well as biomedical devices, ophthalmic devices, intraocular implants, contact lenses, and intraocular lenses made therefrom. The reactive mixture may comprise retained components such as monomers, macromers, prepolymers, cross-linkers, and initiators, additives such as wetting agents, polymers, dyes, light absorbing compounds such as UV/HEV absorbers, pigments, photochromic compounds, pharmaceutical compounds, and/or nutraceutical compounds, any of which may be reactive or non-reactive but are capable of being retained within the resulting biomedical device. The reactive mixture may also contain non-retained components which are intended to be removed from the device prior to its use, such as diluents. It will be appreciated that a wide range of additives may be added based upon the biomedical device which is made and its intended use. Concentrations of components of the reactive mixture are expressed as weight percentages of all retained components in the reactive mixture, therefore excluding non-retained components such as diluent. When diluents are used, their concentrations are expressed as weight percentages based upon the amount of all components in the reactive mixture (including the diluent).

"Retained components" are the polymerizable compounds (such as monomers, macromers, oligomers, prepolymers, and cross-linkers) in the reactive mixture, as well as any other components in the reactive mixture which are intended to substantially remain in the polymeric network after polymerization and all work-up steps (such as extraction steps) and packaging steps have been completed. Retained components may be retained in the polymeric network by covalent bonding, hydrogen bonding, electrostatic interactions, the formation of interpenetrating polymeric networks, or any other means. Components that are intended to release from the biomedical device once it is in use are still considered "retained components." For example, pharmaceutical or nutraceutical components in a contact lens which are intended to be released during wear are considered "retained components." Components that are intended to be removed from the polymeric network during the manufacturing process (e.g., by extraction), such as diluents, are "non-retained components."

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" or "aliphatic" are used interchangeably herein and refer to an optionally substituted linear or branched alkyl group containing the indicated number of carbon atoms. If no number is indicated, then alkyl (including any optional substituents on alkyl) may contain any of 1 to 16 carbon atoms, including 1, 2, 3, 4, 5, 6, 7, 8, 9, 10, 11, 12, 13, 14, 15, and 16 carbon atoms. Preferably, the alkyl group contains 1 to 10 carbon atoms, including 1, 2, 3, 4, 5, 6, 7, 8, 9, and 10 carbon atoms, alternatively 1 to 8 carbon atoms, including 1, 2, 3, 4, 5, 6, 7, and 8 carbon atoms, alternatively 1 to 6 carbon atoms, including 1, 2, 3, and 4 carbon atoms, or alternatively 1 to 4 carbon atoms, including 1, 2, 3, and 4. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as $—CH_2—$, $—CH_2CH_2—$, $—CH_2CH_2CH_2—$, $—CH_2CH(CH_3)CH_2—$, and $—CH_2CH_2CH_2CH_2—$.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as $—CF_3—$ or $—CF_2CF_3—$. "Haloalkylene" means a divalent haloalkyl group, such as $—CH_2CF_2—$.

"Hydroxy" refers to an —OH group.

"Hydroxyalkyl" refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

"Cycloalkyl" or "cycloaliphatic" are used interchangeably herein and refer to an optionally substituted cyclic hydrocarbon containing the indicated number of ring carbon atoms. If no number is indicated, then cycloalkyl may contain 3 to 20 ring carbon atoms (e.g., 3 to 12 ring carbon atoms). Cycloaliphatic groups can be monocyclic, bicyclic, tricyclic, bridged, fused, and/or spirocyclic. Cycloaliphatic groups can also have one or more double bonds, provided that the group is not fully aromatic. Preferred monocyclic cycloaliphatic groups are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Arylalkyl" refers to an aryl group, as defined herein, appended to the parent molecular moiety through an alkyl group, as defined herein. Representative examples of arylalkyl include phenylmethyl (i.e. benzyl), phenylethyl, and phenylpropyl.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Arylthio" refers to an aryl group attached to a parent molecular moiety through a sulfur bridge. Examples include phenylthiol. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —CH$_2$CH$_2$NH—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected R$^A$ groups (where R$^A$ is as defined in formula A options (b)-(i)) to complete their valence.

Formula A. The silicone-containing component may comprise one or more polymerizable compounds of Formula A

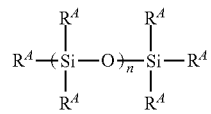

Formula A wherein:
at least one R$^A$ is a group of formula R$_g$-L- wherein R$_g$ is a polymerizable group and L is a linking group, and the remaining R$^A$ are each independently:
a. R$_g$-L-,
b. C$_1$-C$_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
c. C$_3$-C$_{12}$ cycloalkyl optionally substituted with one or more alkyl, hydroxy, amino, amido, oxa, carbonyl, alkoxy, amido, carbamate, carbonate, halo, phenyl, benzyl, or combinations thereof,
d. a C$_6$-C$_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
e. halo,
f. alkoxy, cyclic alkoxy, or aryloxy,
g. siloxy,
h. alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or
a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and
n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different R$^A$ substituents and if different R$^A$ substituents are present, the n groups may be in random or block configuration.

In Formula A, three R$^A$ may each comprise a polymerizable group, alternatively two R$^A$ may each comprise a polymerizable group, or alternatively one R$^A$ may comprise a polymerizable group.

"Silyl" refers to a structure of formula R$_3$Si— and "siloxy" refers to a structure of formula R$_3$Si—O—, where each R in silyl or siloxy is independently selected from trimethylsiloxy, C$_1$-C$_8$ alkyl (preferably C$_1$-C$_3$ alkyl, more preferably ethyl or methyl), and C$_3$-C$_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[CH$_2$CH$_2$O]$_p$— or CH$_3$O—

[CH$_2$CH$_2$O]$_p$—). Examples of alkyleneoxy include polyethyleneoxy, polypropyleneoxy, polybutyleneoxy, and poly(ethyleneoxy-co-propyleneoxy).

"Oxaalkylene" refers to an alkylene group as defined above where one or more non-adjacent CH$_2$ groups have been substituted with an oxygen atom, such as —CH$_2$CH$_2$OCH(CH$_3$)CH$_2$—. "Thiaalkylene" refers to an alkylene group as defined above where one or more non-adjacent CH$_2$ groups have been substituted with a sulfur atom, such as —CH$_2$CH$_2$SCH(CH$_3$)CH$_2$—.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester (—CO$_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF$_2$—, —OCF$_2$CF$_2$—, —OCF$_2$CH$_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate (in addition to the polymerizable group to which the linking group is linked).

Preferred linking groups include C$_1$-C$_8$ alkylene (preferably C$_2$-C$_6$ alkylene) and C$_1$-C$_8$ oxaalkylene (preferably C$_2$-C$_6$ oxaalkylene), each of which is optionally substituted with 1 or 2 groups independently selected from hydroxyl and siloxy. Preferred linking groups also include carboxylate, amide, C$_1$-C$_8$ alkylene-carboxylate-C$_1$-C$_8$ alkylene, or C$_1$-C$_8$ alkylene-amide-C$_1$-C$_8$ alkylene.

When the linking group is comprised of combinations of moieties as described above (e.g., alkylene and cycloalkylene), the moieties may be present in any order. For instance, if in Formula A above, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg or Pg) to which the linking group is attached. For example, if in Formula A, L is indicated as being alkylene-cycloalkylene, then Rg-L is preferably Rg-alkylene-cycloalkylene-.

The term "electron withdrawing group" (EWG) refers to a chemical group which withdraws electron density from the atom or group of atoms to which the electron withdrawing group is attached. Examples of EWGs include, but are not limited to, cyano, amide, ester, keto, or aldehyde. A preferred EWG is cyano (CN).

The terms "light absorbing compound" refers to a chemical material that absorbs light within the visible spectrum (e.g., in the 380 to 780 nm range). A "high energy radiation absorber," "UV/HEV absorber," "UV/HEV absorbing compound," or "high energy light absorbing compound" is a chemical material that absorbs various wavelengths of ultraviolet light, high energy visible light, or both. A material's ability to absorb certain wavelengths of light can be determined by measuring its UV/VIS transmission spectrum. Compounds that exhibit no absorption at a particular wavelength will exhibit substantially 100 percent transmission at that wavelength. Conversely, compounds that completely absorb at a particular wavelength will exhibit substantially 0% transmission at that wavelength. If the amount of a material's transmission is indicated as a percentage for a particular wavelength range, it is to be understood that the material exhibits the percent transmission at all wavelengths within that range.

When the compounds described herein contain olefinic double bonds or other centers of geometric asymmetry, and unless otherwise specified, it is intended that the compounds include the cis, trans, Z- and E-configurations. Likewise, all tautomeric and salt forms are also intended to be included.

The term "optional substituent" means that a hydrogen atom in the underlying moiety is optionally replaced by a substituent. Any substituent may be used that is sterically practical at the substitution site and is synthetically feasible. Identification of a suitable optional substituent is well within the capabilities of an ordinarily skilled artisan. Examples of an "optional substituent" include, without limitation, C$_1$-C$_6$ alkyl, C$_1$-C$_6$ alkoxy, C$_1$-C$_6$ thioalkyl, C$_3$-C$_7$ cycloalkyl, aryl, halo, hydroxy, amino, NR$^4$R$^5$, benzyl, SO$_3$H, or SO$_3$Na, wherein R$^4$ and R$^5$ are independently H or C$_1$-C$_6$ alkyl. The foregoing substituents may be optionally substituted by an optional substituent (which, unless otherwise indicated, is preferably not further substituted). For instance, alkyl may be substituted by halo (resulting, for instance, in CF$_3$).

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

In some embodiments, the reactive monomer mixture includes at least one polyamide. As used herein, the term "polyamide" refers to polymers and copolymers comprising repeating units containing amide groups. The polyamide may comprise cyclic amide groups, acyclic amide groups and combinations thereof, and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups. Polyamides suitable for use with the presently disclosed compositions and methods are disclosed in U.S. Patent Application Publication No. 20180009922 for SILICONE HYDROGELS COMPRISING HIGH LEVELS OF POLYAMIDES to Alli et al., published Jan. 11, 2018, and U.S. Patent Application Publication No. 20180011222 for SILICONE HYDROGELS COMPRISING POLYAMIDES to Alli et al., published Jan. 11, 2018, each of which are incorporated herein by reference in their entirety.

"Abbe number," also known as the V-number or constringence of a transparent material, is a measure of the material's dispersion, i.e., variation of refractive index versus wavelength, with high values of V indicating low dispersion. The Abbe number of a material is defined as:

$$V_D = \frac{n_D - 1}{n_F - n_C};$$

where $n_D$, $n_F$ and $n_C$ are the refractive indices of the material at the wavelengths of the Fraunhofer D-, F- and C-spectral lines (589.3 nm, 486.1 nm and 656.3 nm respectively).

"Refractive index" is defined as:

$$n = \frac{c}{v};$$

where c is the speed of light in a vacuum and v is the phase velocity of light in the medium.

B. Compositions

In some embodiments, the presently disclosed subject matter provides a composition made by free radical polymerization of a reactive monomer mixture comprising:

(A) (i) at least one cycloaliphatic (meth)acrylate; (ii) at least one aromatic (meth)acrylate; (iii) at least one aliphatic (meth)acrylate; and (iv) at least one cross-linking agent; wherein the composition exhibits a refractive index of at least 1.45 and an Abbe number of at least 39 (hereinafter "Composition (A)");

(B) (i) at least one cycloaliphatic (meth)acrylate; (ii) at least one aliphatic (meth)acrylate; and (iii) at least one cross-linking agent; wherein the composition exhibits a refractive index of at least 1.45 and an Abbe number of at least 39 (hereinafter "Composition (B)");

(C) (i) at least one hydrophobic monomer; (ii) at least one acrylate monomer of the following formula (I):

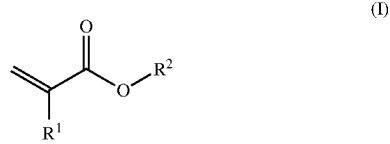

(I)

wherein $R^1$ is selected from hydrogen and methyl, and wherein $R^2$ is a non-aromatic moiety having at least one carbon-carbon double bond; and (iii) at least one cross-linking agent (hereinafter "Composition (C)");

(D) (i) at least one cycloaliphatic (meth)acrylate monomer containing more than one cycloaliphatic ring; (ii) at least one monomer selected from hydrophilic monomers and hydroxyalkyl (meth)acrylate monomers, and any combinations thereof, and (iii) at least one cross-linking agent; wherein the composition exhibits a refractive index of at least 1.45 and an Abbe number of at least 39 ("Composition (D)"); or (E) (i) at least one hydrophobic monomer; (ii) at least one monomer selected from hydrophilic monomers and hydroxyalkyl (meth)acrylate monomers, and any combinations thereof; and (iii) a tricyclo[5.2.1.0$^{2,6}$]decanedimethanol di(meth)acrylate cross-linking agent; wherein the composition exhibits a refractive index of at least 1.45 and an Abbe number of at least 39 ("Composition (E)").

Each of the compositions will now be described in more detail.

1. Composition (A)

In some embodiments, the presently disclosed subject matter provides a composition, referred to herein as "Composition (A)," made by free radical polymerization of a reactive monomer mixture comprising: (a) at least one cycloaliphatic (meth)acrylate; (b) at least one aromatic (meth)acrylate; (c) at least one aliphatic (meth)acrylate; and (d) at least one cross-linking agent; wherein the composition exhibits a refractive index of at least 1.45 and an Abbe number of at least 39.

In some embodiments of Composition (A), the at least one cycloaliphatic (meth)acrylate comprises a cycloaliphatic group having between one and four cycloaliphatic rings. In some embodiments, the cycloaliphatic group has one cycloaliphatic ring. The cycloaliphatic ring may be a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the at least one cycloaliphatic (meth)acrylate has at least one cycloaliphatic group comprising at least one carbon-carbon double bond. In some embodiments, the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, norbornyl PEG (meth)acrylate derivatives, isobornyl (meth)acrylate, isobornyl derivatives, norbornyl derivatives, ((1R,2S,4R)-bicyclo[2.2.1]hept-5-en-2-yl)methyl (meth)acrylate, ethylene glycol dicyclopentenyl ether (meth)acrylate, poly(ethylene glycol) dicyclopentenyl ether (meth)acrylate, 2,2-bis(cyclopent-1-en-1-yloxy)ethyl (meth)acrylate, (1R,3S,5f,7r)-2-methyladamantan-2-yl (meth)acrylate, (1R,3S,5f,7r)-2-methyladamantan-2-yl PEG (meth)acrylate derivates and (1R,3S,5f,7r)-2-methyladamantan-2-yl (meth)acrylate derivatives, and any combination thereof. In some embodiments, the cycloaliphatic (meth)acrylate is selected from cyclohexyl (meth)acrylate, cyclopentyl (meth)acrylate, cyclohexylmethyl (meth)acrylate, 2-cyclohexylethyl (meth)acrylate, 3-cyclohexylpropyl (meth)acrylate, ethylene glycol dicyclopentenyl ether (meth)acrylate, and any combination thereof. In some embodiments, the cycloaliphatic (meth)acrylate is selected from cyclohexyl acrylate, cyclohexylmethyl acrylate, cyclohexylmethyl methacrylate, 2-cyclohexylethylacrylate, 2-cyclohexylethyl methacrylate, 3-cyclohexylpropylacrylate, ethylene glycol dicyclopentenyl ether acrylate, and any combination thereof. In some embodiments, the cycloaliphatic (meth)acrylate is selected from cyclohexyl acrylate, cyclohexylmethyl acrylate, 2-cyclohexylethylacrylate, 3-cyclohexylpropylacrylate, and any combination thereof. In some embodiments, the cycloaliphatic (meth)acrylate is selected from cyclohexylmethyl acrylate, cyclohexylmethyl methacrylate, ethylene glycol dicyclopentenyl ether acrylate, and any combination thereof. In some embodiments, the cycloaliphatic (meth)acrylate is selected from 2-cyclohexylethyl acrylate, 2-cyclohexylethyl methacrylate, ethylene glycol dicyclopentenyl ether acrylate, and any combination thereof. In some embodiments, the at least one cycloaliphatic (meth)acrylate is cyclohexyl acrylate. In some embodiments, the at least one cycloaliphatic (meth)acrylate is cyclohexylmethyl acrylate. In some embodiments, the at least one cycloaliphatic (meth)acrylate is 2-cyclohexylethyl acrylate. In some embodiments, the at least one cycloaliphatic (meth)acrylate is ethylene glycol dicyclopentenyl ether acrylate.

In some embodiments, the cycloaliphatic (meth)acrylate does not include a substituent (e.g., a hydroxy substituent) on the cycloaliphatic moiety or anywhere else on the monomer (e.g., in a monomer such as 2-cyclohexylethyl (meth) acrylate, the monomer does not include a substituent such as a hydroxy substituent on either the cyclohexyl moiety or the ethyl moiety).

In some embodiments, the reactive monomer mixture of Composition (A) comprises the at least one cycloaliphatic (meth)acrylate in amount between about 20 and about 80 weight percent, including about 20, 25, 30, 35, 40, 45, 50, 55, 60, 65, 70, 75, and 80 weight percent, between about 40 and about 80 weight percent, including about 40, 45, 50, 55, 60, 65, 70, 75, and 80 weight percent, or between about 60 and about 80 weight percent, including about 60, 65, 70, 75, and 80 weight percent. In some embodiments, the weight percent of the at least one cycloaliphatic (meth)acrylate present in the reactive monomer mixture is calculated excluding a diluent.

In some embodiments of Composition (A), the at least one aromatic (meth)acrylate is a (meth)acrylate comprising at least one aryl group. In some embodiments, the aryl group is a phenyl group. In some embodiments, the aryl group can be present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, or 3-phenoxypropyl), or an arylthioalkyl group (e.g., phenylthiomethyl, 2-phenylthioethyl, or 3-phenylthiopropyl). In some embodiments, the at least one aromatic (meth)acrylate is selected from 2-phenylethyl (meth)acrylate, 2-phenoxyethyl (meth)acrylate, 3-phenylpropyl (meth)acrylate, 4-phenylbutyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments the aromatic (meth)acrylate is a combination of 2-phenylethyl acrylate and 2-phenylethyl methacrylate. In some embodiments, the at least one aromatic (meth)acrylate is 2-phenylethyl acrylate. In some embodiments, the at least one aromatic (meth)acrylate is 2-phenylethyl methacrylate. In some embodiments, the aromatic (meth)acrylate is 3-phenylpropyl acrylate. In some embodiments, the aromatic (meth)acrylate is 4-phenylbutyl acrylate.

In some embodiments, the at least one aromatic (meth)acrylate has at least one aliphatic group comprising at least one carbon-carbon double bond. In some embodiments, the at least one aromatic (meth)acrylate is cinnamyl (meth)acrylate.

In some embodiments, the reactive monomer mixture of Composition (A) comprises the at least one aromatic (meth)acrylate in an amount between about 5 and about 50 weight percent, including about 5, 10, 15, 20, 25, 30, 35, and 40 eight percent, between about 10 and about 40 weight percent, including about 10, 15, 20, 25, 30, 35, and 40 weight percent, or between about 15 and about 40 weight percent, including about 15, 20, 25, 30, 35, and 40 weight percent. In some embodiments, the weight percent of the at least one aromatic (meth)acrylate present in the reactive monomer mixture is calculated excluding a diluent.

In some embodiments of Composition (A), the cycloaliphatic (meth)acrylate(s) and the aromatic (meth)acrylate(s) are present in the reactive monomer mixture in a ratio of about 95:5 to about 30:70, about 90:10 to about 40:60, or about 90:10 to about 45:55. For example, in some embodiments, the cycloaliphatic (meth)acrylate(s) and the aromatic (meth)acrylate(s) are present in the reactive monomer mixture in a ratio of about 95:5, about 90:10, about 85:15, about 80:20, about 75:25, about 70:30, about 65:35, about 60:40, about 55:45, about 50:50, about 45:55, about 40:60, about 35:65, or about 30:70.

In some embodiments of Composition (A), the at least one aliphatic (meth)acrylate comprises a linear or branched alkyl group containing between 1 and 25 carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In particular embodiments, the aliphatic (meth)acrylate is a $C_1$-$C_{20}$ alkyl (meth)acrylate, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl (meth)acrylate. In more particular embodiments, the $C_1$-$C_{20}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof. In yet more particular embodiments, the aliphatic (meth)acrylate comprises a linear alkyl group containing between 4 and 8 carbon atoms (a $C_4$-$C_8$ linear alkyl group), including 4, 5, 6, 7 and 8 carbon atoms. In some embodiments, the aliphatic (meth)acrylate is n-hexyl acrylate.

In some embodiments, the at least one aliphatic (meth)acrylate has at least one aliphatic group comprising at least one carbon-carbon double bond.

In some embodiments, the reactive monomer mixture of Composition (A) comprises the at least one aliphatic (meth)acrylate in an amount between 1 and 40 weight percent, including about 1, 5, 10, 15, 20, 25, 30, 35, and 40 weight percent, between about 1 and about 20 weight percent, including about 1, 5, 10, 15, and 20 weight percent, or between about 1 and about 10 weight percent, including about 1, 2, 3, 4, 5, 6, 7, 8, 9, and 10 weight percent. In some embodiments, the weight percent of the at least one aliphatic (meth)acrylate present in the reactive monomer mixture is calculated excluding a diluent.

In some embodiments of Composition (A), the at least one cross-linking agent is selected from the group consisting of a non-cycloaliphatic cross-linking agent, a cycloaliphatic cross-linking agent, and any combination thereof. In certain embodiments, the at least one cross-linking agent is a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof. In more certain embodiments, the non-cycloaliphatic cross-linking agent is ethylene glycol dimethacrylate. In particular embodiments, the at least one cross-linking agent is a cycloaliphatic cross-linking agent comprising a cycloaliphatic group having between one and four cycloaliphatic rings. In yet more particular embodiments, the cycloaliphatic cross-linking agent is tricyclo[$5.2.1.0^{2,6}$]decanedimethanol di(meth)acrylate (e.g., tricyclo[$5.2.1.0^{2,6}$]decanedimethanol diacrylate).

In some embodiments, the reactive monomer mixture of Composition (A) comprises the cycloaliphatic cross-linking agent in an amount between about 1 and about 20 weight percent, including about 1, 2, 3, 4, 5, 6, 7, 8, 9, 10, 11, 12, 13, 14, 15, 16, 17, 18, 19, and 20 weight percent, between about 3 and about 15 weight percent, including about 3, 4, 5, 6, 7, 8, 9, 10, 11, 12, 13, 14, and 15 weight percent, or between about 3 and about 10 weight percent, including about 3, 4, 5, 6, 7, 8, 9, and 10 weight percent. In some embodiments, the weight percent of the cycloaliphatic crosslinking agent present in the reactive monomer mixture is calculated excluding a diluent.

In some embodiments of Composition (A), the reactive monomer mixture further comprises a polyamide. In some embodiments, the at least one polyamide is selected from poly(vinyl pyrrolidone), poly(N-vinyl-N-methyl acetamide), poly(N-vinyl acetamide), poly(dimethyl acrylamide), and a copolymer or a mixture thereof. In particular embodiments, the at least one polyamide is selected from poly(vinyl pyrrolidone) and poly(N-vinyl-N-methyl acetamide). In certain embodiments, the at least one polyamide is a copolymer.

In some embodiments, the reactive monomer mixture of Composition (A) comprises the at least one polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the at least one polyamide present in the reactive monomer mixture is calculated excluding a diluent.

In some embodiments, the reactive monomer mixture of Composition (A) further comprises at least one hydroxy silicone monomer.

In some embodiments, the reactive monomer mixture of Composition (A) further comprises at least one hydroxy silicone monomer. In certain embodiments, the at least one hydroxy silicone monomer comprises mono-n-butyl terminated mono-(2-hydroxy-3-methacryloxypropyloxy)-propyl terminated polydimethylsiloxane, 3-(3-(1,1,1,3,5,5,5 heptamethyltrisiloxan-3-yl)propoxy)-2-hydroxypropyl methacrylate, 3-(3-(1,5-di-tert-butyl-1,1,3,5,5-pentamethyltrisiloxan-3-yl)propoxy)-2-hydroxypropyl methacrylate, or any combination thereof.

In some embodiments, the reactive monomer mixture of Composition (A) comprises the hydroxy silicone monomer in an amount between about 1 and about 25 weight percent, including about 1, 5, 10, 15, 20, and 25 weight percent, between about 5 and about 20 weight percent, including about 5, 6, 7, 8, 9, 10, 11, 12, 13, 14, 15, 16, 17, 18, 19, and 20 weight percent, or between about 10 and about 20 weight percent, including 10, 11, 13, 13, 14, 15, 16, 17, 18, 19, and 20 weight percent. In some embodiments, the weight percent of the hydroxy silicone monomer present in the reactive monomer mixture is calculated excluding a diluent.

In some embodiments, the reactive monomer mixture of Composition (A) further comprises at least one hydroxyalkyl (meth)acrylate. In some embodiments, the hydroxyalkyl (meth)acrylate comprises a linear, branched, or cyclic hydroxyalkyl group having between 1 and 25 carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In some embodiments, the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth)acrylate, 4-hydroxybutyl (meth)acrylate, 1,1-dimethyl-2-hydroxyethyl (meth)acrylate, and any combination thereof. In some embodiments, the hydroxyalkyl (meth)acrylate is 4-hydroxybutyl acrylate or 2-hydroxyethyl methacrylate. In particular embodiments, the hydroxyalkyl (meth)acrylate is 4 hydroxybutyl acrylate. In some embodiments, the hydroxyalkyl (meth)acrylate is 2-hydroxyethyl methacrylate.

In some embodiments, the reactive monomer mixture of Composition (A) comprises the hydroxyalkyl (meth)acrylate in an amount between about 1 and about 25 weight percent, including about 1, 5, 10, 15, 20, and 25 weight percent, between about 5 and about 20 weight percent, including about 5, 6, 7, 8, 9, 10, 11, 12, 13, 14, 15, 16, 17, 18, 19, and 20 weight percent, or between about 10 and about 20 weight percent, including 10, 11, 13, 13, 14, 15, 16, 17, 18, 19, and 20 weight percent. In some embodiments, the weight percent of the hydroxyalkyl (meth)acrylate present in the reactive monomer mixture is calculated excluding a diluent.

In some embodiments, the reactive monomer mixture of Composition (A) does not include a hydroxyalkyl (meth)acrylate.

In some embodiments, the reactive monomer mixture of Composition (A) further comprises at least one UV/HEV absorbing compound.

In some embodiments, the UV/HEV absorbing compound may take the form of Formula

Formula II

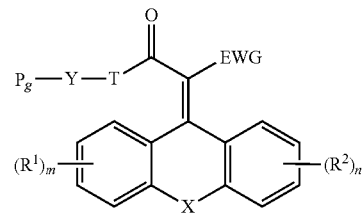

wherein:
m and n are independently 0, 1, 2, 3, or 4;
T is a bond, O, or NR;
X is O, S, NR, SO, or $SO_2$;
Y is a linking group;
$P_g$ is a polymerizable group;
R at each occurrence is independently H, $C_1$-$C_6$ alkyl, cycloalkyl, heterocycloalkyl, aryl, heteroaryl, or Y—$P_g$;
$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
EWG is an electron withdrawing group.

Compounds of Formula II preferably contain one or two Y—$P_g$ groups. More preferably, the compounds contain one Y—$P_g$ group.

In certain embodiments, the at least one UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof. In certain embodiments, the at least one UV/HEV absorbing compound is 2-(2-cyano-2-(9H-thioxanthen-9-ylidene)acetamido)ethyl methacrylate. In certain embodiments, the at least one UV/HEV absorbing compound is 3-(3-(tert-butyl)-5-(5-chloro-2H-benzo[d][1,2,3]triazol-2-yl)-4-hydroxyphenyl)propyl methacrylate.

In some embodiments, the reactive monomer mixture of Composition (A) comprises the at least one UV/HEV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV/HEV absorbing compound present in the reactive monomer mixture is calculated excluding a diluent.

In some embodiments, the reactive monomer mixture of Composition (A) further comprises at least one hydrophilic monomer. In some embodiments, the hydrophilic monomer is selected from vinyl pyrrolidone, N-vinyl-N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl)acrylamide, N-(2-hydroxyethyl)(meth)acrylamide, N-(2-hydroxypropyl)(meth)acrylamide, and N-(3-hydroxypropyl)(meth)acrylamide, poly(ethylene glycol) methyl ether (meth)acrylate, poly(ethylene glycol) (meth)acrylate, and any combination thereof. In some embodiments, the hydrophilic monomer has at least one aliphatic group having at least one double bond.

In some embodiments, the reactive monomer mixture of Composition (A) does not include a hydrophilic monomer.

In some embodiments, Composition (A) further comprises at least one diluent in the reactive monomer mixture.

In some embodiments, Composition (A) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent, or between about 0.5 and less than 5 weight percent, including 0.5, 1.0, 1.5, 2.0, 2.5, 3.0, 3.5, 4.0, and 4.5 weight percent. In some embodiments, the water content is measured when the material is hydrated at 37° C.

In some embodiments, Composition (A) has a refractive index of at least 1.45 and an Abbe number of at least 45. In other embodiments, Composition (A) has a refractive index of at least 1.48 and an Abbe number of at least 50. In yet other embodiments, Composition (A) has a refractive index of at least 1.50 and an Abbe number of at least 50. In some embodiments, the indicated refractive index and the indicated Abbe number are measured when the material is in a dry state at 25° C.

In some embodiments of Composition (A), the free radical polymerization is a photopolymerization using a bisacylphosphine oxide initiator. In some embodiments, the initiator is bis(2,4,6-trimethylbenzoyl)-phenylphosphineoxide.

(2) Composition (B)

In some embodiments, the presently disclosed subject matter provides a composition, referred to herein as "Composition (B)," made by free radical polymerization of a reactive monomer mixture comprising: (a) at least one cycloaliphatic (meth)acrylate; (b) at least one aliphatic (meth)acrylate; and (c) at least one cross-linking agent; wherein the composition exhibits a refractive index of at least 1.45 and an Abbe number of at least 39.

In some embodiments of Composition (B), the at least one cycloaliphatic (meth)acrylate comprises a cycloaliphatic group having between one and four cycloaliphatic rings. In some embodiments, the cycloaliphatic group has one cycloaliphatic ring. The cycloaliphatic ring may be a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the at least one cycloaliphatic (meth)acrylate has at least one cycloaliphatic group comprising at least one carbon-carbon double bond. In some embodiments, the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth)acrylate, isobornyl derivatives, norbornyl derivatives, ((1R,2S,4R)-bicyclo[2.2.1]hept-5-en-2-yl)methyl (meth)acrylate, ethylene glycol dicyclopentenyl ether (meth)acrylate, poly(ethylene) glycol dicyclopentenyl ether (meth)acrylate, 2,2-bis(cyclopent-1-en-1-yloxy)ethyl (meth)acrylate, 2-(((3aR,4R,5S,7R,7aR)-octahydro-1H-4,7-methanoinden-5-yl)oxy)ethyl acrylate, 2-(((3aS,4R,6S,7R,7aR)-3a,4,5,6,7,7a-hexahydro-1H-4,7-methanoinden-6-yl)oxy)ethyl acrylate, (3 aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R,3S,5f,7r)-2-methyladamantan-2-yl (meth)acrylate, (1R,3S,5f,7r)-2-methyladamantan-2-yl PEG (meth)acrylate derivates and (1R,3S,5f,7r)-2-methyladamantan-2-yl (meth)acrylate derivatives, and any combination thereof. In some embodiments, the cycloaliphatic (meth)acrylate is selected from cyclohexyl (meth)acrylate, cyclopentyl (meth)acrylate, cyclohexylmethyl (meth)acrylate, 2-cyclohexylethyl (meth)acrylate, 3-cyclohexylpropyl (meth)acrylate, and any combination thereof. In some embodiments, the cycloaliphatic (meth)acrylate is selected from cyclohexyl acrylate, cyclohexylmethyl acrylate, 2-cyclohexylethylacrylate, 3-cyclohexylpropylacrylate, and ethylene glycol dicyclopentenyl ether acrylate. In some embodiments, the cycloaliphatic (meth)acrylate is selected from cyclohexyl acrylate, cyclohexylmethyl acrylate, 2-cyclohexylethylacrylate, and 3-cyclohexylpropylacrylate. In some embodiments, the cycloaliphatic (meth)acrylate is cyclohexyl acrylate. In some embodiments, the cycloaliphatic (meth)acrylate is cyclohexylmethyl acrylate. In some embodiments, the cycloaliphatic (meth)acrylate is 2-cyclohexylethyl acrylate. In some embodiments, the cycloaliphatic (meth)acrylate is ethylene glycol dicyclopentenyl ether acrylate.

In some embodiments, the cycloaliphatic (meth)acrylate does not include a substituent (e.g., a hydroxy substituent) on the cycloaliphatic moiety or anywhere else on the monomer (e.g., in a monomer such as 2-cyclohexylethyl (meth)acrylate, the monomer does not include a substituent such as a hydroxy substituent on either the cyclohexyl moiety or the ethyl moiety).

In some embodiments, the reactive monomer mixture of Composition (B) comprises the at least one cycloaliphatic (meth)acrylate in amount between about 20 and about 80 weight percent, including about 20, 25, 30, 35, 40, 45, 50, 55, 60, 65, 70, 75, and 80 weight percent, between about 40 and about 80 weight percent, including about 40, 45, 50, 55, 60, 65, 70, 75, and 80 weight percent, or between about 60 and about 80 weight percent, including about 60, 65, 70, 75, and 80 weight percent. In some embodiments, the weight percent of the at least one cycloaliphatic (meth)acrylate present in the reactive monomer mixture is calculated excluding a diluent.

In some embodiments of Composition (B), the at least one aliphatic (meth)acrylate comprises a linear or branched alkyl group containing between 1 and 25 carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In particular embodiments, the aliphatic (meth)acrylate is a $C_1$-$C_{20}$ alkyl (meth)acrylate, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$ alkyl (meth)acrylate. In more particular embodiments, the $C_1$-$C_{20}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof. In yet more particular embodiments, the aliphatic (meth)acrylate comprises a linear or branched alkyl group containing between 4 and 8 carbon atoms (a $C_4$-$C_8$ linear alkyl group), including 4, 5, 6, 7, and 8 carbon atoms. In some embodiments, the aliphatic (meth)acrylate is isobutyl acrylate or n-hexyl acrylate.

In some embodiments, the reactive monomer mixture of Composition (B) comprises the at least one aliphatic (meth)acrylate in an amount between 1 and 40 weight percent, between about 1 and about 20 weight percent, or between about 1 and about 10 weight percent. In some embodiments, the weight percent of the at least one aliphatic (meth)acrylate present in the reactive monomer mixture is calculated excluding a diluent.

In some embodiments of Composition (B), the at least one cross-linking agent is selected from the group consisting of a non-cycloaliphatic cross-linking agent, a cycloaliphatic cross-linking agent, and any combination thereof. In certain embodiments, the at least one cross-linking agent is a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof. In more certain embodiments, the non-cycloaliphatic cross-linking agent is ethylene glycol dimethacrylate. In particular embodiments, the at least one cross-linking agent is a cycloaliphatic cross-linking agent comprising a cycloaliphatic group having between one and four cycloaliphatic rings. In yet more particular embodiments, the cycloaliphatic cross-linking agent is tricyclo[$5.2.1.0^{2,6}$]decanedimethanol di(meth)acrylate (e.g., tricyclo[$5.2.1.0^{2,6}$]decanedimethanol diacrylate).

In some embodiments, the reactive monomer mixture of Composition (B) comprises the cycloaliphatic cross-linking agent in an amount between about 1 and about 20 weight percent, including about 1, 5, 10, 15, and 20 weight percent, between about 3 and about 15 weight percent, including 3, 4, 5, 6, 7, 8, 9, 10, 11, 12, 13, 14, and 15, or between about 3 and about 10 weight percent, including 3, 4, 5, 6, 7, 8, 9, and 10 weight percent. In some embodiments, the weight percent of the cycloaliphatic cross-linking agent present in the reactive monomer mixture is calculated excluding a diluent.

In some embodiments, the reactive monomer mixture of Composition (B) further comprises an aromatic (meth)acrylate. In some embodiments, the aromatic (meth)acrylate is a (meth)acrylate comprising at least one aryl group. In some embodiments, the aryl group is a phenyl group. In some embodiments, the aryl group can be present in the aromatic (meth)acrylate as part of an arylalkyl group (e.g., benzyl, 2-phenylethyl, 3-phenylpropyl or 4-phenylpropyl), an aryloxyalkyl group (e.g., phenoxymethyl, 2-phenoxyethyl, or 3-phenoxypropyl), or an arylthioalkyl group (e.g., phenylthiomethyl, 2-phenylthioethyl, or 3 phenylthiopropyl). In some embodiments, the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is 2-phenylethyl acrylate. In some embodiments, the aromatic (meth)acrylate is 2-phenylethyl methacrylate. In some embodiments, the aromatic (meth)acrylate is 3-phenylpropyl acrylate. In some embodiments, the aromatic (meth)acrylate is 4-phenylbutyl acrylate.

In some embodiments, the reactive monomer mixture of Composition (B) comprises the aromatic (meth)acrylate in an amount between about 5 and about 50 weight percent, including about 5, 10, 15, 20, 25, 30, 35, 40, 45, and 50 weight percent, between about 10 and about 40 weight percent, including about 10, 15, 20, 25, 30, 35, and 40 weight percent, or between about 15 and about 40 weight percent, including about 15, 20, 25, 30, 35, and 40 weight percent. In some embodiments, the weight percent of the at least one aromatic (meth)acrylate present in the reactive monomer mixture is calculated excluding a diluent.

In some embodiments, Composition (B) does not include an aromatic monomer such as an aromatic (meth)acrylate.

In some embodiments, the reactive monomer mixture of Composition (B) further comprises at least one hydrophilic monomer. In some embodiments, the hydrophilic monomer is selected from vinyl pyrrolidone, N-vinyl-N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl)acrylamide, N-(2 hydroxyethyl)(meth)acrylamide, N-(2-hydroxypropyl)(meth)acrylamide, N-(3-hydroxypropyl)(meth)acrylamide, poly(ethylene glycol) methyl ether (meth)acrylate, poly(ethylene glycol) (meth)acrylate, and any combination thereof. In some embodiments, the hydrophilic monomer has at least one aliphatic group having at least one double bond.

In some embodiments, the reactive monomer mixture of Composition (B) does not include a hydrophilic monomer.

In some embodiments, the reactive monomer mixture of Composition (B) further comprises at least one hydroxyalkyl (meth)acrylate. In some embodiments, the hydroxyalkyl (meth)acrylate comprises a linear, branched, or cyclic hydroxyalkyl group having between 1 and 25 carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In some embodiments, the hydroxyalkyl (meth)acrylate is selected from 2-hydroxyethyl (meth)acrylate, 2-hydroxypropyl (meth)acrylate, 3-hydroxypropyl (meth)acrylate, 4-hydroxybutyl (meth)acrylate, and any combination thereof. In some embodiments, the hydroxyalkyl (meth)acrylate is 4-hydroxybutyl acrylate or 2-hydroxyethyl methacrylate. In particular embodiments, the hydroxyalkyl (meth)acrylate is 4-hydroxybutyl acrylate. In some embodiments, the hydroxyalkyl (meth)acrylate is 2-hydroxyethyl methacrylate.

In some embodiments, the reactive monomer mixture of Composition (B) comprises the hydroxyalkyl (meth)acrylate in an amount between about 1 and about 25 weight percent, including about 1, 5, 10, 15, 20, and 20 weight percent, between about 5 and about 20 weight percent, including about 5, 6, 7, 8, 9, 10, 11, 12, 13, 14, 15, 16, 17, 18, 19, and 20 weight percent, or between about 10 and about 20 weight percent, including about 10, 11, 12, 13, 14, 15, 16, 17, 18, 19, and 20 weight percent. In some embodiments, the weight percent of the hydroxyalkyl (meth)acrylate present in the reactive monomer mixture is calculated excluding a diluent.

In some embodiments, the reactive monomer mixture of Composition (B) does not include a hydroxyalkyl (meth) acrylate.

In some embodiments, the reactive monomer mixture of Composition (B) further comprises a polyamide. In some embodiments, the at least one polyamide is selected from poly(vinyl pyrrolidone), poly(N-vinyl N-methyl acetamide), poly(N-vinyl acetamide), poly(dimethyl acrylamide), and a copolymer or a mixture thereof. In particular embodiments, the at least one polyamide is selected from poly(vinyl pyrrolidone) and poly(N-vinyl N-methyl acetamide). In certain embodiments, the at least one polyamide is a copolymer.

In some embodiments, the reactive monomer mixture of Composition (B) comprises the at least one polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the at least one polyamide present in the reactive monomer mixture is calculated excluding a diluent.

In some embodiments, the reactive monomer mixture of Composition (B) further comprises at least one UV/HEV absorbing compound. In some embodiments, the UV/HEV absorbing compound may take the form of Formula II:

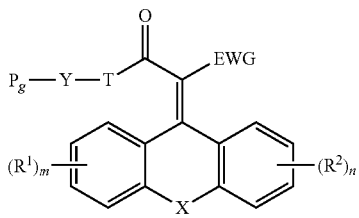

Formula II wherein:
m and n are independently 0, 1, 2, 3, or 4;
T is a bond, O, or NR;
X is O, S, NR, SO, or $SO_2$;
Y is a linking group;
$P_g$ is a polymerizable group;
R at each occurrence is independently H, $C_1$-$C_6$ alkyl, cycloalkyl, heterocycloalkyl, aryl, heteroaryl, or Y—$P_g$;
$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
EWG is an electron withdrawing group.

Compounds of Formula II preferably contain one or two Y—$P_g$ groups. More preferably, the compounds contain one Y—$P_g$ group.

In certain embodiments, the at least one UV/HEV absorbing compound is a compound of Formula II, is 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof. In certain embodiments, the at least one UV/HEV absorbing compound is 2-(2-cyano-2-(9H-thioxanthen-9-ylidene)acetamido)ethyl methacrylate. In certain embodiments, the at least one UV/HEV absorbing compound is 3-(3-(tert-butyl)-5-(5-chloro-2H-benzo[d][1,2,3]triazol-2-yl)-4-hydroxyphenyl)propyl methacrylate.

In some embodiments, the reactive monomer mixture of Composition (B) comprises the at least one UV/HEV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV/HEV absorbing compound present in the reactive monomer mixture is calculated excluding a diluent.

In some embodiments, the reactive monomer mixture of Composition (B) further comprises at least one diluent in the reactive monomer mixture.

In some embodiments, the reactive monomer mixture of Composition (B) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent, or between about 0.5 and less than 5 weight percent, including 0.5, 1.0, 1.5, 2.0, 2.5, 3.0, 3.5, 4.0, and 4.5 weight percent. In some embodiments, the water content is measured when the material is hydrated at 37° C.

In some embodiments, the reactive monomer mixture of Composition (B) has a refractive index of at least 1.45 and an Abbe number of at least 45. In other embodiments, Composition (B) has a refractive index of at least 1.48 and an Abbe number of at least 50. In yet other embodiments, Composition (B) has a refractive index of at least 1.50 and an Abbe number of at least 50. In some embodiments, the indicated refractive index and the indicated Abbe number are measured when the material is in a dry state at 25° C.

In some embodiments of Composition (B), the free radical polymerization is a photopolymerization using a bisacylphosphine oxide initiator. In some embodiments, the initiator is bis(2,4,6-trimethylbenzoyl)-phenylphosphineoxide.

(3) Composition (C)

In some embodiments, the presently disclosed subject matter provides a composition, referred to herein as "Composition (C)," made by free radical polymerization of a reactive monomer mixture comprising: (a) at least one hydrophobic monomer; (b) at least one acrylate monomer of the following formula (I):

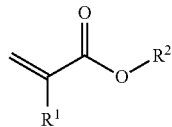
(I)

wherein $R^1$ is selected from hydrogen and methyl, and wherein $R^2$ is a non-aromatic moiety having at least one carbon-carbon double bond; and (c) at least one cross-linking agent.

In some embodiments of Composition (C), the hydrophobic monomer is a hydrophobic (meth)acrylate monomer. In some embodiments, the hydrophobic (meth)acrylate is selected from an aliphatic (meth)acrylate, an aromatic (meth)acrylate, a cycloaliphatic (meth)acrylate, and any combination thereof.

In particular embodiments, the hydrophobic (meth)acrylate is an aliphatic (meth)acrylate. In some embodiments, the aliphatic (meth)acrylate comprises a linear or branched alkyl group containing between 1 and 18 carbon atoms (a $C_1$-$C_{18}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl (meth)acrylate. In more particular embodiments, the $C_1$-$C_{18}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, isodecyl (meth)acrylate, heptadecyl (meth)acrylate, dodecyl (meth)acrylate, 2-propylheptyl (meth)acrylate, stearyl (meth)acrylate, and any combination thereof. In yet more particular embodiments, the aliphatic (meth)acrylate comprises a linear alkyl group containing between 4 and 8 carbon atoms (a $C_4$-$C_8$ linear alkyl group). In some embodiments, the aliphatic (meth)acrylate is n-hexyl acrylate.

In some embodiments, the hydrophobic (meth)acrylate is an aromatic (meth)acrylate. The aromatic (meth)acrylate is a (meth)acrylate comprising at least one aryl group. In some embodiments, the aryl group is a phenyl group. In some embodiments, the aryl group can be present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2 phenoxyethyl, or 3-phenoxypropyl), or an arylthioalkyl group (e.g., phenylthiomethyl, 2-phenylthioethyl, or 3-phenylthiopropyl). In some embodiments, the aromatic (meth)acrylate is selected from 2-phenylethyl (meth)acrylate, 2-phenoxyethyl (meth)acrylate, 3-phenylpropyl (meth)acrylate, 4-phenylbutyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is 2-phenylethyl acrylate. In some embodiments, the aromatic (meth)acrylate is 2-phenylethyl methacrylate. In some embodiments, the aromatic (meth)acrylate is a combination of 2-phenylethyl acrylate and 2-phenylethyl methacrylate. In some embodiments, the aromatic (meth)acrylate is 3-phenylpropyl acrylate. In some embodiments, the aromatic (meth)acrylate is 4-phenylbutyl acrylate.

In some embodiments of Composition (C), the hydrophobic (meth)acrylate is a cycloaliphatic (meth)acrylate. In some embodiments, the cycloaliphatic (meth)acrylate comprises a cycloaliphatic group having between one and four cycloaliphatic rings. In some embodiments, the cycloaliphatic group has one cycloaliphatic ring. The cycloaliphatic ring may be a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the at least one cycloaliphatic (meth)acrylate has at least one cycloaliphatic group comprising at least one carbon-carbon double bond. In some embodiments, the cycloaliphatic (meth)acrylate is selected from cyclohexyl (meth)acrylate, cyclohexyl PEG (meth) acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth) acrylate, isobornyl derivatives, norbornyl derivatives, ((1R, 2S,4R)-bicyclo[2.2.1]hept-5-en-2-yl)methyl (meth)acrylate, ethylene glycol dicyclopentenyl ether (meth)acrylate, poly (ethylene) glycol dicyclopentenyl ether (meth)acrylate, 2,2-bis(cyclopent-1-en-1-yloxy)ethyl (meth)acrylate, 2-(((3aR, 4R,5S,7R,7aR)-octahydro-1H-4,7-methanoinden-5-yl)oxy) ethyl acrylate, 2-(((3aS,4R,6S,7R,7aR)-3a,4,5,6,7,7a-hexahydro-1H-4,7-methanoinden-6-yl)oxy)ethyl acrylate, (3aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R,3S,5f,7r)-2-methyladamantan-2-yl (meth)acrylate, (1R,3S,5f,7r)-2-methyladamantan-2-yl PEG (meth)acrylate derivates and (1R,3S,5f, 7r)-2-methyladamantan-2-yl (meth)acrylate derivatives, and any combination thereof. In some embodiments, the cycloaliphatic (meth)acrylate is selected from cyclohexyl (meth) acrylate, cyclopentyl (meth)acrylate, cyclohexylmethyl (meth)acrylate, 2-cyclohexylethyl (meth)acrylate, 3-cyclohexylpropyl (meth)acrylate, and any combination thereof. In some embodiments, the cycloaliphatic (meth)acrylate is cyclohexyl acrylate. In some embodiments, the cycloaliphatic (meth)acrylate is cyclohexylmethyl acrylate. In some embodiments, the cycloaliphatic (meth)acrylate is 2-cyclohexylethyl acrylate. In some embodiments, the cycloaliphatic (meth)acrylate is ethylene glycol dicyclopentenyl ether acrylate.

In some embodiments, the cycloaliphatic (meth)acrylate does not include a substituent (e.g., a hydroxy substituent) on the cycloaliphatic moiety or anywhere else on the monomer (e.g., in a monomer such as 2-cyclohexylethyl (meth) acrylate, the monomer does not include a substituent such as a hydroxy substituent on either the cyclohexyl moiety or the ethyl moiety).

Composition (C) also includes at least one acrylate monomer of formula (I):

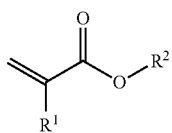
(I)

wherein R¹ is selected from hydrogen and methyl, and wherein R² is a non-aromatic moiety having at least one carbon-carbon double bond.

In some embodiments, R¹ is hydrogen. In some embodiments, R² is methyl.

In some embodiments, in the at least one acrylate monomer of formula (I), R² comprises an alkenyl or cycloalkenyl moiety. In particular embodiments, R² comprises a cyclopentenyl, cyclopentadienyl, cyclohexenyl, cyclohexadienyl, bicyclo[2.2.1]hept-5-en-2-yl, 3a,4,5,6,7,7a-hexahydro-1H-4,7-methanoindenyl, styryl, cinnamyl, or allyl moiety.

In more particular embodiments, the acrylate monomer of formula (I) is selected from ethylene glycol dicyclopentenyl ether (meth)acrylate, ((1R,2 S,4R)-bicyclo[2.2.1]hept-5-en-2-yl)methyl acrylate, 2-(((3aS,4R,6S,7R,7aR)-3a,4,5,6,7,7a-hexahydro-1H-4,7-methanoinden-6-yl)oxy)ethyl acrylate, poly(ethylene glycol) dicyclopentenyl ether (meth)acrylate, 2,2-bis(cyclopent-1-en-1-yloxy)ethyl (meth)acrylate, (3aS,4S,5R,7S,7aS)-3a,4,5,6,7,7a-hexahydro-1H-4,7-methanoinden-5-yl acrylate, 2-(cyclopenta-2,4-dien-1-yloxy)ethyl acrylate, cyclopenta-2,4-dien-1-yl acrylate, cyclopent-3-en-1-yl acrylate, 2-(cyclopent-3-en-1-yloxy)ethyl acrylate, cyclohexa-2,4-dien-1-yl acrylate, 2-(cyclohexa-2,4-dien-1-yloxy)ethyl acrylate, 2-(cyclohex-3-en-1-yloxy)ethyl acrylate, cyclohex-3-en-1-yl acrylate, 2-(2-(2-(2-(cyclohex-3-en-1-yloxy)ethoxy)ethoxy)ethoxy)ethyl acrylate, N N-diallyl acrylamide, allyl acrylate, and 2-(allyloxy)ethyl acrylate.

In some embodiments, the reactive monomer mixture of Composition (C) further comprises a hydroxyl-containing monomer. In some embodiments, the hydroxyl-containing monomer is a hydroxyalkyl (meth)acrylate. In some embodiments, the hydroxyalkyl (meth)acrylate comprises a linear, branched, or cyclic hydroxyalkyl group having between 1 and 25 carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In some embodiments, the hydroxyalkyl (meth)acrylate is selected from 2-hydroxyethyl (meth)acrylate, 2-hydroxypropyl (meth)acrylate, 3-hydroxypropyl (meth)acrylate, 4-hydroxybutyl (meth)acrylate, and any combination thereof. In particular embodiments, the hydroxyalkyl (meth)acrylate is 2-hydroxyethyl methacrylate or 4-hydroxybutyl acrylate. In some embodiments, the hydroxyalkyl (meth)acrylate is 2-hydroxyethyl methacrylate.

In some embodiments, the hydroxyl-containing monomer is a hydroxysilicone monomer. In some embodiments, the hydroxysilicone monomer is selected from 3-(3-(1,1,1,3,5,5,5-heptamethyltrisiloxan-3-yl)propoxy)-2-hydroxypropyl methacrylate (SiMAA), mono-n-butyl terminated monomethacryloxypropyl terminated polydimethylsiloxane (mPDMS), and mono-(2-hydroxy-3-methacryloxypropyl)-propyl ether terminated mono-n-butyl terminated polydimethylsiloxane (OH-mPDMS).

In some embodiments, the reactive monomer mixture of Composition (C) further comprises at least one hydrophilic monomer. In some embodiments, the hydrophilic monomer is selected from vinyl pyrrolidone, N-vinyl-N-methyl acetamide, N-methyl methacrylamide, N-vinyl acetamide, N,N-dimethyl acrylamide, N-hydroxyethylacrylamide, N-(2 hydroxypropyl)acrylamide, N-(3-hydroxypropyl)acrylamide, N-(2-hydroxyethyl)(meth)acrylamide, N-(2-hydroxypropyl)(meth)acrylamide, N-(3-hydroxypropyl)(meth)acrylamide, poly(ethylene glycol) methyl ether (meth)acrylate, poly(ethylene glycol) (meth)acrylate, and any combination thereof. In some embodiments, the hydrophilic monomer has at least one aliphatic group having at least one double bond.

In some embodiments of Composition (C), the at least one cross-linking agent is selected from the group consisting of a non-cycloaliphatic cross-linking agent, a cycloaliphatic cross-linking agent, and any combination thereof. In certain embodiments, the at least one cross-linking agent is a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof. In more certain embodiments, the non-cycloaliphatic cross-linking agent is ethylene glycol dimethacrylate. In particular embodiments, the at least one cross-linking agent is a cycloaliphatic cross-linking agent comprising a cycloaliphatic group having between one and four cycloaliphatic rings. In yet more particular embodiments, the cycloaliphatic cross-linking agent is tricyclo[5.2.1.0²,⁶]decanedimethanol di(meth)acrylate (e.g., tricyclo[5.2.1.0²,⁶]decanedimethanol diacrylate).

In some embodiments, the reactive monomer mixture of Composition (C) comprises the cycloaliphatic cross-linking agent in an amount between about 1 and about 20 weight percent, including about 1, 5, 10, 15, and 20 weight percent, between about 3 and about 15 weight percent, including about 3, 4, 5, 6, 7, 8, 9, 10, 11, 12, 13, 14, and 15 weight percent, or between about 3 and about 10 weight percent, including about 3, 4, 5, 6, 7, 8, 9, and 10 weight percent. In some embodiments, the weight percent of the cycloaliphatic cross-linking agent present in the reactive monomer mixture is calculated excluding a diluent.

In some embodiments, the cross-linking agent has formula:

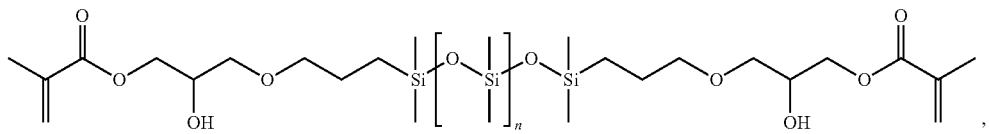

wherein n is an integer from 5 to 50, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In some embodiments, n is 15, 16, 17, 18, 19, 20, 21, 22, 23, 24, or 25. In particular embodiments, n is 20. In some embodiments, the reactive monomer mixture comprises the cross-linking agent in an amount of about 15% to about 22% by weight, or between about 16% to about 20% by weight. In particular embodiments, the cross-linking agent is present in the reactive monomer mixture in an amount of about 18% by weight.

In some embodiments of Composition (C), the reactive monomer mixture further comprises a polyamide. In some embodiments, the at least one polyamide is selected from poly(vinyl pyrrolidone), poly(N-vinyl-N-methyl acetamide), poly(N-vinyl acetamide), poly(dimethyl acrylamide), and a copolymer or a mixture thereof. In particular embodiments, the at least one polyamide is selected from poly(vinyl pyrrolidone) and poly(N-vinyl-N-methyl acetamide). In certain embodiments, the at least one polyamide is a copolymer.

In some embodiments, the reactive monomer mixture of Composition (C) comprises the at least one polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the at least one polyamide present in the reactive monomer mixture is calculated excluding a diluent.

In some embodiments, Composition (C) further comprises at least one UV/HEV absorbing compound in the reactive monomer mixture. In some embodiments, the UV/HEV absorbing compound may take the form of Formula II:

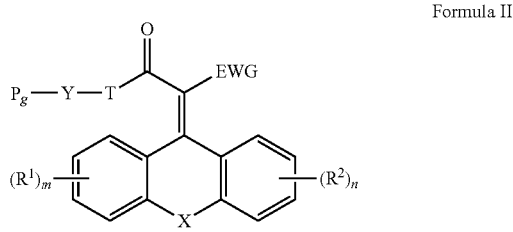

Formula II wherein:
m and n are independently 0, 1, 2, 3, or 4;
T is a bond, O, or NR;
X is O, S, NR, SO, or $SO_2$;
Y is a linking group;
$P_g$ is a polymerizable group;
R at each occurrence is independently H, $C_1$-$C_6$ alkyl, cycloalkyl, heterocycloalkyl, aryl, heteroaryl, or Y—$P_g$;
$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
EWG is an electron withdrawing group.

Compounds of Formula II preferably contain one or two Y—$P_g$ groups. More preferably, the compounds contain one Y—$P_g$ group.

In certain embodiments, the at least one UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof. In certain embodiments, the at least one UV/HEV absorbing compound is 2-(2-cyano-2-(9H-thioxanthen-9-ylidene)acetamido)ethyl methacrylate. In certain embodiments, the at least one UV/HEV absorbing compound is 3-(3-(tert-butyl)-5-(5-chloro-2H-benzo[d][1,2,3]triazol-2-yl)-4-hydroxyphenyl)propyl methacrylate.

In some embodiments, the reactive monomer mixture of Composition (C) comprises the at least one UV/HEV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV/HEV absorbing compound present in the reactive monomer mixture is calculated excluding a diluent.

In some embodiments, Composition (C) further comprises at least one diluent in the reactive monomer mixture.

In some embodiments, Composition (C) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent, or between about 0.5 and less than 5 weight percent, including 0.5, 1.0, 1.5, 2.0, 2.5, 3.0, 3.5, 4.0, and 4.5 weight percent. In some embodiments, the water content is measured when the material is hydrated at 37° C.

In some embodiments, Composition (C) has a refractive index of at least 1.45 and an Abbe number of at least 45. In other embodiments, Composition (C) has a refractive index of at least 1.48 and an Abbe number of at least 50. In yet other embodiments, Composition (C) has a refractive index of at least 1.50 and an Abbe number of at least 50. In some embodiments, the indicated refractive index and the indicated Abbe number are measured when the material is in a dry state at 25° C.

In some embodiments of Composition (C), the free radical polymerization is a photopolymerization using a bisacylphosphine oxide initiator. In some embodiments, the initiator is bis(2,4,6-trimethylbenzoyl)-phenylphosphineoxide.

(4) Composition (D)

In some embodiments, the presently disclosed subject matter provides a composition, referred to herein as "Composition (D)," made by free radical polymerization of a reactive monomer mixture comprising: (i) at least one cycloaliphatic (meth)acrylate monomer containing more than one cycloaliphatic ring; (ii) at least one monomer selected from hydrophilic monomers and hydroxyalkyl (meth)acrylate monomers, and any combinations thereof; and (iii) at least one cross-linking agent ("Composition (D)"); wherein the composition exhibits a refractive index of at least 1.45 and an Abbe number of at least 39.

In some embodiments, the at least one cycloaliphatic (meth)acrylate monomer containing more than one cycloaliphatic ring includes two or more separate monocyclic cycloaliphatic rings. In some embodiments, the at least one cycloaliphatic (meth)acrylate monomer containing more than one cycloaliphatic ring includes a single bicyclic, tricyclic, bridged, fused, and/or spirocyclic cycloaliphatic ring system. In some embodiments, the at least one cycloaliphatic (meth)acrylate monomer containing more than one cycloaliphatic ring has at least one cycloaliphatic group comprising at least one carbon-carbon double bond. In some embodiments, the cycloaliphatic (meth)acrylate monomer containing more than one cycloaliphatic ring is selected from norbornyl (meth)acrylate, isobornyl (meth)acrylate, isobornyl derivatives, norbornyl derivatives, ((1R,2S,4R)-bicyclo[2.2.1]hept-5-en-2-yl)methyl (meth)acrylate, ethylene glycol dicyclopentenyl ether (meth)acrylate, poly(ethylene) glycol dicyclopentenyl ether (meth)acrylate, 2,2-bis (cyclopent-1-en-1-yloxy)ethyl (meth)acrylate, 2-(((3aR,4R, 5S,7R,7aR)-octahydro-1H-4,7-methanoinden-5-yl)oxy) ethyl acrylate, 2-(((3aS,4R,6S,7R,7aR)-3a,4,5,6,7,7a-hexahydro-1H-4,7-methanoinden-6-yl)oxy)ethyl acrylate, (3aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R,3S,5f,7r)-2-methyladamantan-2-yl (meth)acrylate, (1R,3S,5f,7r)-2-methyladamantan-2-yl PEG (meth)acrylate derivates and (1R,3S,5f, 7r)-2-methyladamantan-2-yl (meth)acrylate derivatives, and any combination thereof. In some embodiments, the at least one cycloaliphatic (meth)acrylate monomer containing more than one cycloaliphatic ring is ethylene glycol dicyclopentenyl ether acrylate.

In some embodiments, the cycloaliphatic (meth)acrylate containing more than one cycloaliphatic ring does not include a substituent (e.g., a hydroxy substituent) on the cycloaliphatic moiety or anywhere else on the monomer.

In some embodiments, the reactive monomer mixture of Composition (D) comprises the cycloaliphatic (meth)acrylate monomer containing more than one cycloaliphatic ring in an amount between about 40 and about 90 weight percent, including about 40, 45, 50, 55, 60, 65, 70, 75, 80, 85, and 90 weight percent, between about 50 and about 80 weight percent, including about 50, 55, 60, 65, 70, 75, and 80 weight percent, or between about 50 and about 70 weight percent, including about 50, 51, 52, 53, 54, 55, 56, 57, 58, 59, 60, 61, 62, 63, 64, 65, 66, 67, 68, 69, and 70 weight percent. In some embodiments, the weight percent of the cycloaliphatic (meth)acrylate monomer containing more than one cycloaliphatic ring present in the reactive monomer mixture is calculated excluding a diluent.

In some embodiments, the reactive monomer mixture of Composition (D) comprises at least one hydrophilic monomer. In some embodiments, the at least one hydrophilic monomer is selected from vinyl pyrrolidone, N-vinyl-N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl) acrylamide, N-(2 hydroxyethyl)(meth)acrylamide, N-(2-hydroxypropyl)(meth)acrylamide, and N-(3-hydroxypropyl) (meth)acrylamide, poly(ethylene glycol) methyl ether (meth)acrylate, poly(ethylene glycol) (meth)acrylate, and any combination thereof.

In some embodiments, the hydrophilic monomer is a poly(ethylene glycol)-containing monomer. In some embodiments, the poly(ethylene glycol)-containing monomer is selected from poly(ethylene glycol) methyl ether (meth)acrylate and poly(ethylene glycol) (meth)acrylate. In some embodiments, the poly(ethylene glycol)-containing monomer is poly(ethylene glycol) methacrylate. In some embodiments, the poly(ethylene glycol)-containing monomer is poly(ethylene glycol) methyl ether methacrylate. In some embodiments, the reactive monomer mixture of Composition (D) comprises a combination of poly(ethylene glycol) methacrylate and poly(ethylene glycol) methyl ether methacrylate.

In some embodiments, the poly(ethylene glycol)-containing monomer has a number-average molecular weight ($M_n$) of about 200 g/mol to about 1000 g/mol, including 200 g/mol, 220 g/mol, 240 g/mol, 260 g/mol, 280 g/mol, 300 g/mol, 320 g/mol, 340 g/mol, 360 g/mol, 380 g/mol, 400 g/mol, 420 g/mol, 440 g/mol, 460 g/mol, 480 g/mol, 500 g/mol, 520 g/mol, 540 g/mol, 560 g/mol, 580 g/mol, 600 g/mol, 620 g/mol, 640 g/mol, 660 g/mol, 680 g/mol, 700 g/mol, 720 g/mol, 740 g/mol, 760 g/mol, 780 g/mol, 800 g/mol, 820 g/mol, 840 g/mol, 860 g/mol, 880 g/mol, 900 g/mol, 920 g/mol, 940 g/mol, 960 g/mol, 980 g/mol, and 1000 g/mol. In some embodiments, the poly(ethylene glycol)-containing monomer has a number-average molecular weight ($M_n$) of about 200 g/mol to about 400 g/mol, including 200 g/mol, 220 g/mol, 240 g/mol, 260 g/mol, 280 g/mol, 300 g/mol, 320 g/mol, 340 g/mol, 360 g/mol, 380 g/mol, and 400 g/mol.

In some embodiments, the poly(ethylene glycol)-containing monomer has formula:

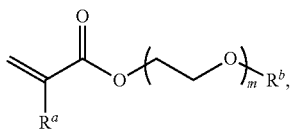

wherein $R^a$ and $R^b$ are each independently selected from hydrogen and methyl, and m is an integer from 2 to 25, including 2, 3, 4, 5, 6, 7, 8, 9, 10, 11, 12, 13, 14, 15, 16, 17, 18, 19, 20, 21, 22, 23, 24, and 25. In some embodiments, $R^a$ is hydrogen. In some embodiments, $R^a$ is methyl. In some embodiments, $R^b$ is hydrogen. In some embodiments, $R^b$ is methyl. In particular embodiments, $R^a$ is methyl and $R^b$ is hydrogen. In some embodiments, $R^a$ is methyl and $R^b$ is methyl. In some embodiments, m is an integer from 2 to 8, including 2, 3, 4, 5, 6, 7, and 8.

In some embodiments, the reactive monomer mixture of Composition (D) comprises the at least one hydrophilic monomer (e.g., the poly(ethylene glycol)-containing monomer) in amount between about 1 and about 40 weight percent, including about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 weight percent, between about 10 and about 30 weight percent, including about 10, 11, 12, 13, 14, 15, 16, 17, 18, 19, 20, 21, 22, 23, 24, 25, 26, 27, 28, 29, and 30 weight percent, between about 12 and about 22 weight percent, including about 12, 13, 14, 15, 16, 17, 18, 19, 20, 21, and 22 weight percent, or between about 14 and about 20 weight percent, including about 14, 15, 16, 17, 18, 19, and 20 weight percent. In some embodiments, the weight percent of the at least one hydrophilic monomer (e.g., the poly(ethylene glycol)-containing monomer) present in the reactive monomer mixture is calculated excluding a diluent.

In some embodiments, the reactive monomer mixture of Composition (D) comprises at least one hydroxyalkyl (meth) acrylate monomer. In some embodiments, the hydroxyalkyl (meth)acrylate comprises a linear, branched, or cyclic hydroxyalkyl group having between 1 and 25 carbon atoms (a $C_1$-$C_{25}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, and $C_{25}$. In some embodiments, the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth)acrylate, 4 hydroxybutyl (meth)acrylate, 1,1-dimethyl-2-hydroxyethyl (meth)acrylate, and any combination thereof. In some embodiments, the hydroxyalkyl (meth)acrylate is 4-hydroxybutyl acrylate or 2-hydroxyethyl methacrylate. In particular embodiments, the hydroxyalkyl (meth)acrylate is 4-hydroxybutyl acrylate. In some embodiments, the hydroxyalkyl (meth)acrylate is 2-hydroxyethyl methacrylate.

In some embodiments, the reactive monomer mixture of Composition (D) comprises the hydroxyalkyl (meth)acrylate in an amount between about 1 and about 10 weight percent, including about 1, 2, 3, 4, 5, 6, 7, 8, 9, and 10 weight percent, between about 2 and about 8 weight percent, including about 2, 3, 4, 5, 6, 7, and 8 weight percent, or between about 4 and about 6 weight percent, including 4, 5, and 6 weight percent. In some embodiments, the weight percent of the hydroxyalkyl (meth)acrylate present in the reactive monomer mixture is calculated excluding a diluent.

In some embodiments, the reactive monomer mixture of Composition (D) comprises a combination of a hydrophilic monomer and a hydroxyalkyl (meth)acrylate monomer. In some embodiments, the reactive monomer mixture comprises a combination of a poly(ethylene glycol)-containing monomer and a hydroxyalkyl (meth)acrylate monomer. In some embodiments, the reactive monomer mixture comprises a combination of poly(ethylene glycol) methyl ether (meth)acrylate and 2-hydroxyethyl (meth)acrylate. In some embodiments, the reactive monomer mixture comprises a combination of poly(ethylene glycol) (meth)acrylate and 2-hydroxyethyl (meth)acrylate.

In some embodiments, Composition (D) is made by free radical polymerization of a reactive monomer mixture comprising: (i) at least one cycloaliphatic (meth)acrylate monomer containing more than one cycloaliphatic ring; (ii) at least one poly(ethylene glycol)-containing monomer; and (iii) at least one cross-linking agent. In some embodiments, Composition (D) is made by free radical polymerization of a reactive monomer mixture comprising: (i) at least one cycloaliphatic (meth)acrylate monomer containing more than one cycloaliphatic ring; (ii) at least one poly(ethylene glycol)-containing monomer selected from poly(ethylene glycol) (meth)acrylate and poly(ethylene glycol) methyl ether (meth)acrylate; and (iii) at least one cross-linking agent.

In some embodiments, Composition (D) is made by free radical polymerization of a reactive monomer mixture comprising: (i) an ethylene glycol dicyclopentenyl ether (meth)acrylate monomer; (ii) at least one monomer selected from hydrophilic monomers and hydroxyalkyl (meth)acrylate monomers, and any combinations thereof; and (iii) at least one cross-linking agent.

In some embodiments, Composition (D) is made by free radical polymerization of a reactive monomer mixture comprising: (i) an ethylene glycol dicyclopentenyl ether (meth)acrylate monomer; (ii) at least one poly(ethylene glycol)-containing monomer; and (iii) at least one cross-linking agent. In some embodiments, Composition (D) is made by free radical polymerization of a reactive monomer mixture comprising: (i) an ethylene glycol dicyclopentenyl ether (meth)acrylate monomer; (ii) at least one poly(ethylene glycol)-containing monomer selected from poly(ethylene glycol) (meth)acrylate and poly(ethylene glycol) methyl ether (meth)acrylate; and (iii) at least one cross-linking agent.

In some embodiments, the reactive monomer mixture of Composition (D) further comprises at least one cycloaliphatic (meth)acrylate containing one cycloaliphatic ring. In some embodiments, the at least one cycloaliphatic (meth)acrylate containing one cycloaliphatic ring comprises a cycloaliphatic group having at least one carbon-carbon double bond. The cycloaliphatic ring may be a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the cycloaliphatic (meth)acrylate containing one cycloaliphatic ring is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3 cyclohexylpropyl (meth)acrylate, and any combination thereof. In some embodiments, the cycloaliphatic (meth)acrylate containing one cycloaliphatic ring is selected from cyclohexyl acrylate, cyclohexylmethyl acrylate, 2-cyclohexylethyl acrylate, 2-cyclohexylethyl methacrylate, 3-cyclohexylpropyl acrylate, and any combination thereof. In some embodiments, the cycloaliphatic (meth)acrylate containing one cycloaliphatic ring is selected from cyclohexyl acrylate, cyclohexyl methyl acrylate, 2-cyclohexylethyl acrylate, and 3-cyclohexylpropyl acrylate. In some embodiments, the cycloaliphatic (meth)acrylate is cyclohexyl acrylate. In some embodiments, the cycloaliphatic (meth)acrylate containing one cycloaliphatic ring is cyclohexylmethyl acrylate. In some embodiments, the cycloaliphatic (meth)acrylate containing one cycloaliphatic ring is cyclohexylmethyl methacrylate. In some embodiments, the cycloaliphatic (meth)acrylate containing one cycloaliphatic ring is 2-cyclohexylethyl acrylate. In some embodiments, the cycloaliphatic (meth)acrylate containing one cycloaliphatic ring is 2-cyclohexylethyl methacrylate. In some embodiments, the combination thereof is a combination of cyclohexylmethyl acrylate and cyclohexylmethyl methacrylate. In some embodiments, the combination thereof is a combination of 2-cyclohexylethyl acrylate and 2-cyclohexylethyl methacrylate.

In some embodiments, the cycloaliphatic (meth)acrylate does not include a substituent (e.g., a hydroxy substituent) on the cycloaliphatic moiety or anywhere else on the monomer (e.g., in a monomer such as 2-cyclohexylethyl (meth)acrylate, the monomer does not include a substituent such as a hydroxy substituent on either the cyclohexyl moiety or the ethyl moiety).

In some embodiments, the reactive monomer mixture of Composition (D) comprises the at least one cycloaliphatic (meth)acrylate containing one aliphatic ring in amount between about 10 and about 25 weight percent, including about 10, 11, 12, 13, 14, 15, 16, 17, 18, 19, 20, 21, 22, 23, 24, and 25 weight percent, between about 10 and about 20 weight percent, including about 10, 11, 12, 13, 14, 15, 16, 17, 18, 19, and 20 weight percent, or between about 12 and about 15 weight percent, including about 12, 13, 14, and 15 weight percent. In some embodiments, the weight percent of the at least one cycloaliphatic (meth)acrylate present in the reactive monomer mixture is calculated excluding a diluent.

In some embodiments, the reactive monomer mixture of Composition (D) further comprises at least one aromatic (meth)acrylate. In some embodiments, the at least one aromatic (meth)acrylate is a (meth)acrylate comprising at least one aryl group. In some embodiments, the aryl group is a phenyl group. In some embodiments, the aryl group can be present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, or 3-phenoxypropyl), or an arylthioalkyl group (e.g., phenylthiomethyl, 2-phenylthioethyl, or 3-phenylthiopropyl). In some embodiments, the at least one aromatic (meth)acrylate is selected from 2-phenylethyl (meth)acrylate, 2-phenoxyethyl (meth)acrylate, 3-phenylpropyl (meth)acrylate, 4-phenylbutyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the at least one aromatic (meth)acrylate is selected from 2-phenylethyl acrylate, 2-phenylethyl methacrylate, 3-phenylpropyl acrylate, and 4-phenylbutyl acrylate. In some embodiments, the at least one aromatic (meth)acrylate is 2-phenylethyl acrylate. In some embodiments, the at least one aromatic (meth)acrylate is 2-phenylethyl methacrylate. In some embodiments, the aromatic (meth)acrylate is 3-phenylpropyl acrylate. In some embodiments, the aromatic (meth)acrylate is 4-phenylbutyl acrylate. In some embodiments, the combination thereof is a combination of 2-phenylethyl acrylate and 2-phenylethyl methacrylate. In some embodiments, the combination thereof is a combination of 2-phenylethyl acrylate and 3-phenylpropyl acrylate. In some embodiments, the combination thereof is a combination of 2-phenylethyl methacrylate and 3 phenylpropyl acrylate.

In some embodiments, the at least one aromatic (meth)acrylate has at least one aliphatic group comprising at least one carbon-carbon double bond. In some embodiments, the at least one aromatic (meth)acrylate is cinnamyl (meth)acrylate.

In some embodiments, the reactive monomer mixture of Composition (D) comprises the at least one aromatic (meth)acrylate in amount between about 7 and about 25 weight percent, including about 7, 8, 9, 10, 11, 12, 13, 14, 15, 16, 17, 18, 19, 20, 21, 22, 23, 24, and 25 weight percent, between about 10 and about 20 weight percent, including about 10, 11, 12, 13, 14, 15, 16, 17, 18, 19, and 20 weight percent, or between about 12 and about 15 weight percent, including about 12, 13, 14, and 15 weight percent. In some embodiments, the weight percent of the at least one aromatic (meth)acrylate present in the reactive monomer mixture is calculated excluding a diluent.

In some embodiments, the reactive monomer mixture of Composition (D) does not include an aromatic monomer such as an aromatic (meth)acrylate.

In some embodiments of Composition (D), the at least one cross-linking agent is selected from the group consisting of a non-cycloaliphatic cross-linking agent, a cycloaliphatic cross-linking agent, and any combination thereof. In certain embodiments, the at least one cross-linking agent is a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis (meth)acrylamide, poly(ethylene glycol) di(meth)acrylate, bis(2-hydropropyl (meth)acrylate) terminated polydimethylsiloxanes, and any combination thereof. In more certain embodiments, the non-cycloaliphatic cross-linking agent is ethylene glycol dimethacrylate. In particular embodiments, the at least one cross-linking agent is a cycloaliphatic cross-linking agent comprising a cycloaliphatic group having between one and four cycloaliphatic rings. In yet more particular embodiments, the cycloaliphatic cross-linking agent is tricyclo[5.2.1.0$^{2,6}$]decanedimethanol di(meth)acrylate (e.g., tricyclo[5.2.1.0$^{2,6}$]decanedimethanol diacrylate).

In some embodiments, the reactive monomer mixture of Composition (D) comprises the cross-linking agent in an amount between about 1 and about 20 weight percent, including about 1, 5, 10, 15, and 20 weight percent, between about 3 and about 15 weight percent, including about 3, 4, 5, 6, 7, 8, 9, 10, 11, 12, 13, 14, and 15 weight percent, or between about 3 and about 10 weight percent, including about 3, 4, 5, 6, 7, 8, 9, and 10 weight percent. In some embodiments, the weight percent of the cycloaliphatic cross-linking agent present in the reactive monomer mixture is calculated excluding a diluent.

In some embodiments, the cross-linking agent has formula:

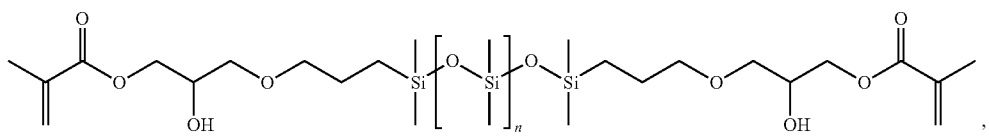

wherein n is an integer from 5 to 50, including 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In some embodiments, n is 15, 16, 17, 18, 19, 20, 21, 22, 23, 24, or 25. In particular embodiments, n is 20. In some embodiments, the reactive monomer mixture comprises the cross-linking agent in an amount of about 15% to about 22% by weight, or between about 16% to about 20% by weight. In particular embodiments, the cross-linking agent is present in the reactive monomer mixture in an amount of about 18% by weight.

In some embodiments of Composition (D), the reactive monomer mixture further comprises a polyamide. In some embodiments, the at least one polyamide is selected from poly(vinyl pyrrolidone), poly(N-vinyl-N-methyl acetamide), poly(N-vinyl acetamide), poly(dimethyl acrylamide), and a copolymer or a mixture thereof. In particular embodiments, the at least one polyamide is selected from poly(vinyl pyrrolidone) and poly(N-vinyl-N-methyl acetamide). In certain embodiments, the at least one polyamide is a copolymer.

In some embodiments, the reactive monomer mixture of Composition (D) comprises the at least one polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the at least one polyamide present in the reactive monomer mixture is calculated excluding a diluent.

In some embodiments, Composition (D) further comprises at least one UV/HEV absorbing compound in the reactive monomer mixture. In some embodiments, the UV/HEV absorbing compound may take the form of Formula II:

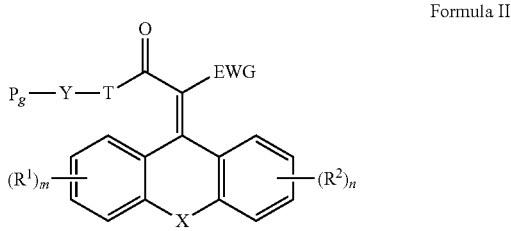

Formula II wherein:
m and n are independently 0, 1, 2, 3, or 4;
T is a bond, O, or NR;
X is O, S, NR, SO, or $SO_2$;
Y is a linking group;
$P_g$ is a polymerizable group;
R at each occurrence is independently H, $C_1$-$C_6$ alkyl, cycloalkyl, heterocycloalkyl, aryl, heteroaryl, or Y—$P_g$;
$R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
EWG is an electron withdrawing group.

Compounds of Formula II preferably contain one or two Y—$P_g$ groups. More preferably, the compounds contain one Y—$P_g$ group.

In certain embodiments, the at least one UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof. In certain embodiments, the at least one UV/HEV absorbing compound is 2-(2-cyano-2-(9H-thioxanthen-9-ylidene)acetamido)ethyl methacrylate. In certain embodiments, the at least one UV/HEV absorbing compound is 3-(3-(tert-butyl)-5-(5-chloro-2H-benzo[d][1,2,3]triazol-2-yl)-4-hydroxyphenyl)propyl methacrylate.

In some embodiments, the reactive monomer mixture of Composition (D) comprises the at least one UV/HEV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV/HEV absorbing compound present in the reactive monomer mixture is calculated excluding a diluent.

In some embodiments, Composition (D) further comprises at least one diluent in the reactive monomer mixture.

In some embodiments, Composition (D) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent, or between about 0.5 and less than 5 weight percent, including 0.5, 1.0, 1.5, 2.0, 2.5, 3.0, 3.5, 4.0, and 4.5 weight percent. In some embodiments, the water content is measured when the material is hydrated at 37° C.

In some embodiments, Composition (D) has a refractive index of at least 1.45 and an Abbe number of at least 45. In other embodiments, Composition (D) has a refractive index of at least 1.48 and an Abbe number of at least 50. In yet other embodiments, Composition (D) has a refractive index of at least 1.50 and an Abbe number of at least 50. In some embodiments, the indicated refractive index and the indicated Abbe number are measured when the material is in a dry state at 25° C.

In some embodiments of Composition (D), the free radical polymerization is a photopolymerization using a bisacylphosphine oxide initiator. In some embodiments, the initiator is bis(2,4,6-trimethylbenzoyl)-phenylphosphineoxide.

(5) Composition (E)

In some embodiments, the presently disclosed subject matter provides a composition, referred to herein as "Composition (E)," made by free radical polymerization of a reactive monomer mixture comprising: (i) at least one hydrophobic monomer; (ii) at least one monomer selected from a hydrophilic monomers hydroxyalkyl (meth)acrylate monomers, and any combinations thereof; and (iii) a tricyclo [5.2.1.0$^{2,6}$]decanedimethanol di(meth)acrylate cross-linking agent; wherein the composition exhibits a refractive index of at least 1.45 and an Abbe number of at least 39.

In some embodiments of Composition (E), the hydrophobic monomer is a hydrophobic (meth)acrylate monomer. In some embodiments, the hydrophobic (meth)acrylate is selected from a cycloaliphatic (meth)acrylate, an aliphatic (meth)acrylate, an aromatic (meth)acrylate, and any combination thereof.

In some embodiments of Composition (E), the hydrophobic (meth)acrylate is a cycloaliphatic (meth)acrylate. In some embodiments, the cycloaliphatic (meth)acrylate comprises a cycloaliphatic group having between one and four cycloaliphatic rings. In some embodiments, the cycloaliphatic group has one cycloaliphatic ring. The cycloaliphatic ring may be a $C_3$-$C_8$ cycloalkyl group, a $C_3$-$C_7$ cycloalkyl group, a $C_4$-$C_7$ cycloalkyl group, or a $C_5$-$C_6$ cycloalkyl group. In some embodiments, the cycloaliphatic (meth) acrylate has at least one cycloaliphatic group comprising at least one carbon-carbon double bond. In some embodiments, the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth)acrylate, isobornyl derivatives, norbornyl derivatives, ((1R, 2S,4R)-bicyclo[2.2.1]hept-5-en-2-yl)methyl (meth)acrylate, ethylene glycol dicyclopentenyl ether (meth)acrylate, poly(ethylene) glycol dicyclopentenyl ether (meth)acrylate, 2,2-bis(cyclopent-1-en-1-yloxy)ethyl (meth)acrylate, 2-(((3aR,4R,5S,7R,7aR)-octahydro-1H-4,7-methanoinden-5-yl)oxy)ethyl acrylate, 2-(((3aS,4R,6S,7R,7aR)-3a,4,5,6,7,7a-hexahydro-1H-4,7-methanoinden-6-yl)oxy)ethyl acrylate, (3aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R,3S,5f,7r)-2-methyladamantan-2-yl (meth)acrylate, (1R,3S,5f,7r)-2-methyladamantan-2-yl PEG (meth)acrylate derivates and (1R,3S,5f,7r)-2-methyladamantan-2-yl (meth)acrylate derivatives, and any combination thereof. In some embodiments, the cycloaliphatic (meth)acrylate is selected from cyclohexyl (meth)acrylate, cyclopentyl (meth)acrylate, cyclohexylmethyl (meth)acrylate, 2-cyclohexylethyl (meth)acrylate, 3-cyclohexylpropyl (meth)acrylate, and any combination thereof. In some embodiments, the cycloaliphatic (meth)acrylate is selected from cyclohexyl acrylate, cyclohexylmethyl acrylate, cyclohexylmethyl methacrylate, 2-cyclohexylethyl acrylate, 2-cyclohexylethyl methacrylate, ethylene glycol dicyclopentenyl ether (meth)acrylate, and any combination thereof. In some embodiments, the cycloaliphatic (meth)acrylate is cyclohexyl acrylate. In some embodiments, the cycloaliphatic (meth)acrylate is cyclohexylmethyl acrylate. In some embodiments, the cycloaliphatic (meth)acrylate is 2-cyclohexylethyl acrylate. In some embodiments, the cycloaliphatic (meth)acrylate is ethylene glycol dicyclopentenyl ether acrylate.

In some embodiments, the cycloaliphatic (meth)acrylate does not include a substituent (e.g., a hydroxy substituent) on the cycloaliphatic moiety or anywhere else on the monomer (e.g., in a monomer such as 2-cyclohexylethyl (meth)acrylate, the monomer does not include a substituent such as a hydroxy substituent on either the cyclohexyl moiety or the ethyl moiety).

In some embodiments, the reactive monomer mixture of Composition (E) comprises the cycloaliphatic (meth)acrylate monomer in an amount between about 40 and about 90 weight percent, including about 40, 45, 50, 55, 60, 65, 70, 75, 80, 85, and 90 weight percent, between about 50 and about 80 weight percent, including about 50, 55, 60, 65, 70, 75, and 80 weight percent, or between about 50 and about 70 weight percent, including about 50, 51, 52, 53, 54, 55, 56, 57, 58, 59, 60, 61, 62, 63, 64, 65, 66, 67, 68, 69, and 70 weight percent. In some embodiments, the weight percent of the cycloaliphatic (meth)acrylate monomer present in the reactive monomer mixture is calculated excluding a diluent.

In particular embodiments, the hydrophobic (meth)acrylate is an aliphatic (meth)acrylate. In some embodiments, the aliphatic (meth)acrylate comprises a linear or branched alkyl group containing between 1 and 18 carbon atoms (a $C_1$-$C_{18}$ alkyl group), including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl (meth)acrylate. In more particular embodiments, the $C_1$-$C_{18}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof. In yet more particular embodiments, the aliphatic (meth)acrylate comprises a linear alkyl group containing between 4 and 8 carbon atoms (a $C_4$-$C_8$ linear alkyl group). In some embodiments, the aliphatic (meth)acrylate is n-hexyl acrylate.

In some embodiments, the reactive monomer mixture of Composition (E) comprises the aliphatic (meth)acrylate in an amount between about 1 and about 20 weight percent, including about 1, 5, 10, 15, and 20 weight percent, or between about 1 and about 10 weight percent, including about 1, 2, 3, 4, 5, 6, 7, 8, 9, and 10 weight percent. In some embodiments, the weight percent of the aliphatic (meth)acrylate present in the reactive monomer mixture is calculated excluding a diluent.

In some embodiments, the hydrophobic (meth)acrylate is an aromatic (meth)acrylate. In some embodiments, the aromatic (meth)acrylate is a (meth)acrylate comprising at least one aryl group. In some embodiments, the aryl group is a phenyl group. In some embodiments, the aryl group can be present in the aromatic (meth)acrylate as part of an arylalkyl group (e.g., benzyl, 2-phenylethyl, 3-phenylpropyl, or 4-phenylbutyl), an aryloxyalkyl group (e.g., phenoxymethyl, 2-phenoxyethyl, or 3-phenoxypropyl), or an arylthioalkyl group (e.g., phenylthiomethyl, 2-phenylthioethyl, or 3-phenylthiopropyl). In some embodiments, the aromatic (meth)acrylate is selected from 2-phenylethyl (meth)acrylate, 2-phenoxyethyl (meth)acrylate, 3-phenylpropyl (meth)acrylate, 4-phenylbutyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is selected from 2-phenylethyl (meth)acrylate, 2-phenoxyethyl (meth)acrylate, 3-phenylpropyl (meth)acrylate, 3 phenoxypropyl (meth)acrylate, 1,3-bis(phenylthio)-2-propyl (meth)acrylate, poly(ethylene glycol) phenyl ether (meth)acrylate, and any combination thereof. In some embodiments, the aromatic (meth)acrylate is 2-phenylethyl acrylate. In some embodiments, the aromatic (meth)acrylate is 2-phenylethyl methacrylate. In some embodiments, the aromatic (meth)acrylate is a combination of 2-phenylethyl acrylate and 2-phenylethyl methacrylate. In some embodiments, the aromatic (meth)acrylate is 3-phenylpropyl acrylate. In some embodiments, the aromatic (meth)acrylate is 4-phenylbutyl acrylate.

In some embodiments, the reactive monomer mixture of Composition (E) comprises the aromatic (meth)acrylate in amount between about 7 and about 25 weight percent, including about 7, 8, 9, 10, 11, 12, 13, 14, 15, 16, 17, 18, 19, 20, 21, 22, 23, 24, and 25 weight percent, between about 10 and about 20 weight percent, including about 10, 11, 12, 13, 14, 15, 16, 17, 18, 19, and 20 weight percent, or between about 12 and about 15 weight percent, including about 12, 13, 14, and 15 weight percent. In some embodiments, the weight percent of aromatic (meth)acrylate present in the reactive monomer mixture is calculated excluding a diluent.

The reactive monomer mixture of Composition (E) comprises at least one hydrophilic monomer. In some embodiments, the reactive monomer mixture of Composition (E) comprises at least one hydrophilic monomer selected from vinyl pyrrolidone, N-vinyl-N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl)acrylamide, N-(2-hydroxyethyl)(meth)acrylamide, N-(2-hydroxypropyl)(meth)acrylamide, N-(3 hydroxypropyl)(meth)acrylamide, poly(ethylene glycol) methyl ether (meth)acrylate, poly(ethylene glycol) (meth)acrylate, and any combination thereof.

In some embodiments, the at least one hydrophilic monomer is a poly(ethylene glycol)-containing monomer. In some embodiments, the poly(ethylene glycol)-containing monomer is selected from poly(ethylene glycol) methyl ether (meth)acrylate and poly(ethylene glycol) (meth)acrylate. In some embodiments, the poly(ethylene glycol)-containing monomer is poly(ethylene glycol) methacrylate. In some embodiments, the poly(ethylene glycol)-containing monomer is poly(ethylene glycol) methyl ether methacrylate. In some embodiments, the reactive monomer mixture of Composition (E) comprises a combination of poly(ethylene glycol) methacrylate and poly(ethylene glycol) methyl ether methacrylate.

In some embodiments, the poly(ethylene glycol)-containing monomer has a number-average molecular weight ($M_n$) of about 200 g/mol to about 1000 g/mol, including 200 g/mol, 220 g/mol, 240 g/mol, 260 g/mol, 280 g/mol, 300 g/mol, 320 g/mol, 340 g/mol, 360 g/mol, 380 g/mol, 400 g/mol, 420 g/mol, 440 g/mol, 460 g/mol, 480 g/mol, 500 g/mol, 520 g/mol, 540 g/mol, 560 g/mol, 580 g/mol, 600 g/mol, 620 g/mol, 640 g/mol, 660 g/mol, 680 g/mol, 700 g/mol, 720 g/mol, 740 g/mol, 760 g/mol, 780 g/mol, 800 g/mol, 820 g/mol, 840 g/mol, 860 g/mol, 880 g/mol, 900 g/mol, 920 g/mol, 940 g/mol, 960 g/mol, 980 g/mol, and 1000 g/mol. In some embodiments, the poly(ethylene glycol)-containing monomer has a number-average molecular weight ($M_n$) of about 200 g/mol to about 400 g/mol, including 200 g/mol, 220 g/mol, 240 g/mol, 260 g/mol, 280 g/mol, 300 g/mol, 320 g/mol, 340 g/mol, 360 g/mol, 380 g/mol, and 400 g/mol.

In some embodiments, the poly(ethylene glycol)-containing monomer has formula:

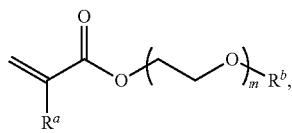

wherein $R^a$ and $R^b$ are each independently selected from hydrogen and methyl, and m is an integer from 2 to 25, including 2, 3, 4, 5, 6, 7, 8, 9, 10, 11, 12, 13, 14, 15, 16, 17, 18, 19, 20, 21, 22, 23, 24, and 25. In some embodiments, $R^a$ is hydrogen. In some embodiments, $R^a$ is methyl. In some embodiments, $R^b$ is hydrogen. In some embodiments, $R^b$ is methyl. In particular embodiments, $R^a$ is methyl and $R^b$ is hydrogen. In some embodiments, $R^a$ is methyl and $R^b$ is methyl. In some embodiments, m is an integer from 2 to 8, including 2, 3, 4, 5, 6, 7, and 8.

In some embodiments, the hydrophilic monomer is selected from 2-hydroxyethyl (meth)acrylate, 2-hydroxypropyl (meth)acrylate, 3-hydroxypropyl (meth)acrylate, 2,3-dihydroxypropyl (meth)acrylate, 4-hydroxybutyl acrylate. In some embodiments, the hydrophilic monomer is selected from 2-hydroxyethyl methacrylate and 4-hydroxybutyl acrylate. In some embodiments, the hydrophilic monomer is 4-hydroxybutyl acrylate.

In some embodiments, the reactive monomer mixture of Composition (D) comprises a combination of a poly(ethylene glycol)-containing monomer and a hydrophilic monomer selected from 2-hydroxyethyl (meth)acrylate, 2-hydroxypropyl (meth)acrylate, 3-hydroxypropyl (meth)acrylate, 2,3-dihydroxypropyl (meth)acrylate, 4-hydroxybutyl acrylate. In some embodiments, the reactive monomer mixture of Composition (D) comprises a combination of a poly(ethylene glycol) (meth)acrylate monomer and 2-hydroxyethyl (meth)acrylate. In some embodiments, the reactive monomer mixture of Composition (D) comprises a combination of poly(ethylene glycol) methacrylate and 2-hydroxyethyl methacrylate. In some embodiments, the reactive monomer mixture of Composition (D) comprises a combination of poly(ethylene glycol) methyl ether methacrylate and 2-hydroxyethyl methacrylate.

In some embodiments, the reactive monomer mixture of Composition (E) comprises the at least one hydrophilic monomer (e.g., the poly(ethylene glycol)-containing monomer) in amount between about 1 and about 40 weight percent, including about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 weight percent, between about 10 and about 30 weight percent, including about 10, 11, 12, 13, 14, 15, 16, 17, 18, 19, 20, 21, 22, 23, 24, 25, 26, 27, 28, 29, and 30 weight percent, between about 12 and about 22 weight percent, including about 12, 13, 14, 15, 16, 17, 18, 19, 20, 21, and 22 weight percent, between about 14 and about 20 weight percent, including about 14, 15, 16, 17, 18, 19, and 20 weight percent, between about 1 and about 10 weight percent, including about 1, 2, 3, 4, 5, 6, 7, 8, 9, and 10 weight percent, between about 2 and about 8 weight percent, including about 2, 3, 4, 5, 6, 7, and 8 weight percent, or between about 4 and about 6 weight percent, including about 4, 5, and 6 weight percent. In some embodiments, the weight percent of the at least one hydrophilic monomer (e.g., the poly(ethylene glycol)-containing monomer) present in the reactive monomer mixture is calculated excluding a diluent.

In some embodiments, the tricyclo[5.2.1.0$^{2,6}$]decanedimethanol di(meth)acrylate cross-linking agent is tricyclo[5.2.1.0$^{2,6}$]decanedimethanol diacrylate.

In some embodiments, the reactive monomer mixture of Composition (E) comprises the tricyclo[5.2.1.0$^{2,6}$]decanedimethanol di(meth)acrylate cross-linking agent (e.g., tricyclo[5.2.1.0$^{2,6}$]decanedimethanol diacrylate) in an amount between about 1 and about 20 weight percent, including about 1, 5, 10, 15, and 20 weight percent, between about 3 and about 15 weight percent, including 3, 4, 5, 6, 7, 8, 9, 10, 11, 12, 13, 14, and 15, or between about 3 and about 10 weight percent, including 3, 4, 5, 6, 7, 8, 9, and 10 weight percent. In some embodiments, the weight percent of the tricyclo[5.2.1.0$^{2,6}$]decanedimethanol di(meth)acrylate cross-linking agent present in the reactive monomer mixture is calculated excluding a diluent.

In some embodiments, the reactive monomer mixture of Composition (E) comprises: (i) ethylene glycol dicyclopentenyl ether acrylate; (ii) a hydrophilic monomer selected from the group consisting of poly(ethylene glycol) methacrylate, poly(ethylene glycol) methyl ether methacrylate, 2-hydroxyethyl methacrylate, and any combination thereof; and (iii) a tricyclo[5.2.1.0$^{2,6}$]decanedimethanol diacrylate cross-linking agent; wherein the composition exhibits a refractive index of at least 1.45 and an Abbe number of at least 39.

In some embodiments of Composition (E), the reactive monomer mixture further comprises a polyamide. In some embodiments, the at least one polyamide is selected from poly(vinyl pyrrolidone), poly(N-vinyl-N-methyl acetamide), poly(N-vinyl acetamide), poly(dimethyl acrylamide), and a copolymer or a mixture thereof. In particular embodiments, the at least one polyamide is selected from poly(vinyl pyrrolidone) and poly(N-vinyl-N-methyl acetamide). In certain embodiments, the at least one polyamide is a copolymer.

In some embodiments, the reactive monomer mixture of Composition (E) comprises the at least one polyamide in an amount between about 0.1 weight percent and about 5 weight percent, including about 0.1, 0.5, 1, 2, 3, 4, and 5 weight percent, between about 0.5 weight percent and about 3 weight percent, including about 0.5, 1, 2, and 3 weight percent, or between about 0.5 weight percent and about 2 weight percent, including about 0.5, 1, and 2 weight percent. In some embodiments, the weight percent of the at least one polyamide present in the reactive monomer mixture is calculated excluding a diluent.

In some embodiments, Composition (E) further comprises at least one UV/HEV absorbing compound in the reactive monomer mixture. In some embodiments, the UV/HEV absorbing compound may take the form of Formula II:

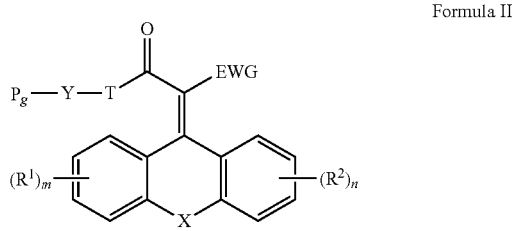

Formula II wherein:
   m and n are independently 0, 1, 2, 3, or 4;
   T is a bond, O, or NR;
   X is O, S, NR, SO, or $SO_2$;
   Y is a linking group;
   $P_g$ is a polymerizable group;
   R at each occurrence is independently H, $C_1$-$C_6$ alkyl, cycloalkyl, heterocycloalkyl, aryl, heteroaryl, or Y—$P_g$;
   $R^1$ and $R^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl (preferably unsubstituted phenyl or phenyl substituted with alkyl or halo), halo, hydroxy, amino, $NR^3R^4$, or benzyl, wherein $R^3$ and $R^4$ are independently H or $C_1$-$C_6$ alkyl, or two adjacent $R^1$ or $R^2$ groups, together with the carbon atoms to which they are attached, combine to form a cycloalkyl or aryl ring; and
   EWG is an electron withdrawing group.

Compounds of Formula II preferably contain one or two Y—$P_g$ groups. More preferably, the compounds contain one Y—$P_g$ group.

In certain embodiments, the at least one UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof. In certain embodiments, the at least one UV/HEV absorbing compound is 2-(2-cyano-2-(9H-thioxanthen-9-ylidene)acetamido)ethyl methacrylate. In certain embodiments, the at least one UV/HEV absorbing compound is 3-(3-(tert-butyl)-5-(5-chloro-2H-benzo[d][1,2,3]triazol-2-yl)-4-hydroxyphenyl)propyl methacrylate.

In some embodiments, the reactive monomer mixture of Composition (E) comprises the at least one UV/HEV absorbing compound in an amount between about 0.1 and about 5 weight percent, including about 0.1, 0.5, 1, 2, 3, 4, and 5 weight percent, between about 1 and about 4 weight percent, including about 1, 2, 3, and 4 weight percent, or between about 1 and about 3 weight percent, including about 1, 2, and 3 weight percent. In some embodiments, the weight percent of the at least one UV/HEV absorbing compound present in the reactive monomer mixture is calculated excluding a diluent.

In some embodiments, Composition (E) further comprises at least one diluent in the reactive monomer mixture.

In some embodiments, Composition (E) has a water content of between about 0 weight percent and about 15 weight percent, including about 0, 0.1, 0.5, 1, 2, 3, 4, 5, 6, 7, 8, 9, 10, 11, 12, 13, 14, and 15 weight percent, between about 1 weight percent and about 10 weight percent, including about 1, 2, 3, 4, 5, 6, 7, 8, 9, and 10 weight percent, or between about 1 weight percent and about 8 weight percent, including about 1, 2, 3, 4, 5, 6, 7, and 8 weight percent, or between about 0.5 and less than 5 weight percent, including 0.5, 1.0, 1.5, 2.0, 2.5, 3.0, 3.5, 4.0, and 4.5 weight percent. In some embodiments, the water content is measured when the material is hydrated at 37° C.

In some embodiments, Composition (E) has a refractive index of at least 1.45 and an Abbe number of at least 45. In other embodiments, Composition (E) has a refractive index of at least 1.48 and an Abbe number of at least 50. In yet other embodiments, Composition (E) has a refractive index of at least 1.50 and an Abbe number of at least 50. In some embodiments, the indicated refractive index and the indicated Abbe number are measured when the material is in a dry state at 25° C.

In some embodiments of Composition (E), the free radical polymerization is a photopolymerization using a bisacylphosphine oxide initiator. In some embodiments, the initiator is bis(2,4,6-trimethylbenzoyl)-phenylphosphineoxide.

C. Ophthalmic Devices

In some embodiments, the presently disclosed subject matter provides a device comprising a Composition (A, B, C, D, or E) as described immediately hereinabove.

In particular embodiments, the ophthalmic device comprises a lens, inlay, outlay, or insert selected from an intraocular implant or lens, a contact lens, a corneal inlay, a corneal outlay, and a corneal insert.

In specific embodiments, the ophthalmic device is an intraocular implant or lens. More specifically, the presently disclosed subject matter also provides intraocular implants and/or lenses made at least partially or completely from the compositions (A-E) described herein. Such intraocular implants or lenses can include an optic portion and one or more haptic portions. Typically, the compositions of the presently disclosed subject matter will make up part or all of the optic portion of the intraocular implant or lens. In some embodiments, the optic portion of the implant or lens will have a core made from one of the compositions described herein surrounded by different polymer or material. Implants or lenses in which the optic portion is made up of at least partially of one of the compositions of the presently disclosed subject matter will usually also have a haptic portion. The haptic portion can also be made of polymer of the disclosure or can be made of a different material, for example another polymer.

In some embodiments, the intraocular implant or lens of the presently disclosed subject matter is a one-piece lens having a soft, foldable central optic region and an outer peripheral region (haptic-region) in which both regions are made of the same polymer. In other embodiments, the optic and haptic regions can be formed from different types of polymers or materials, if desired. Some implants or lenses can also have haptic portions that are made up of different materials, for example where one or more haptic portions is made from the same material as the optic portion and other haptic portions are made of materials other than a polymer of the disclosure. Multicomponent implants or lenses can be made by embedding one material in the other, concurrent extrusion processes, solidifying the hard material about the soft material, or forming an interpenetrating network of the rigid component into a preformed hydrophobic core. In instances where one or more haptic portions are made from a different material than the optic portion of the lens, the haptic portion can be attached to the optic portion in any manner known in the art, such as by drilling a hole or holes in the optic portion and inserting the haptic portion.

The compositions described herein have been designed so that they are capable of being folded so that the intraocular lens can be inserted into the eye of an individual through a small incision. In some instances that incision will be less than 2.5 mm; in some instances that incision will be less than 2 mm. The haptic portion of the lens provides the required support for the implant or lens in the eye after insertion and unfolding of the lens and tends to help stabilize the position of the lens after insertion and the closure of the incision. The shape of the haptic portion design is not particularly limited and can be any desired configuration, for example, either a plate type or graduated thickness spiral filaments, also known as a C-loop design.

The optic portion of the intraocular lens can be approximately 2-6 mm in diameter prior to hydration. The 2-6 mm diameter is fairly standard in the art and is generally chosen to cover the pupil in its fully dilated state under naturally occurring conditions. However, other sizes are contemplated and the presently disclosed subject matter is not limited to any particular diameter or size of intraocular lens. Furthermore, it is not necessary that the lens optic portion be circular; it could also be oval, square, or any other shape as desired.

The intraocular lens can further include one or more non-optical haptic components extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Should the intraocular lens include other components besides the optical and haptic portions, such other portions can be made of a polymer as are the haptic and optic portions, or if desired, another material.

The intraocular implants lenses may be inserted into the eye in any manner known in the art. For example, the intraocular lens may be folded prior to insertion into the eye using an intraocular lens inserter or by small, thin forceps of the type typically used by ophthalmic surgeons. After the implant or lens is in the targeted location, it is released to unfold. As is well known in the art, typically the lens that is to be replaced is removed prior to insertion of the intraocular lens. The intraocular lens of the presently disclosed subject matter can be made of a generally physiologically inert soft polymeric material that is capable of providing a clear, transparent, refractive lens body even after folding and unfolding. In some embodiments, the foldable intraocular lens of the presently disclosed subject matter can be inserted into any eye by injection whereby the mechanically compliant material is folded and forced through a small tube such as a 1 mm to 3 mm inner diameter tube.

E. Method for Making an Ophthalmic Device

In still yet other embodiments, the presently disclosed subject matter provides a method for making an ophthalmic device, the method comprising: (a) providing any one of Composition (A), Composition (B), Composition (C), Composition (D), or Composition (E); and (b) forming an ophthalmic device. In other embodiments, the presently disclosed subject matter provides a method for making an ophthalmic device, the method comprising: (a) preparing a blank from any one of Composition (A), Composition (B), Composition (C), Composition (D), or Composition (E); and (b) machining an ophthalmic device from the blank. In still other embodiments, the presently disclosed subject matter provides a method for making an ophthalmic device, the method comprising molding an ophthalmic device from any one of Composition (A), Composition (B), Composition (C), Composition (D), or Composition (E). In still other embodiments, the presently disclosed subject matter provides a method for making an ophthalmic device, the method comprising molding an ophthalmic device from any one of Composition (A), Composition (B), Composition (C), Composition (D), or Composition (E), and then refining the surface via lathing. In certain embodiments of the above methods, the method further comprises the step of extracting the ophthalmic device with a solvent. In certain embodiments, the method further comprises the step of hydrating the extracted ophthalmic device with at least one aqueous solution. In particular embodiments, the method further comprises an irradiation step using a laser, which in certain embodiments, is a two photon laser, which in more certain embodiments, is a femtosecond two photon laser. In more particular embodiments, the method further comprises a step of sterilizing the ophthalmic device. The ophthalmic device may be sterilized by known means such as, but not limited to, autoclaving.

Some embodiments of the disclosure will now be described in detail in the following Examples.

EXAMPLES

Unless otherwise noted, test samples for refractive index, Abbe number, water content and glass transition temperature were polymer buttons that had been extracted with acetonitrile or 2-propanol and dried. Unless otherwise noted, test samples for micro-glistening and macro-glistening testing were lenses.

Refractive Index Test Method: Refractive index was measured using an Anton Paar Abbemat WR-wavelength refractometer. The instrument was equilibrated at either 25° C. or 35° C. for a minimum of 1 hour prior to use. The measurement wavelength was set at 589.3 nanometers. Using a pair of tweezers, the sample was placed on the quartz plate. The instrument lid was closed, and the refractive index was recorded after 60 seconds of dwell time. Measurements were performed on three polymer buttons, and the average was reported. In some examples, where it is noted, measurements were performed on both sides of the three polymer buttons, and the average of the six measurements was reported.

Abbe Number Test Method: Following the steps for measuring the refractive index at 589.3 nm, the refractive index at 486.1 nm and 656.3 nm were determined. Measurements were performed on three polymer buttons, and for each polymer button, the refractive index measurements at all three wavelengths were completed before measuring the next replicate. The Abbe number was calculated as follows:

$$V_D = \frac{n_D - 1}{n_F - n_C};$$

where $n_D$, $n_F$ and $n_C$ are the refractive indices of the material at the wavelengths of the Fraunhofer D-, F- and C-spectral lines (589.3 nm, 486.1 nm and 656.3 nm respectively). The average of the three measurements was reported. In some examples, where it is noted, measurements were performed on both sides of the three polymer buttons, and the average of the six measurements was reported.

As noted in the examples, the water content was measured gravimetrically by either a "Drying Method" or by a "Hydration Method."

In the "Drying Method," three polymer buttons (each about 2 millimeters in thickness and 13 millimeters in diameter) were equilibrated in individual glass scintillation vials containing about 10 mL PBS for about 14 days at 37° C. Each polymer button was removed from the vial using a sharp-tipped metal tweezers and briefly blotted on all sides (flat surfaces and edge) using lint-free blotting paper to remove surface/excess PBS. Using dry tweezers, each button was placed in a tared weighing pan and weighed individually. The wet weight of each polymer button is defined as the combined weight of the pan and wet button minus the weight of the weighing pan alone. The dry weight was measured by placing the sample pans in a vacuum oven which has been preheated to 60° C. for 30 minutes. Vacuum was applied until the pressure reached at least 1 inch of Hg (mercury); lower pressures were allowed. The vacuum valve and pump were turned off, and the lenses were dried for 24 hours. The purge valve was opened allowing dry air or dry nitrogen gas to enter. Once the oven reached atmospheric pressure, then the pans were removed and weighed. After weighing the pans (with polymer buttons), the polymer buttons were placed in the vacuum oven and dried for an additional 24 hours and subsequently weighed to provide data at 48 hours of drying. This procedure was repeated to generate data at 72 hours of drying. At each time point, the dry weight is defined as the combined weight of the pan and dry button minus the weight of the weighing pan alone. The water content of the polymer button was calculated as follows: percent water content (% WC)=(wet weight−dry weight)/wet weight×100. The average and standard deviation of the water content were calculated, and the average value reported as the percent water content of the button.

Alternatively, water content was determined gravimetrically by a "Hydration Method." In this method, three dry polymer buttons (previously extracted exhaustively with 2-propanol and dried) were individually weighed and transferred to individual glass scintillation vials using sharp-tipped metal tweezers. About 10 mL of de-ionized water was transferred into each vial, and the samples were incubated at 37° C. for 7 days. After incubation, the polymer buttons were removed from the vials using a sharp-tipped metal tweezers and briefly blotted on all sides (flat surfaces and edge) using lint-free blotting paper to remove surface/excess water. Using a dry tweezers, each polymer button was placed in a tared weighing pan and weighed individually. After weighing, the polymer buttons were transferred back into the vials and incubated at 37° C. for 7 additional days to determine the water content at 14 days. At each time point, the water content of the polymer button was calculated as follows: (% WC)=(wet weight−dry weight)/wet weight×100.

Glass Transition Temperature Test Method: Because of the thickness and/or brittleness of the polymer buttons, test samples were cut from the center of the polymer buttons or lenses using a razor blade. The samples could not be punched out as with a thin film. Test samples were analyzed (in duplicate) on a DSC Q2000 TA instrument at heating rates of 10° C./minute and cooling rates of 5° C./minute under a nitrogen gas atmosphere. The glass transition temperatures were determined from the first and second heating scans ($1^{st}$ scan and $2^{nd}$ scan, respectively).

Micro-Glistening Test Method: Prior to conditioning lenses for dark field light microscopy, lenses were extracted in acetonitrile or methanol. For the extraction, lenses were placed individually into lens cases containing 3 mL of acetonitrile or methanol and extracted overnight at ambient temperature, followed by 3 exchanges of 3 mL aliquots of acetonitrile or methanol at 4 hours interval. After the final extraction, lenses were air dried at ambient temperature for at least six days. Lenses were subsequently cleaned to remove any noticeable residual debris from their fabrication and extraction processes, and then immersed in 0.9% saline solution in fluid cells. Microvacuoles may be induced by placing these cells into an oven at 35° C. for a period of about 15 hours. The lenses were removed from the oven and equilibrated at room temperature for at least 2 hours before being analyzed by dark field light microscopy as described in Biomedical Optics Express, 2013, Vol. 4 No. 8, which is incorporated herein by reference in its entirety. Any standard light microscope or camera capable of dark field imaging may be used. Under dark field settings, the intraocular lens is retro-illuminated with an annulus of light under an oblique angle. If there are no microvacuoles or other light scattering centers, the image is black. As the number of microvacuoles increases, the amount of forward scattered light increases, creating a constellation pattern of forward scattered light on a dark background. The Image J program (or another similar post-image processing software program) was used to determine the density of the microvacuoles from dark field microscopy photographs for small populations of microvacuoles. A circular area with a diameter of 4 millimeter was examined, and the density of microvacuoles calculated (number of microvacuoles or micro-glistenings per millimeter$^2$ (#/mm$^2$)). Generally speaking, intraocular lenses with fewer microvacuoles or micro-glistenings provide better vision than ones with more forward scattering and therefore are preferred. Micro-glistening densities of approximately 4/mm$^2$ are considered low and comparable with intraocular lenses not associated with any glistenings.

Macro-Glistening Test Method: Lenses were placed individually into lens cases containing 3 mL of acetonitrile (ACN). Lenses were extracted at ambient temperature for four hours. The acetonitrile was removed with a disposable pipet, and another 3 mL of acetonitrile was added. The lenses were then extracted overnight at ambient temperature. The acetonitrile was removed with a disposable pipet, and another 3 mL of acetonitrile was added. Lenses were extracted at ambient temperature for four hours. The acetonitrile was removed with a disposable pipet, and another 3 mL of acetonitrile was added. Lenses were extracted at ambient temperature for four hours. The acetonitrile was removed with a disposable pipet, and lenses were air dried at ambient temperature for at least six days. The air-dried lenses were placed individually into lens cases containing 3 mL of methanol and equilibrated at ambient temperature overnight. Alternatively, lenses were initially extracted directly with 3 mL aliquots of methanol overnight, followed by 3 exchanges of 3 mL aliquots of methanol at 4 hours interval. After organic extraction by either method, the lenses were subsequently stepped down into DPBS solution by the following "gradient equilibration" procedure: (1) lenses were placed individually into lens cases containing 3 mL of 80% (v/v) aqueous methanol at ambient temperature for four hours, (2) the 80% (v/v) aqueous methanol was then replaced with 3 mL of 60% (v/v) aqueous methanol at ambient temperature for four hours, (3) the 60% (v/v) aqueous methanol lenses was then replaced with 3 mL of 50% (v/v) methanol:DPBS at ambient temperature overnight, (4) the 50% (v/v) methanol:DPBS was then replaced with 3 mL of 40% (v/v) methanol:DPBS at ambient temperature for four hours, (5) the 40% (v/v) methanol:DPBS was then replaced with 3 mL of 20% (v/v) methanol:DPBS at ambient temperature for four hours, and finally (6) the 20% (v/v) methanol:DPBS was replaced with 3 mL of DPBS at ambient temperature overnight, after at least two rinsing steps with 3 mL of DPBS to remove methanol before equilibrating in DPBS overnight. Vacuoles which scatter light were created in test lenses (as fabricated without extraction, after acetonitrile extraction followed by drying only, or after organic extraction and gradient equilibration) by placing the test lenses individually in lens cases containing 3 mL of PBS. After screwing on the caps, the cases were placed in an incubator at 37° C. for at least three days. Thereafter, the lenses were evaluated by darkfield microscopy using a (Nikon SMZ1500) microscope at 25×-30× magnification. When the number of macro-glistenings is small, they can be counted.

The following abbreviations will be used throughout the Examples and have the following meanings:

TL03 lights: Phillips TLK 40W/03 bulbs
LED: light emitting diode
RMM: reactive monomer mixture(s)
RI (25): refractive index measured at 25° C.
RI (35): refractive index measured at 35° C.
Abbe #(25): Abbe number measured at 25° C.
Abbe #(35): Abbe number measured at 35° C.
$T_g$: glass transition temperature (° C.) as determined by differential scanning calorimetry (DSC)
mm: millimeter(s)
cm: centimeter(s)
μm: micrometer(s)
nm: nanometer(s)
μL: microliter(s)
mW: milliwatt(s)
g/mol: grams/mole
Da or Dalton(s): gram(s)/mole
kDa: kilodalton(s)
PBS: phosphate buffered saline
DPBS: Dulbecco phosphate buffered saline which contains no calcium or magnesium ions
ACN: acetonitrile
CHA: cyclohexyl acrylate [CAS 3066-71-5] (TCI or Alfa Aesar)
EGDCA: Ethylene glycol dicyclopentenyl ether acrylate [CAS 65983-31-5] (Sigma-Aldrich)

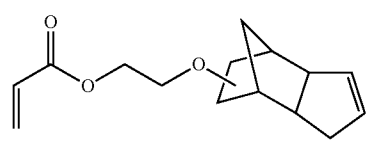

BCHA: ((1R,2S,4R)-bicyclo[2.2.1]hept-5-en-2-yl)methyl acrylate or cyclol acrylate or [(1S,4S)-2-bicyclo[2.2.1] hept-5-enyl]methyl prop-2-enoate [CAS 95-39-6] (Monomer-Polymer and DAJAC Labs Inc.)

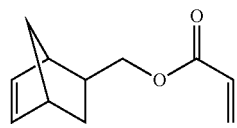

CAA: cinnamyl acrylate

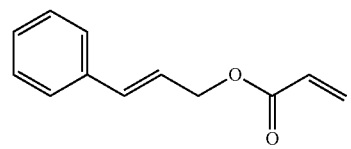

NHA: n-hexyl acrylate [CAS 2499-95-8] (Sigma-Aldrich)
PEA: 2-phenylethyl acrylate [CAS 3530-36-7] (MPD)
PEMA: 2-phenylethyl methacrylate [CAS 3683-12-3]
PPA: 3-phenylpropyl acrylate [CAS 85909-41-7]
TCDA: Tricyclo[5.2.1.0$^{2,6}$]decanedimethanol diacrylate or dimethylol tricyclo decane diacrylate [CAS 42594-17-2] (Sigma-Aldrich or Kyoeisha Chemical Co.)

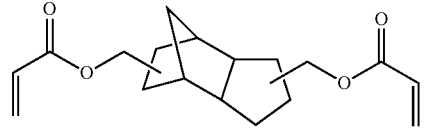

DMA: N, N-dimethylacrylamide [CAS 2680-03-7] (TCI or Sigma-Aldrich)
NVP: N-vinylpyrrolidin-2-one
HEMA: 2-hydroxyethyl methacrylate (Bimax)
HBA: 4-hydroxybutyl acrylate [CAS 2478-10-6] (TCI or BASF)
mPEG 300: poly(ethylene glycol) methyl ether methacrylate ($M_n$=300 grams/mole) (Sigma-Aldrich)

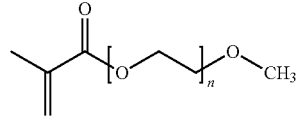

PEG-OH 200: poly(ethylene glycol) methacrylate (Polysciences; molecular weight of the PEG block is 200 grams/mole)
PEG-OH 360: poly(ethylene glycol) methacrylate ($M_n$=360 grams/mole) (Sigma-Aldrich)

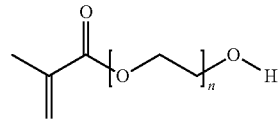

PVP K90: poly(N-vinylpyrrolidone) [CAS 9003-39-8] (Ashland)
PDMA: polydimethylacrylamide ($M_n$=414 kDa; $M_w$=498 kDa; Toray)

The molecular weight was determined by Size Exclusion Chromatography with Multi-Angle Light Scattering (SEC-MALS). The SEC-MALS setup employed aqueous acetonitrile solution as the mobile phase composed of 80% (v/v) 50 mM $Na_2SO_4$ and 20% (v/v) acetonitrile at a flow rate of 0.5 mL/min at 40° C. Two Tosoh Biosciences TSK-gel columns in series were used [SuperAW4000 and SuperAW5000] with an online Agilent 1200 UV/VIS diode array detector, a Wyatt Optilab rEX interferometric refractometer, and a Wyatt mini-DAWN Treos multiangle laser scattering (MALS) detector ($\lambda$=658 nm). Absolute molecular weights and polydispersity data were calculated using the Wyatt ASTRA VI SEC/LS software package. About 40 milligrams of PDMA were dissolved in packing solution in a 10 mL volumetric flask. Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask. Three different solutions were prepared and tested. Monomeric serum albumin samples were also tested using solutions made from only 10 milligrams of protein in 10 mL of packing solution. All solutions were filtered through a 0.45-micron nylon membrane filter prior to injection into the SEC-MALS system. The number average molecular weight of the three samples was 414 kDa (standard deviation 12 kDa); the weight average molecular weight of the three samples was 498 kDa (standard deviation 11 kDa); resulting in a polydispersity index of 1.2.

- Omnirad 819: bis(2,4,6-trimethylbenzoyl)-phenylphosphineoxide [CAS 162881-26-7] (IGM Resins)
- AIBN: azobisisobutyronitrile [CAS 78-67-1]
- mPDMS: mono-n-butyl terminated monomethacryloxypropyl terminated polydimethylsiloxane ($M_n$=500-1500 Daltons) (Gelest)
- SiMAA: 2-propenoic acid, 2-methyl-2-hydroxy-3-[3-[1,3,3,3-tetramethyl-1-[(trimethylsilyl)oxy]disiloxanyl]propoxy]propyl ester (Toray) or 3-(3-(1,1,1,3,5,5,5 heptamethyltrisiloxan-3-yl)propoxy)-2-hydroxypropyl methacrylate
- HO-mPDMS: mono-n-butyl terminated mono-(2-hydroxy-3-methacryloxypropyloxy)-propyl terminated polydimethylsiloxane ($M_n$=1400 Daltons, n=15) (Ortec or DSM-Polymer Technology Group)

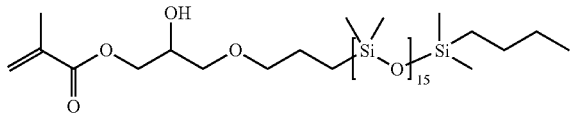

- EGDMA: ethylene glycol dimethacrylate (Esstech)
- ac-PDMS: bis-3-acryloxy-2-hydroxypropyloxypropyl polydimethylsiloxane (Tegomer V-Si 2250 from Evonik)
- XLMA: bis-3-methacryloxy-2-hydroxypropyloxypropyl polydimethylsiloxane ($M_n$=2000 Daltons, n=20) (Shin Etsu)

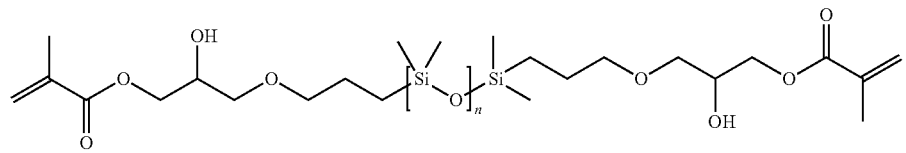

- UV-HEV or UV/HEV: ultraviolet and/or high energy visible light
- UVB: 3-(3-(tert-butyl)-5-(5-chloro-2H-benzo[d][1,2,3]triazol-2-yl)-4-hydroxyphenyl)propyl methacrylate or 2-Methylacrylic acid, 3-[3-tert-butyl-5-(5-chlorobenzotriazol-2-yl)-4-hydroxyphenyl]-propyl ester (Adesis)

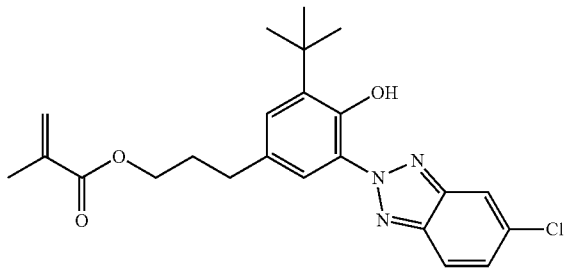 [SMILES: C=C(C)C(=O)OCCCc1cc(-n2nc3ccc(Cl)cc3n2)c(O)c(C(C)(C)C)c1]

- HEVB: 2-(2-cyano-2-(9H-thioxanthen-9-ylidene)acetamido)ethyl methacrylate

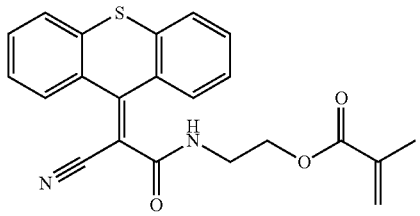 [SMILES: C=C(C)C(=O)OCCNC(=O)C(C#N)=C1c2ccccc2Sc2ccccc21]

Preparation of HEVB: The synthesis of 2-(2-cyano-2-(9H-thioxanthen-9-ylidene)acetamido)-ethyl methacrylate (B) is shown in Scheme 1.

Scheme 1:

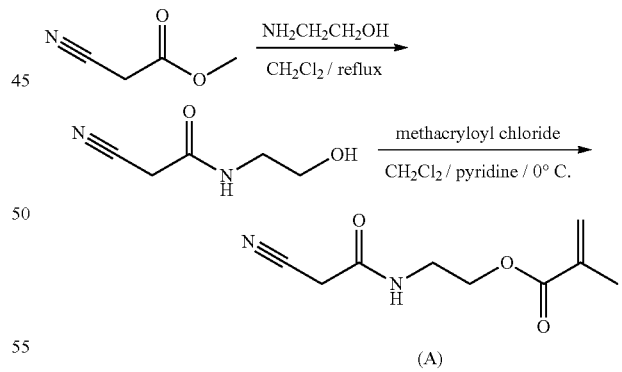

(A)

-continued

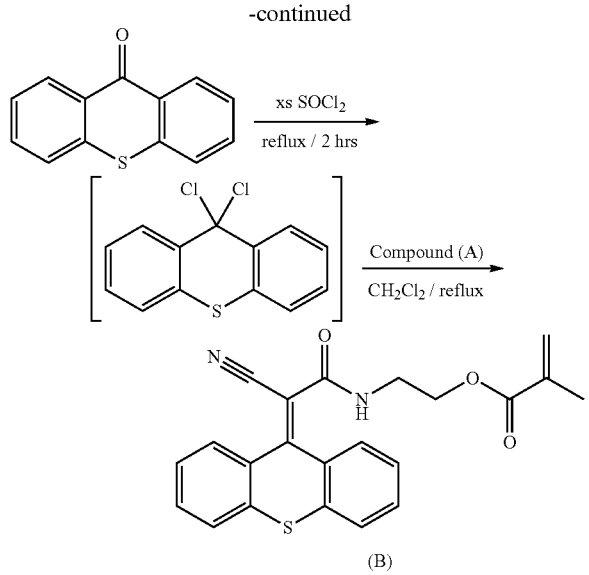

Methyl cyanoacetate (40 grams, 0.4037 mole) and 25 mL of dichloromethane were stirred in a 3 neck, 500 mL round bottom flask under equipped with a reflux condenser under a nitrogen environment. 2-aminoethanol (23.8 grams, 0.3897 mole, ~0.97 eq.) was added to the solution via an addition funnel, after which the temperature rose and the methylene chloride began to reflux. After the exotherm ceased, external heat was applied to continue a gentle reflux for a total of two hours, after which no ethanolamine was observed by thin layer chromatography.

The reaction may also be conducted at room temperature and is complete within a few hours.

The mixture was cooled to room temperature and all the methylene chloride was evaporated at reduced pressure. The residual oil was washed three times with 50 mL of ethyl acetate to remove unreacted starting material and non-polar impurities. The residual ethyl acetate was then removed under reduced pressure, and the resulting oil was used for acylation without any further purification.

The crude N-2-hydroxyethylacetamide derivative was dissolved in 150 mL of dichloromethane containing 40 grams of pyridine (~0.5 mole) in a three-neck round bottom flask equipped with a reflux condenser, an addition funnel, and a magnetic stirring bar. The flask was immersed in an ice bath and allowed to cool down to around 0° C. Methacryloyl chloride (45.76 grams, ~0.44 mole) was added dropwise from the addition funnel, and the resulting reaction mixture was allowed to warm up to room temperature while constantly stirring the system. Methanol (20 mL) was the added to the flask to quench any unreacted methacryloyl chloride. The volatile components were removed by rotary evaporation under reduced pressure, and the crude product dissolved in 800 mL of dilute aqueous HCl. The resulting aqueous solution was extracted three times with 100 mL of hexanes in a separatory funnel to remove any non-polar impurities. The organic layers were discarded. Sodium chloride was added to the aqueous layer which was then extracted three times with 300 mL of ethyl acetate. About 50 milligrams of BHT were added to the combined organic fractions as an inhibitor, and the ethyl acetate removed by rotary evaporation under reduced pressure. The crude product crystalized out of solution during solvent removal. When about 100 mL of ethyl acetate was left in the flask, 250 mL of hexanes was added, and the crude product was isolated by vacuum filtration using a fritted glass funnel. Thin layer chromatography indicated the presence of a single compound. The filter cake was washed two times with 150 mL of hexanes and then vacuum dried at 40° C., yielding 53 grams (about 70% yield) of 2-(2-cyanoacetamido)ethyl methacrylate (A). $^1$H NMR (500 MHz, CDCl$_3$) δ 1.93 (3H, s, CH$_3$), 3.36 (2H, s, CNCH$_2$), 3.60 (2H, dd, CH$_2$NH), 4.26 (2H, t, CH$_2$OC=O), 5.59 (1H, m, vinylic), 6.11 (1H, bs, vinylic), 6.52 (1H, bs, NH).

A mixture of 9H-thioxanthene-9-one (2.12 grams, 0.01 mole) and thionyl chloride (5 mL, 8.2 grams, ~0.07 mole) was refluxed in a 50 mL round bottom flask under a nitrogen atmosphere with constant stirring. After two hours, the red solution was evaporated to dryness ensuring that all unreacted thionyl chloride was removed from the system. 2-(2-Cyanoacetamido)ethyl methacrylate (A) (2.3 grams, 0.0117 mole, ~1.17 eq.) and 15 mL of dichloromethane were added, and the resulting reaction mixture was heated to reflux under a nitrogen blanket. The reaction was monitored by thin layer chromatography. After two hours, no changes were observed in the chromatogram, so the reactive mixture was allowed to cool down to room temperature. 2-(2-cyano-2-(9H-thioxanthen-9-ylidene)acetamido)ethyl methacrylate (B) was isolated as yellow crystals (3.2 grams, 82% yield) after passing through a short silica gel column (CH$_2$C$_{12}$, followed by 8 weight % EtOAc in CH$_2$Cl$_2$). $^1$H NMR (500 MHz, CDCl$_3$) δ 1.84 (3H, s, CH$_3$), 3.47 (2H, m, CH$_2$NH), 4.01 (2H, t, CH$_2$OC=O), 5.55 (1H, m, vinylic), 5.91 (1H, bs, NH), 5.98 (1H, bs, vinylic), 7.24 (1H, t, Ar—H), 7.31 (1H, t, Ar—H), 7.39 (2H, m, Ar—H), 7.49 (1H, d, Ar—H), 7.55 (1H, m, Ar—H), 7.61 (1H, d, Ar—H), 8.04 (1H, m, Ar—H).

CHMA: Cyclohexylmethyl Acrylate

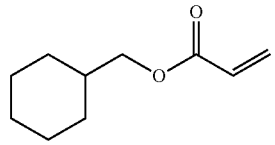

CHEA: 2-Cyclohexylethyl Acrylate

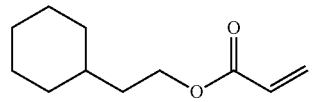

CHPA: 3-Cyclohexylpropyl Acrylate

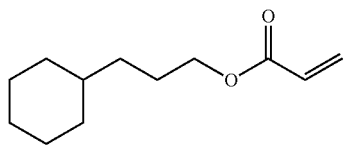

Synthesis of Cyclohexylmethyl Acrylate (CHMA): Cyclohexyl methanol (25.0 g, 219.0 mmol) and triethyl amine (33.46 g, 330.7 mmol) were dissolved in dichloromethane (450 mL) and cooled to about 0° C.; using an ice bath. Acryloyl chloride (29.74 g, 328.5 mmol) was added over a period of 20 minutes while maintaining a constant temperature of about 0° C. After the addition was complete, the reaction mixture was stirred at 0° C. for 30 minutes followed by stirring at ambient temperature overnight. Thin layer chromatography was used to monitor the progress of the reaction. When the reaction was complete, triethyl ammonium chloride was filtered off; dissolved in deionized water (200 mL) and extracted with dichloromethane (3×50 mL). The combined filtrate and organic extracts were washed with water (2×50 mL), brine (25 mL), dried over anhydrous $Na_2SO_4$, vacuum filtered, and concentrated by rotary evaporation. The crude product was then passed through a short plug of silica gel, eluting with 10% ethyl acetate in n-hexanes, to afford the desired product CHMA as a clear oil (98% yield). $^1$H-NMR (500 MHz, $CDCl_3$): δ 6.39 (1H, dd, J=1.0, 17.0 Hz), 6.12 (1H, dd, J=10.0, 17.0 Hz), 5.81 (1H, dd, J=1.5, 10.0 Hz), 3.97 (2H, d, J=6.0 Hz), 1.76-1.62 (6H, m), 1.31-1.15 (3H, m), 0.95-1.01 (2H, m).

Synthesis of 2-Cyclohexylethyl Acrylate (CHEA): 2-Cyclohexylethyl acrylate was prepared by the same general procedure except that 2-cyclohexyl ethanol was used instead of cyclohexyl methanol (99% yield). $^1$H-NMR (500 MHz, $CDCl_3$): δ 6.38 (1H, dd, J=1.1, 17.2 Hz), 6.11 (1H, dd, J=10.1, 17.2 Hz), 5.80 (1H, dd, J=1.4, 10.1 Hz), 4.18 (2H, t, J=7.0 Hz), 1.74-1.62 (5H, m), 1.58-1.54 (2H, m), 1.39-1.36 (1H, m), 1.27-1.13 (3H, m), 0.97-0.90 (2H, m).

Synthesis of 3-Cyclohexylpropyl Acrylate (CHPA): 3-Cyclohexylpropyl acrylate was prepared by the same general procedure except that 3-cyclohexyl propanol was used instead of cyclohexyl methanol (99% yield). $^1$H-NMR (500 MHz, $CDCl_3$): δ 6.40 (1H, dd, J=1.0, 17.1 Hz), 6.11 (1H, dd, J=10.0, 17.1 Hz), 5.81 (1H, dd, J=1.5, 10.0 Hz), 4.13 (2H, t, J=7.1 Hz), 1.71-1.64 (7H, m), 1.25-1.20 (6H, m), 0.91-0.88 (2H, m).

Examples 1-5

Under yellow lighting, RMMs listed in Table 1 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. Polymer buttons (about 2 millimeters in thickness and 13 millimeters in diameter) were fabricated using a Teflon Cup and a circular glass plate held together in a stainless-steel fixture (base and open screw cap). About 350 microliters of RMM were dispensed into the Teflon Cup and assembled with the glass plate and stainless-steel fixture. The assembly was transferred into a cure box held at a temperature between 55° C. and 60° C. and then cured using TL03 lights having an intensity of 3-4 mW/cm$^2$ for 15 minutes followed by TL03 lights having an intensity of 6-7 mW/cm$^2$ for another 15 minutes. The cured assemblies were manually demolded. The samples were all transparent and exhibited low levels of surface tackiness. For each example, the refractive index and Abbe numbers were determined on the unextracted buttons and listed in Table 1.

TABLE 1

| Components (weight %) | Ex. 1 | Ex. 2 | Ex. 3 | Ex. 4 | Ex. 5 |
| --- | --- | --- | --- | --- | --- |
| CHA | 62 | 57 | 52 | 47 | 36 |
| PEA | 10 | 15 | 20 | 25 | 36 |
| NHA | 24.85 | 24.85 | 24.85 | 24.85 | 24.85 |
| TCDA | 3 | 3 | 3 | 3 | 3 |
| Omnirad 819 | 0.15 | 0.15 | 0.15 | 0.15 | 0.15 |

TABLE 1-continued

| Properties | Ex. 1 | Ex. 2 | Ex. 3 | Ex. 4 | Ex. 5 |
| --- | --- | --- | --- | --- | --- |
| RI (25) | 1.497947 | 1.500535 | 1.503177 | 1.505821 | 1.511641 |
| | (0.000278) | (0.000081) | (0.000029) | (0.000198) | (0.000049) |
| RI (35) | 1.494831 | 1.497222 | 1.499826 | 1.502526 | 1.508389 |
| | (0.000258) | (0.000196) | (0.000068) | (0.000178) | (0.000080) |
| Abbe # (25) | 52 (0) | 51 (0) | 50 (0) | 48 (0) | 46 (0) |

The RMM in Table 1 contain cyclohexyl acrylate, phenylethyl acrylate, n-hexyl acrylate, and a cycloaliphatic crosslinker. The amounts of cyclohexyl acrylate and phenylethyl acrylate are allowed to vary, but the amounts of n-hexyl acrylate, the cycloaliphatic crosslinker are fixed. The tests show that as the concentration of cyclohexyl acrylate decreases, the Abbe number also decreases while the RI measurement increases.

Examples 6-10

Under yellow lighting, the RMMs listed in Table 2 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. Polymer buttons were fabricated as described in Examples 1-5. About 350 microliters of RMM were dispensed between into the Teflon Cup and assembled with the glass plate and stainless-steel fixture, then the assembly was transferred into a cure box held at a temperature between 55° C. and 60° C. and then cured using TL03 lights having an intensity of 3-4 mW/cm$^2$ for 15 minutes followed by TL03 lights having an intensity of 6-7 mW/cm$^2$ for another 15 minutes. The cured assemblies were manually demolded. The samples were all transparent and exhibited low levels of surface tackiness, which decreased with increasing levels of TCDA. For each example, the refractive index and Abbe numbers were determined on the unextracted buttons and listed in Table 2. In some examples, these measurements were conducted on the front and back surfaces of the sample. These surfaces were in contact with either the Teflon Cup or the glass fixture. Small differences in refractive index and Abbe numbers were measured between the surfaces in contact with Teflon and glass.

Examples 11 and 12

Under yellow lighting, the RMMs listed in Table 2 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus was transferred into a cure box held at a temperature between 55° C. and 60° C. and then cured using TL03 lights having an intensity of 3-4 mW/cm$^2$ for 15 minutes followed by TL03 lights having an intensity of 6-7 mW/cm$^2$ for another 15 minutes. The cured assemblies were manually demolded. The samples were all transparent and exhibited low levels of surface tackiness; example 12 exhibited no tackiness. For each example, the refractive index and Abbe numbers were determined on the unextracted buttons and listed in Table 2.

TABLE 2

| | Ex. 6 | Ex. 7 | Ex. 8 | Ex. 9 | Ex. 10 | Ex. 11 | Ex. 12 |
|---|---|---|---|---|---|---|---|
| Components (weight %) | | | | | | | |
| CHA | 52 | 52 | 52 | 52 | 50 | 36 | 36 |
| PEA | 20 | 20 | 20 | 20 | 22 | 36 | 36 |
| NHA | 24.85 | 21.85 | 19.85 | 18.85 | 18.85 | 24.85 | 6.85 |
| TCDA | 3 | 6 | 8 | 9 | 9 | 3 | 3 |
| XLMA | 0 | 0 | 0 | 0 | 0 | 0 | 18 |
| Omnirad 819 | 0.15 | 0.15 | 0.15 | 0.15 | 0.15 | 0.15 | 0.15 |
| Properties | | | | | | | |
| RI (25) | 1.503177 (0.000029) | 1.506088 (0.000700) | 1.508474 (0.000223) | Teflon 1.509408 (0.000411) Glass 1.508175 (0.000114) | Teflon 1.509240 (0.000584) Glass 1.508129 (0.000585) | 1.511641 (0.000049) | 1.503541 (0.000025) |
| Abbe # (25) | 50 (0) | 50 (1) | 50 (0) | Teflon 50 (1) Glass 50 (0) | Teflon 49 (0) Glass 50 (0) | 46 (0) | 46 (0) |

The RMM shown in Ex. 6-10 maintained generally similar amounts of cyclohexyl acrylate and phenylethyl acrylate, but allowed the n-hexyl acrylate and crosslinker to vary. The Abbe number was generally consistent across these examples, but as the concentration of the cycloaliphatic crosslinker increased, there was a measurable increase in the refractive index. The RMM shown in Ex. 11-12 generally shows that the inclusion of the XMLA crosslinker does not materially impact the RI or Abbe measurements. However, with lower amounts of cyclohexyl acrylate and comparatively higher amounts of phenylethyl acrylate, and the Abbe numbers decreased in comparison to Ex. 6-10.

Examples 13-14

Under yellow lighting, the RMMs listed in Table 3 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. Polymer buttons were fabricated as described in Examples 1-5. About 350 microliters of RMM were dispensed between into the Teflon Cup and assembled with the glass p[late and stainless-steel fixture, then the assembly was transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. The samples were all transparent and exhibited no surface tackiness. For each example, the refractive index and Abbe numbers were determined on the unextracted buttons and listed in Table 3. These experiments show the impact on RI and Abbe when the concentration of HBA and PVP 90 is varied.

Example 15

Under yellow lighting, the RMM listed in Table 3 was degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. Polymer buttons were fabricated by dispensing about 350 microliters of RMM using the Teflon Cup assembly, or alternatively by dispensing inside an O-ring that is placed between two glass plates and held together with clamps, then apparatus was transferred into a cure box held at a temperature between 55° C. and 60° C., and cured using TL03 lights having an intensity of 3-4 mW/cm² for 15 minutes followed by TL03 lights having an intensity of 6-7 mW/cm² for another 15 minutes. The cured assemblies were manually demolded. The samples were essentially transparent and exhibited no surface tackiness. For each example, the refractive index and Abbe numbers were determined on the unextracted buttons and listed in Table 3.

Example 16

Under yellow lighting, the RMM listed in Table 3 was degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. The samples were essentially transparent and exhibited no surface tackiness. For each example, the refractive index and Abbe numbers were determined on the unextracted buttons and listed in Table 3.

Example 17

Under yellow lighting, the RMM listed in Table 3 was degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. The samples were essentially transparent (slightly hazy) and exhibited no surface tackiness. For each example, the refractive index and Abbe numbers were determined on the unextracted buttons and listed in Table 3.

Example 18

Under yellow lighting, the RMM listed in Table 3 was degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed into the Teflon Cup and assembled with the glass plate and stainless-steel fixture, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. The samples were all transparent and exhibited slight surface tackiness. For each example, the refractive index and Abbe numbers were determined on the unextracted buttons and listed in Table 3. In some examples, these measurements were conducted on the front and back surfaces of the sample. These surfaces were in contact with either the Teflon Cup, the glass fixture, or glass plates. Small differences in refractive index and Abbe numbers were measured between the surfaces in contact with Teflon and glass.

All of the above examples exhibited desirable RI and Abbe numbers.

Examples 19-24

Under yellow lighting, the RMMs listed in Table 4 were degassed by sparging with nitrogen gas at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. The samples were transparent and exhibited no surface tackiness. For each example, the refractive index and Abbe numbers were determined and listed in Table 4.

Example 25

Under yellow lighting, the RMM listed in Table 4 was degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature of about 40° C. and then cured using 430 nm LED lights having an intensity of 18-20 mW/cm² for about 60 minutes. The cured assemblies were manually demolded. The samples were transparent and exhibited no surface tackiness. For each example, the refractive index and Abbe numbers were determined on the unextracted buttons and listed in Table 4.

TABLE 3

| | Ex. 13 | Ex. 14 | Ex. 15 | Ex. 16 | Ex. 17 | Ex. 18 |
|---|---|---|---|---|---|---|
| Components (weight %) | | | | | | |
| CHA | 52 | 52 | 52 | 52 | 52 | 26 |
| EGDCA | 0 | 0 | 0 | 0 | 0 | 26 |
| PEA | 20 | 20 | 20 | 20 | 20 | 20 |
| NHA | 9.36 | 9.36 | 12.36 | 0 | 0 | 18.86 |
| HBA | 10 | 9.5 | 7 | 7 | 7 | 0 |
| PVP 90 | 0.5 | 1 | 0.5 | 0.5 | 0.5 | 0 |
| TCDA | 8 | 8 | 8 | 8 | 8 | 9 |
| XLMA | 0 | 0 | 0 | 12.36 | 0 | 0 |
| OH-mPDMS | 0 | 0 | 0 | 0 | 12.36 | 0 |
| Omnirad 819 | 0.14 | 0.14 | 0.14 | 0.14 | 0.14 | 0.14 |
| Properties | | | | | | |
| RI (25) | Teflon 1.510254 (0.000130) Glass 1.509821 (0.000522) | Teflon 1.509830 (0.000484) Glass 1.510733 (0.000256) | Teflon 1.508553 (0.001295) Glass 1.507788 (0.001383) Glass Plates 1.509428 | Glass Plates 1.503340 (0.000267) | Glass Plates 1.502686 | Teflon 1.509830 (0.000484) Glass 1.510733 (0.000256) |
| Abbe # (25) | Teflon 51 (1) Glass 52 (3) | Teflon 54 (2) Glass 50 (0) | Teflon 51 (1) Glass 52 (4) Glass Plates 50 (0) | Glass Plates 51 (0) | Glass Plates 51 (0) | Teflon 54 (2) Glass 50 (0) |

TABLE 4

|  | Ex. 19 | Ex. 20 | Ex. 21 | Ex. 22 | Ex. 23 | Ex. 24 | Ex. 25 |
|---|---|---|---|---|---|---|---|
| Components (weight %) | | | | | | | |
| CHA | 51.25 | 52 | 52.75 | 51.25 | 49.25 | 52.75 | 52.75 |
| PEA | 20 | 19 | 17.5 | 20 | 22 | 17.5 | 14 |
| NHA | 17.91 | 18.16 | 18.91 | 16.91 | 16.91 | 17.91 | 18.91 |
| DMA | 2 | 2 | 2 | 2 | 2 | 2 | 2 |
| TCDA | 8 | 8 | 8 | 9 | 9 | 9 | 8 |
| UVB | 0.7 | 0.7 | 0.7 | 0.7 | 0.7 | 0.7 | 0.7 |
| HEVB | 0 | 0 | 0 | 0 | 0 | 0 | 3.5 |
| Omnirad 819 | 0.14 | 0.14 | 0.14 | 0.14 | 0.14 | 0.14 | 0.14 |
| Properties | | | | | | | |
| RI (25) | 1.508904 (0.000018) | 1.508730 (0.000045) | 1.507245 (0.000290) | 1.510277 (0.000040) | 1.511075 (0.000443) | 1.506641 (0.000394) | 1.510551 (0.001891) |
| RI (35) | — | — | — | — | — | 1.504755 (0.000382) | — |
| Abbe # | 48.82 (0.04) | 48.92 (0.09) | 50.31 (1.24) | 48.62 (0.20) | 48.50 (0.16) | 49.04 (0.27) | 46.09 (0.52) |

Examples 26-32

Under yellow lighting, the RMMs listed in Table 5 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. The samples were transparent and exhibited no surface tackiness. For each example, the refractive index and Abbe numbers were determined on the unextracted buttons and listed in Table 5.

hydroxybutyl acrylate monomer. The high refractive index measurements (all over 1.5) and Abbe numbers (48-50) are noted.

Examples 33-34

Under yellow lighting, the RMMs listed in Table 6 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were

TABLE 5

|  | Ex. 26 | Ex. 27 | Ex. 28 | Ex. 29 | Ex. 30 | Ex. 31 | Ex. 32 |
|---|---|---|---|---|---|---|---|
| Components (weight %) | | | | | | | |
| CHA | 51.5 | 52 | 52.5 | 52 | 53 | 53 | 53 |
| PEA | 20 | 19 | 18 | 20 | 17.5 | 17.5 | 17.5 |
| NHA | 9.16 | 9.66 | 10.16 | 9.36 | 10.16 | 13.16 | 10.16 |
| HBA | 9.5 | 9.5 | 9.5 | 9.5 | 9.5 | 7 | 9.5 |
| TCDA | 8 | 8 | 8 | 8 | 8 | 8 | 8 |
| UVB | 0.7 | 0.7 | 0.7 | 0 | 0.7 | 0.7 | 0.7 |
| PVP K90 | 1 | 1 | 1 | 1 | 1 | 0.5 | 0 |
| PDMA | 0 | 0 | 0 | 0 | 0 | 0 | 1 |
| Omnirad 819 | 0.14 | 0.14 | 0.14 | 0.14 | 0.14 | 0.14 | 0.14 |
| Properties | | | | | | | |
| RI (25) | 1.511588 (0.000146) | 1.510858 (0.000032) | 1.509719 (0.000539) | 1.510733 (0.000256) | 1.508937 (0.0001520) | 1.507781 (0.000115) | 1.508248 (0.000226) |
| RI (35) | — | — | 1.507042 (0.000272) | — | 1.506843 (0.000466) | 1.504578 (0.000155) | 1.505985 (0.000098) |
| Abbe # (25) | 48.86 (0.20) | 49.35 (0.03) | 49.82 (0.41) | 50.00 (0.04) | 49.37 (0.26) | 49.95 (0.55) | 49.64 (0.31) |
| Abbe # (35) | — | — | 49.66 (0.33) | — | 49.72 (0.10) | 49.57 (0.05) | 49.64 (0.31) |

As may be seen, Ex. 26-32 show data for samples made with components similar to the previous examples, but also with a polyamide wetting agent (PVP) and an additional manually demolded. Example 33 was transparent and exhibited no surface tackiness. Example 34 was slightly hazy and exhibited no surface tackiness. For each example, the refractive index and Abbe numbers were determined on the unextracted buttons and listed in Table 6.

TABLE 6

| Components (weight %) | Ex. 16 | Ex. 33 | Ex. 34 |
|---|---|---|---|
| CHA | 52 | 52.75 | 53 |
| PEA | 20 | 17.5 | 17.5 |
| NHA | 0 | 9.91 | 0 |
| HBA | 7 | 0 | 9.5 |
| DMA | 0 | 2 | 0 |
| PVP 90 | 0.5 | 0 | 1 |
| TCDA | 8 | 7 | 8 |
| XLMA | 12.36 | 10 | 10.16 |
| UVB | 0 | 0.7 | 0 |
| Omnirad 819 | 0.14 | 0.14 | 0.14 |
| Properties | Ex. 16 | Ex. 33 | Ex. 34 |
| RI (25) | 1.503340 (0.000267) | 1.501516 (0.000131) | 1.505650 (0.000164) |
| RI (35) | — | 1.498512 (0.000365) | 1.502645 (0.000137) |
| Abbe # (25) | 51 (0) | 49.85 (1.07) | 49.73 (0.23) |
| Abbe # (35) | — | 49.98 (0.52) | 49.57 (0.12) |

Examples 35-36 and Comparative Examples 1-2

Under yellow lighting, reactive monomer mixtures were prepared from the formulations listed in Table 7. All components were accurately weighed into an amber glass container and tightly capped with a PTFE lined screw cap. The container was placed on jar roller and rolled until a homogeneous mixture was obtained. The RMM was filtered through a 0.45 μm PTFE membrane (Pall Corporation, Part #66148) using a luer lock glass syringe and a stainless steel filter fixture and subsequently degassed by sparging with nitrogen gas for at least 3 minutes and back filling with nitrogen gas. The degassed RMM was placed in the RMM mold filling compartment of the glove box (<0.1% oxygen, room temperature); the cap was unscrewed; and the RMM was equilibrated for about 3 minutes before use.

In a glove box with a nitrogen gas atmosphere and less than 0.1 percent oxygen gas (v/v), about 75-100 μL of the reactive mixture were dosed using an Eppendorf pipet at room temperature into the front curve mold made of polypropylene. The base curve mold also made of polypropylene was then placed onto the front curve mold. The polypropylene molds were equilibrated for a minimum of twelve hours in the glove box prior to dosing. The assemblies were transferred into an adjacent glove box maintained at about 60-65° C., and the lenses were cured from the top and bottom for a total of ninety minutes using 435 nm LED lights on both sides with the following intensity profile: 20 minutes at 5 mW/cm² (2.5 mW/cm² top and 2.5 mW/cm² bottom), 20 minutes at 10 mW/cm² (5 mW/cm² top and 5 mW/cm² bottom), 20 minutes at 20 mW/cm² (10 mW/cm² top and 10 mW/cm² bottom) and 30 minutes at 30 mW/cm² (15 mW/cm² top and 15 mW/cm² bottom).

The cured assemblies were manually demolded. The base curve molds were separated from the front curve molds using tweezers, and the any flash polymer removed. The front curve molds with lenses still attached were placed in the refrigerator at 4° C. for at least one minute; The cold molds were then removed, and the lenses mechanically released by applying force on the reverse side of the mold.

Example 36 was fabricated according to the procedure of Example 35 except that it was thermally cured at 60-65° C. for 72 hours instead of photocured. Both photocured and thermally cured lenses were used for glistenings analysis.

Polymer buttons were fabricated for refractive index, Abbe number and glass transition temperature measurements. About 350 microliters of RMM were dispensed inside an O-ring that is placed between two glass plates and held together with clamps. The assemblies were transferred into an adjacent glove box maintained at about 60-65° C. and cured using the photo conditions above for corresponding lenses. Polymer buttons for Example 36 were produced similarly, except that it was thermally cured at 60-65° C. for 72 hours instead of photocured.

Figure 2:
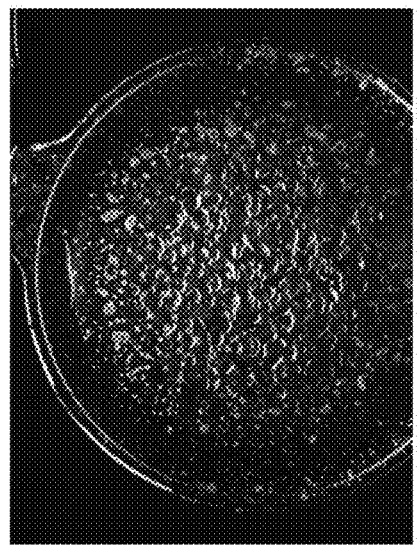
FIG. 2 shows the level of macro-glistening in example 35 by dark field microscopy.
Figure 2:
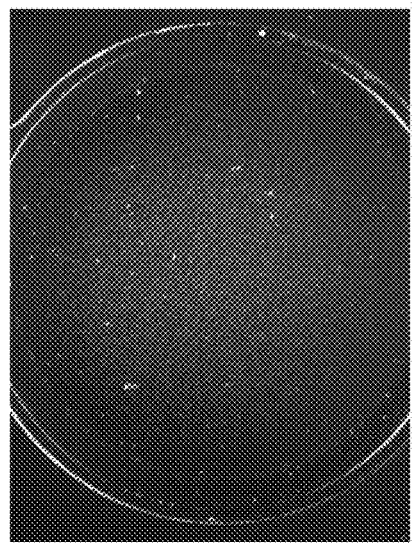
Figure 2:
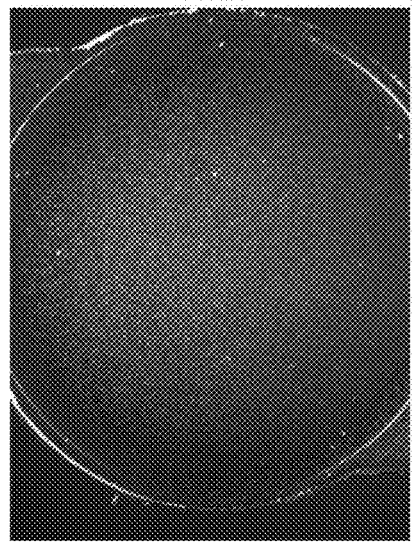

For example 35, the refractive index, Abbe number, and glass transition temperature were determined on the unextracted polymer buttons and listed in Table 7. In addition, the glass transition temperature of example 36 was also determined. Unextracted lenses from example 35 and comparative examples 1 and 2 were analyzed for micro-vacuoles or micro-glistenings following the procedure described earlier in "Micro-glistening Test Method", and the dark field micrographs are shown in FIG. 1. Example 35 was also analyzed for macro-vacuoles or macro-glistenings following the procedure described earlier in "Macro-glistening Test Method" and the dark field micrographs are shown in FIG. 2. Three conditions were compared. In the first condition lenses were fabricated, and without extraction, and incubated for 3 days in PBS at 37° C. In the second condition lenses were fabricated, extracted with acetonitrile and dried following the steps described earlier in "Macro-glistening Test Method", and subsequently incubated for 3 days in PBS at 37° C. In the third condition, lenses were fabricated, extracted with acetonitrile, dried, subjected to the gradient equilibration steps described earlier in "Macro-glistening Test Method", and finally incubated for 3 days in PBS at 37° C.

TABLE 7

| Components (weight %) | Ex. 35 | Ex. 36 | Comparative Ex. 1 | Comparative Ex. 2 |
|---|---|---|---|---|
| EGDCA | 53.14 | 53.10 | 0 | 0 |
| NHA | 18 | 17.93 | 0 | 0 |
| PEA | 0 | 0 | 36.68 | 51.68 |
| PEMA | 16.27 | 16.37 | 60 | 45 |
| DMA | 2 | 1.99 | 0 | 0 |
| TCDA | 8 | 7.97 | 0 | 0 |
| EGDMA | 0 | 0 | 3 | 3 |
| HEVB | 2.25 | 2.24 | 0 | 0 |
| Omnirad 819 | 0.34 | 0 | 0.34 | 0.34 |
| AIBN | 0 | 0.40 | 0 | 0 |
| Properties | | | | |
| RI (25) | 1.527 | — | — | — |
| Abbe # (25) | 50 | — | — | — |
| $T_g$ ($1^{st}$ scan) | 14.4 | 9.6 | — | — |
| $T_g$ ($2^{nd}$ scan) | 13 | 8.8 | — | — |

As shown in the micrographs in FIG. 1, example 35 contained less micro-glistenings than the comparative examples. Under the more severe gradient equilibration conditions, example 35 showed a level of macro-glistenings not observed in the as-fabricated without extraction lens or the acetonitrile only extracted followed by drying lens.

Examples 37-43

Figure 3:
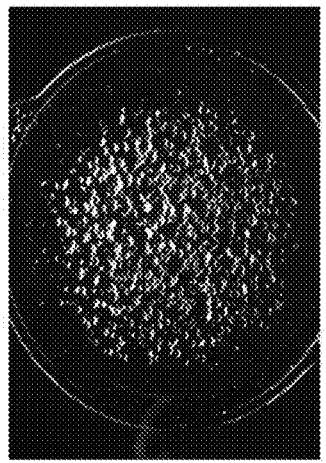
FIG. 3 shows the level of macro-glistening in examples 37-43 by dark field microscopy.
Figure 3:
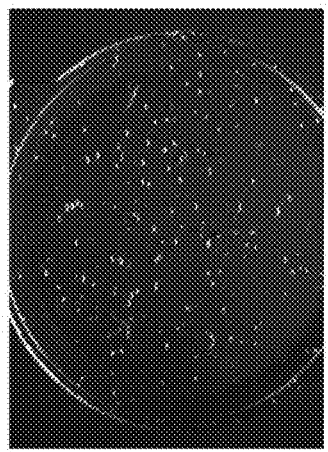
Figure 3:
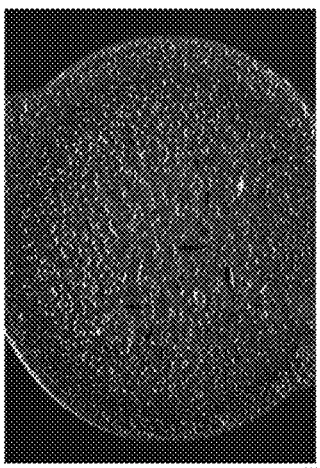
Figure 3:
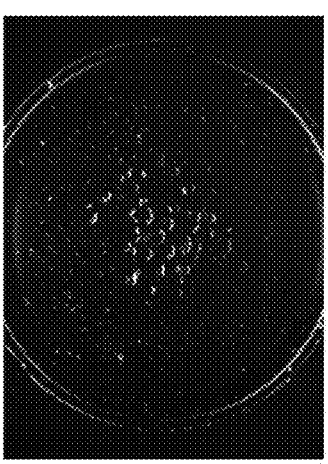
Figure 3:
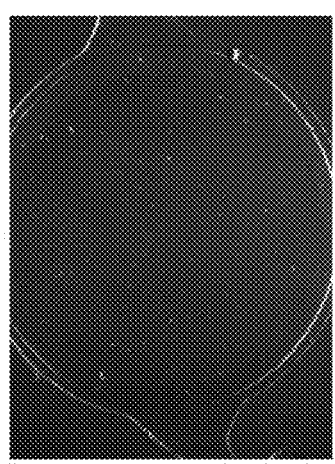
Figure 3:
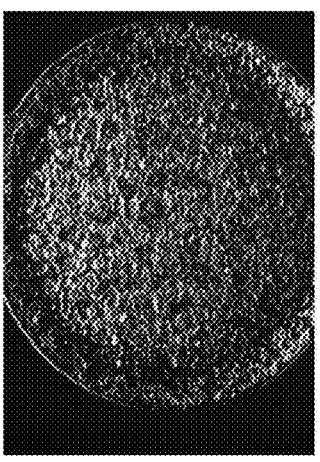
Figure 3:
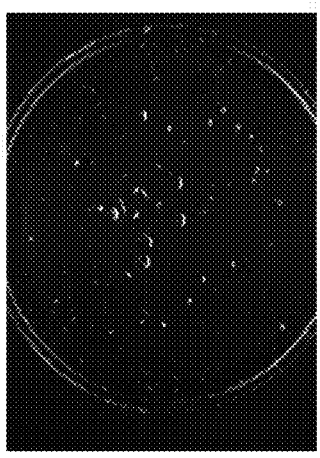

A series of RMM (examples 38-43) were prepared by first making a master batch formulation (example 37), and then, adding enough hydrophilic monomer to a portion of the master batch to make a new RMM containing the weight percentages of hydrophilic monomers listed in Table 8. These new RMMs contained approximately the same molar equivalents of hydrophilic monomers having different polymerizable moieties which would influence their incorporation kinetics relative to the other components in the RMMs. Thus, the desired polymerizable functionality as well as the desired relative hydrophilicity impact could be explored from a macro-glistenings standpoint. Using the procedure described in example 35, lenses were made from the master batch as well as the new RMM containing hydrophilic monomers. Following the procedure described earlier in "Macro-glistening Test Method", lenses were fabricated, extracted with acetonitrile and dried, gradient equilibrated and incubated for 3 days in PBS at 37° C. All lenses were analyzed for macro-vacuoles or macro-glistenings, and the dark field micrographs are shown in FIG. 3.

acrylate monomers studied, and the lenses produced were virtually free of macro-glistenings. It is surmised that the slower monomers, DMA and NVP, likely produced hydrophilic domains or localized areas of DMA/NVP enrichment, resulting in an uneven or anisotropic distribution of water in the hydrated crosslinked polymer. In the RMMs where the reactivity of the hydrophilic monomer (e.g. HEMA, HBA, mPEG 300, PEG-OH 360) is comparable to other reactive components, there is a potential to produce a more random crosslinked polymer or a network in which the hydrophilic monomer is more evenly distributed or delocalized, resulting in a more even or isotropic distribution of water in the hydrated polymer.

Examples 44-51

Under yellow lighting, reactive monomer mixtures were prepared from the formulations listed in Table 9. All com-

TABLE 8

| | Ex. 37 | Ex. 38 | Ex. 39 | Ex. 40 | Ex. 41 | Ex. 42 | Ex. 43 |
|---|---|---|---|---|---|---|---|
| Components (weight %) | | | | | | | |
| EGDCA | 89.41 | | | | | | |
| TCDA | 8 | | | | | | |
| HEVB | 2.25 | | | | | | |
| Omnirad 819 | 0.34 | | | | | | |
| The following hydrophilic monomers were dissolved into the RMM of Ex. 37 in portions to make new RMM with the listed weight percentages of the hydrophilic monomers. | | | | | | | |
| NVP | 0 | 16.8 | 0 | 0 | 0 | 0 | 0 |
| DMA | 0 | 0 | 15 | 0 | 0 | 0 | 0 |
| HEMA | 0 | 0 | 0 | 19.7 | 0 | 0 | 0 |
| HBA | 0 | 0 | 0 | 0 | 21.8 | 0 | 0 |
| mPEG 300 | 0 | 0 | 0 | 0 | 0 | 21.8 | 0 |
| PEG-OH 360 | 0 | 0 | 0 | 0 | 0 | 0 | 21.8 |

As shown in FIG. 3, by incorporating hydrophilic monomers the lens composition, macro-glistenings were reduced as compared to the control lens from the master batch. The macro-glistening data in FIG. 3 align with the following order with respect to severity: Control Lens>NVP>DMA>mPEG 300>HBA>HEMA>PEG-OH 360. Whereas the reactivity of the hydrophilic monomer relative to the other reactive components in the composition has the following order: HBA>HEMA, PEG-OH 360, mPEG 300>DMA>NVP, the relative hydrophilicity of the hydrophilic monomers is consistent with the following order: DMA>NVP, PEG-OH 360>mPEG 300>HEMA>HBA. This suggests that the level of macro-glistening obtained is governed by both the reactivity of the hydrophilic monomer relative to the other reactive components in the composition, as well as the relative hydrophilicity of the hydrophilic monomer, of which the former has the more pronounced effect. DMA and NVP are more hydrophilic but react or polymerize much slower compared to the other reactive components in their respective RMM's, and the resulting lenses exhibited the highest level of macro-glistenings relative to the control. Whereas, HEMA, HBA, m-PEG 300 and PEG-OH 360 are less hydrophilic relative to DMA and NVP, their reactivities are comparable to the other reactive components in their respective RMMs and produced lenses with far less macro-glistenings compared to the control lenses and lenses containing DMA and NVP. With PEG-OH 360, not only is the reactivity comparable to the other reactive components in its RMM, but it is the most hydrophilic monomer in this group of (meth)

ponents were accurately weighed into an amber glass container and tightly capped with a PTFE lined screw cap. The container was placed on jar roller and rolled until a homogeneous mixture was obtained. The RMM was filtered through a 0.45 μm PTFE membrane (Pall Corporation, Part #66148) using a luer lock glass syringe and a stainless steel filter fixture and subsequently degassed by sparging with nitrogen gas for at least 3 minutes and back filling with nitrogen gas. The degassed RMM was placed in the RMM mold filling compartment of the glove box (<0.1% oxygen, room temperature); the cap was unscrewed; and the RMM was equilibrated for about 3 minutes before use. Polymer buttons were fabricated for the determination of refractive index, Abbe number, glass transition temperature and water content, and lenses were fabricated for the assessment of macro-glistenings.

Polymer buttons: In a glove box with a nitrogen gas atmosphere and less than 0.1 percent oxygen gas (v/v), about 350 μL of the reactive mixture were dispensed using an Eppendorf pipet at room temperature inside an O-ring that is placed between two glass plates and held together with clamps, and then the apparatus was transferred into an adjacent glove box maintained at about 60-65° C., and the buttons were cured from the top and bottom for a total of ninety minutes using 435 nm LED lights on both sides with the following intensity profile: 20 minutes at 5 mW/cm$^2$ (2.5 mW/cm$^2$ top and 2.5 mW/cm$^2$ bottom), 20 minutes at 10 mW/cm$^2$ (5 mW/cm$^2$ top and 5 mW/cm$^2$ bottom), 20 minutes at 20 mW/cm$^2$ (10 mW/cm$^2$ top and 10 mW/cm$^2$ bottom) and 30 minutes at 30 mW/cm$^2$ (15 mW/cm$^2$ top and 15 mW/cm$^2$ bottom).

The cured buttons were manually demolded. The glass plates were pried open with a spatula and razor blade. In some cases, the temperature was increased or decreased to facilitate demolding. Any flash polymer was removed as well. The buttons were extracted with 2-propanol and dried using the following procedure: 1) buttons were placed in individual amber glass containers (with PTFE lined screw caps), about 30 mL 2-propanol added and placed on a benchtop orbital shaker at 100 rpm for overnight at room temperature, 2) 2-propanol was completely decanted, about 25 mL 2-propanol added and extraction continued on the benchtop orbital shaker at 100 rpm for about 2 hours at room temperature, 3) 2-propanol was completely decanted, about 25 mL 2-propanol added and extraction continued on the benchtop orbital shaker at 100 rpm for about 2 hours at room temperature, 4) 2-propanol was completely decanted and the buttons were placed on a Teflon surface and allowed to air dry overnight, 5) the air-dried buttons on the Teflon surface was placed in a glove box at room temperature with a nitrogen atmosphere and less than 0.1 percent oxygen, which is maintained by an active nitrogen sparge, and the buttons were dried overnight, 6) the buttons on the Teflon surface were transferred to a heated glove box maintained at 60-65° C., with a nitrogen atmosphere and less than 0.1 percent oxygen, which is maintained by an active nitrogen sparge, and the buttons were dried for 3 days.

The dry buttons were used for the measurement of refractive index, Abbe number, glass transition temperature and water content, which are listed in Table 10 for each example.

The dry refractive index and Abbe number on both surfaces of the polymer buttons were measured at 25° C. and the average was reported. The wet refractive index on both surfaces of the polymer buttons was measured at 25° C. after being suspended in PBS for 14 days at 37° C., and the average was reported. The surfaces of the polymer buttons were thoroughly blotted using lint-free blotting paper to remove surface/excess PBS prior to the wet refractive index measurements. The difference in refractive index (ΔRI) is defined as the wet refractive index minus the dry refractive index. For water content measurement, buttons were incubated in PBS at 37° C. for 14 days and the water content was subsequently determined using the "Drying Method" described earlier. The water content was determined after 24, 48 and 72 hours of drying, which did not change much over this time period, but the average value was calculated and listed in Table 10.

Lenses: In a glove box with a nitrogen gas atmosphere and less than 0.1 percent oxygen gas (v/v), about 75-100 μL of the reactive mixture were dosed using an Eppendorf pipet at room temperature into the front curve mold made of polypropylene. The base curve mold also made of polypropylene was then placed onto the front curve mold. The polypropylene molds were equilibrated for a minimum of twelve hours in the glove box prior to dosing. The lens mold assemblies, were transferred into an adjacent glove box maintained at about 60-65° C., and the lenses were cured from the top and bottom for a total of ninety minutes using 435 nm LED lights on both sides with the following intensity profile: 20 minutes at 5 mW/cm$^2$ (2.5 mW/cm$^2$ top and 2.5 mW/cm$^2$ bottom), 20 minutes at 10 mW/cm$^2$ (5 mW/cm$^2$ top and 5 mW/cm$^2$ bottom), 20 minutes at 20 mW/cm$^2$ (10 mW/cm$^2$ top and 10 mW/cm$^2$ bottom) and 30 minutes at 30 mW/cm$^2$ (15 mW/cm$^2$ top and 15 mW/cm$^2$ bottom). The cured assemblies were manually demolded. The base curve molds were separated from the front curve molds using tweezers, and the any flash polymer removed. The front curve molds with lenses still attached were placed in the refrigerator at 4° C. for at least one minute; The cold molds were then removed, and the lenses mechanically released by applying force on the reverse side of the mold.

Figure 4:
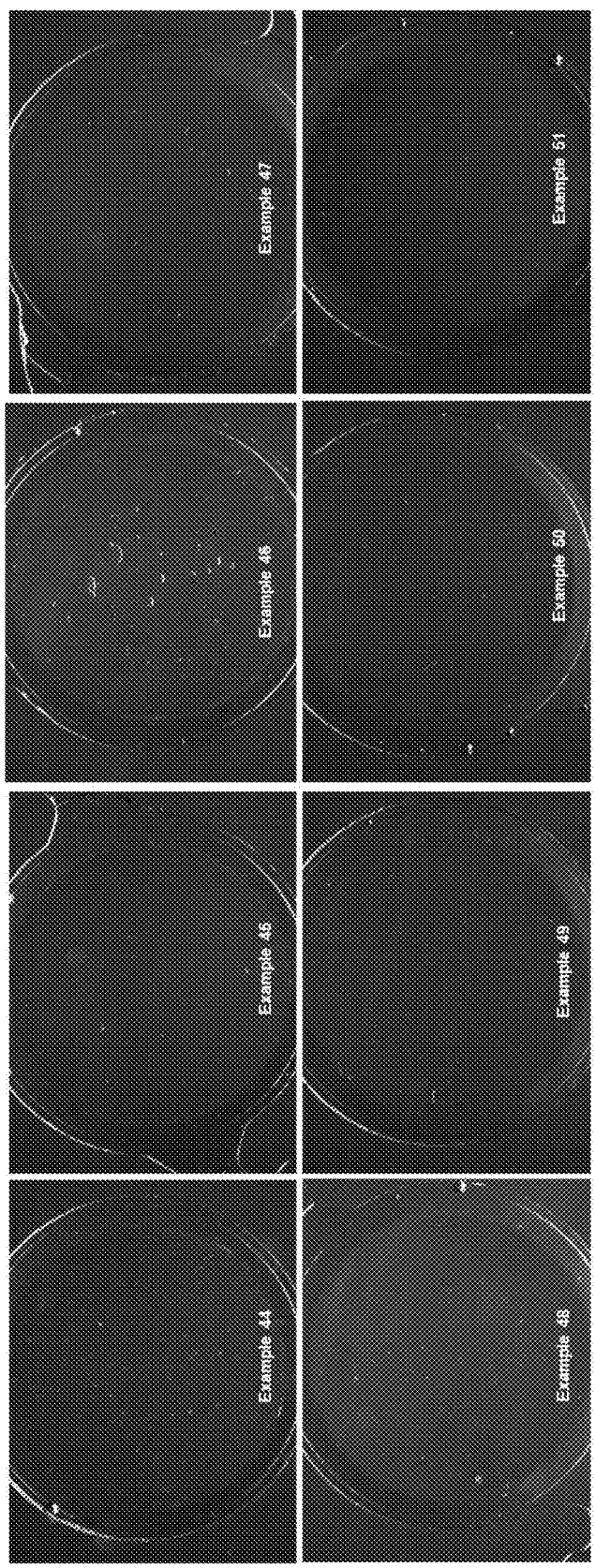
FIG. 4 shows the level of macro-glistening in examples 44-51 by dark field microscopy.

For each example lenses were extracted with methanol, gradient equilibrated with PBS and, analyzed for macro-vacuoles or macro-glistenings following the procedure described earlier in "Macro-glistening Test Method", and the dark field micrographs by dark field microscopy are as shown in FIG. 4. The size of the macro-vacuoles or macro-glistenings were large enough to be counted, and the range of the number of macro-vacuoles or micro-glistenings per lens in 4 lenses are shown in Table 10.

TABLE 9

| | Ex. 44 | Ex. 45 | Ex. 46 | Ex. 47 | Ex. 48 | Ex. 49 | Ex. 50 | Ex. 51 |
|---|---|---|---|---|---|---|---|---|
| Components (weight %) | | | | | | | | |
| EGDCA | 57.14 | 57.14 | 57.14 | 57.14 | 57.14 | 57.14 | 57.14 | 50.14 |
| TCDA | 6 | 8 | 6 | 8 | 8 | 8 | 8 | 8 |
| EGDMA | 0 | 0 | 2 | 0 | 0 | 0 | 0 | 0 |
| HEVB | 2.25 | 2.25 | 2.25 | 2.25 | 2.25 | 2.25 | 2.25 | 2.25 |
| Omnirad 819 | 0.34 | 0.34 | 0.34 | 0.34 | 0.34 | 0.34 | 0.34 | 0.34 |
| PEG-OH 360 | 22 | 20 | 20 | 20 | 20 | 20 | 20 | 20 |
| PEA | 12.27 | 12.27 | 12.27 | 0 | 0 | 0 | 0 | 0 |
| PPA | 0 | 0 | 0 | 12.27 | 0 | 0 | 0 | 0 |
| CHMA | 0 | 0 | 0 | 0 | 12.27 | 0 | 0 | 0 |
| CHEA | 0 | 0 | 0 | 0 | 0 | 12.27 | 0 | 0 |
| CHPA | 0 | 0 | 0 | 0 | 0 | 0 | 12.27 | 19.27 |

TABLE 10

| | Dry RI[1] | Wet RI[1] Day 14 | ΔRI | Abbe # (25)[1] | $T_g$ (1$^{st}$, 2$^{nd}$ scans) | % WC[2] | Range in # of Macro-Glistenings per Lens[3] |
|---|---|---|---|---|---|---|---|
| Ex. 44 | 1.530530 (0.000059) | 1.517558 (0.000194) | 0.0130 | 47.67 (0.32) | −0.7, −1.9 | 7.3 | 0 |

TABLE 10-continued

|  | Dry RI[1] | Wet RI[1] Day 14 | ΔRI | Abbe # (25)[1] | $T_g$, ($1^{st}$, $2^{nd}$ scans) | % WC[2] | Range in # of Macro-Glistenings per Lens[3] |
|---|---|---|---|---|---|---|---|
| Ex. 45 | 1.531944 (0.000072) | 1.521391 (0.000142) | 0.0106 | 47.30 (0.09) | 3.8, 4.3 | 6.8 | 0 |
| Ex. 46 | 1.531600 (0.000056) | 1.521489 (0.000198) | 0.0101 | 47.05 (0.77) | 4.0, 2.2 | 6.4 | 10-15 |
| Ex. 47 | 1.530734 (0.000052) | 1.520962 (0.000202) | 0.0098 | 48.36 (0.48) | 5.2, 3.3 | 6.8 | 0 |
| Ex. 48 | 1.524031 (0.000054) | 1.513001 (0.000170) | 0.0110 | 52.68 (3.26) | 3.8, 2.0 | 7.3 | 0 |
| Ex. 49 | 1.523725 (0.000154) | 1.513350 (0.000314) | 0.0104 | 51.15 (0.85) | −0.5, −2.1 | 6.9 | 0 |
| Ex. 50 | 1.523122 (0.000041) | 1.512792 (0.000320) | 0.0103 | 52.03 (1.19) | 3.0, 2.9 | 7.4 | 0 |
| Ex. 51 | 1.520114 (0.000089) | 1.509648 (0.000106) | 0.0105 | 51.55 (0.21) | 0.7, −0.5 | 7.1 | 0 |

[1]Three polymer buttons, both surfaces measured, average of six measurements
[2]Drying Method
[3]Four Lenses For the most part, examples 44-51 showed an excellent balance of properties including refractive indexes over about 1.52 and Abbe numbers greater than about 47, while exhibiting virtually no macro-glistenings.

Examples 52-55

Lenses were prepared from RMM listed in Table 11 according to the procedure for examples 44-51. For each example, lenses were extracted with methanol, gradient equilibrated with PBS, and analyzed for macro-vacuoles or macro-glistenings following the procedure described earlier in "Macro-glistening Test Method". Four lenses were analyzed and, and the dark field micrographs of lenses with the highest number of macro-glistenings for each example are as shown in FIG. 5

TABLE 11

| Components (weight %) | Ex. 45 | Ex. 52 | Ex. 53 | Ex. 54 | Ex. 55 |
|---|---|---|---|---|---|
| EGDCA | 57.14 | 58.14 | 59.14 | 60.14 | 61.14 |
| TCDA | 8 | 9 | 10 | 11 | 12 |
| HEVB | 2.25 | 2.25 | 2.25 | 2.25 | 2.25 |
| Omnirad 819 | 0.34 | 0.34 | 0.34 | 0.34 | 0.34 |
| PEG-OH 360 | 20 | 18 | 16 | 14 | 12 |
| PEA | 12.27 | 12.27 | 12.27 | 12.27 | 12.27 |

Figure 5:
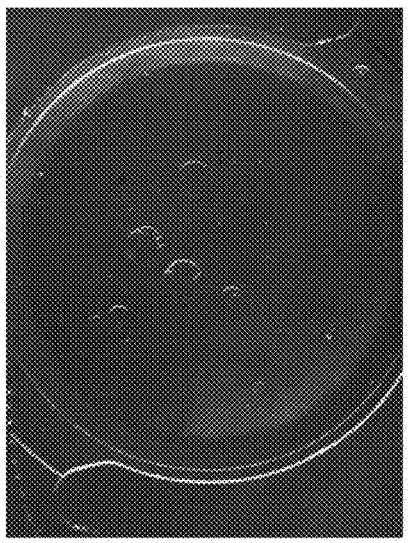
FIG. 5 shows the level of macro-glistening in examples 45 and 52-55 by dark field microscopy.
Figure 5:
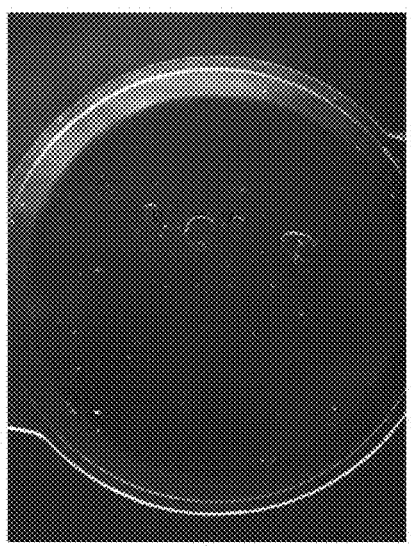
Figure 5:
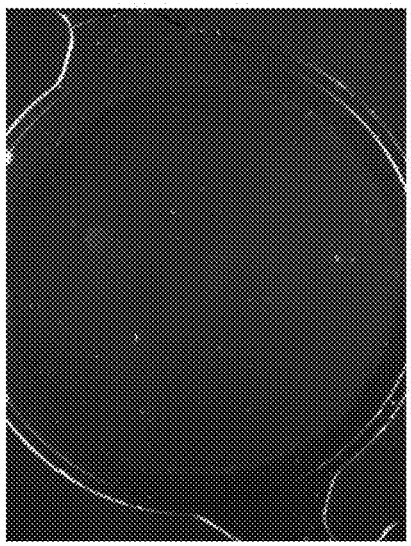
Figure 5:
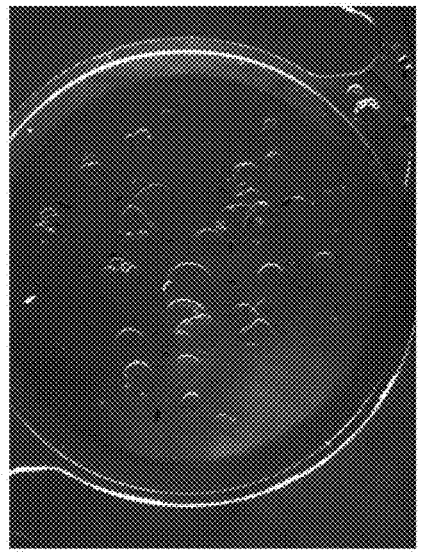
Figure 5:
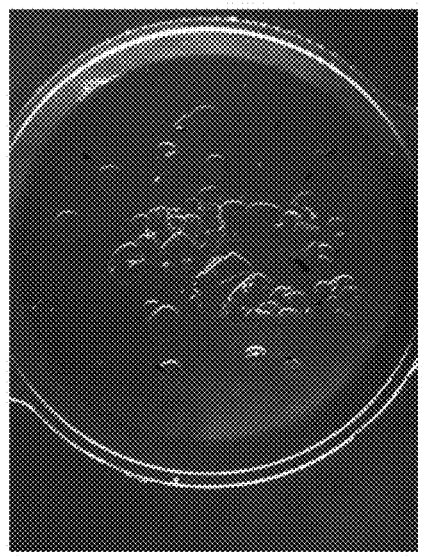

In examples 45 and 52-55, as the amount of PEG-OH 360 decreased and the amount of TCDA increased, the level of macro-glistenings increased as shown in FIG. 5.

Examples 56-71

Polymer buttons and lenses were prepared from RMM listed in Table 12 according to the procedure for examples 44-51, except that for the polymer buttons only, the light source was TL03 lights having an intensity of 5-6 mW/cm². For each example, the refractive index, Abbe number, glass transition temperature, and water content were determined and listed in Table 13. The dry refractive index and Abbe number on both surfaces of the buttons were measured at 25° C. and the average was reported. The wet refractive index on both surfaces of the buttons was measured at 25° C. after being suspended in PBS for 14 days at 37° C., and the average was reported. The surfaces of the buttons were thoroughly blotted using lint-free blotting paper to remove surface/excess PBS prior to the wet refractive index measurements. The difference in refractive index (ΔRI) is defined as the wet refractive index minus the dry refractive index. For the water content measurements, the dry buttons were weighed and incubated in de-ionized water at 37° C., and the water content was determined by the "Hydration Method" at 7 days and 14 days. For each example, lenses were extracted with methanol, gradient equilibrated with PBS, and analyzed for macro-vacuoles or macro-glistenings by dark field microscopy following the procedure described earlier in "Macro-glistening Test Method". The macro-vacuoles or macro-glistenings were large enough to be counted, and the range of the number of macro-vacuoles or micro-glistenings observed in 4 lenses are shown in Table 13. For each example, lenses were extracted with methanol, dried and analyzed for the micro-glistening density following the procedure described earlier in "Micro-glistening Test Method" The results as determined by dark field microscopy are listed in Table 13.

TABLE 12

|  | Ex. 56 | Ex. 57 | Ex. 58 | Ex. 59 | Ex. 60 | Ex. 61 | Ex. 62 | Ex. 63 |
|---|---|---|---|---|---|---|---|---|
| Components (weight %) | | | | | | | | |
| PEG-OH 360 | 20 | 20 | 19.5 | 19.0 | 20 | 19.65 | 20 | 18 |
| EGDCA | 58.4 | 58 | 58 | 58 | 57 | 57 | 58.4 | 59.4 |
| TCDA | 8.25 | 8.65 | 9.15 | 9.65 | 9.65 | 10 | 8.25 | 9.25 |
| PEA | 12.5 | 12.5 | 12.5 | 12.5 | 12.5 | 12.5 | 12.5 | 12.5 |
| UVB | 0.70 | 0.70 | 0.70 | 0.70 | 0.70 | 0.70 | 0.70 | 0.70 |
| Omnirad 819 | 0.15 | 0.15 | 0.15 | 0.15 | 0.15 | 0.15 | 0.15 | 0.15 |

TABLE 12-continued

|  | Ex. 64 | Ex. 65 | Ex. 66 | Ex. 67 | Ex. 68 | Ex. 69 | Ex. 70 | Ex. 71 |
|---|---|---|---|---|---|---|---|---|
| Components (weight %) | | | | | | | | |
| PEG-OH 360 | 17.5 | 17.0 | 16 | 14 | 12 | 8 | 4 | 0 |
| EGDCA | 59.65 | 59.9 | 60.4 | 63.15 | 65.15 | 69.15 | 73.15 | 77.15 |
| TCDA | 9.5 | 9.75 | 10.25 | 9.5 | 9.5 | 9.5 | 9.5 | 9.5 |
| PEA | 12.5 | 12.5 | 12.5 | 12.5 | 12.5 | 12.5 | 12.5 | 12.5 |
| UVB | 0.70 | 0.70 | 0.70 | 0.70 | 0.70 | 0.70 | 0.70 | 0.70 |
| Omnirad 819 | 0.15 | 0.15 | 0.15 | 0.15 | 0.15 | 0.15 | 0.15 | 0.15 |

TABLE 13

|  | Dry RI[1] | Wet IR[1] Day 14 at 37° | ΔRI | Abbe # (25)[1] | $T_g$ ($1^{st}$, $2^{nd}$ scans) | % WC[2] Day 7, Day 14, At 37° C. | Range in # of Macro-Glistenings per Lens[3] | Micro-Glistening Density (#/mm$^2$)[4] |
|---|---|---|---|---|---|---|---|---|
| Ex. 56 | 1.528565 (0.000305) | 1.518041 (0.000632) | 0.010524 | 48.87 (0.28) | 1.6, 0.5 | 4.17 (0.03), 4.91 (0.03) | 0 | 2.2 (0.8) |
| Ex. 57 | 1.528501 (0.000189) | 1.518271 (0.000317) | 0.010230 | 48.84 (0.90) | 4.1, 3.0 | 4.27 (0.04), 4.99 (0.13) | 0 | 4.5 (1.7) |
| Ex. 58 | 1.528883 (0.000145) | 1.518999 (0.000423) | 0.009884 | 49.24 (0.56) | 3.4, 1.6 | 4.16 (0.02), 4.88 (0.02) | 0 | 6.6 (6.2) |
| Ex 59 | 1.529389 (0.000198) | 1.521356 (0.003561) | 0.008032 | 50.01 (1.51) | 4.9, 2.6 | 3.86 (0.15), 4.50 (0.17) | 0 | 2.2 (1.5) |
| Ex. 60 | 1.528920 (0.000263) | 1.518796 (0.000581) | 0.010124 | 48.63 (1.51) | 3.5, 2.5 | 4.24 (0.04), 4.90 (0.03) | 0 | 4.9 (1.2) |
| Ex. 61 | 1.529030 (0.000054) | 1.520164 (0.000425) | 0.008866 | 48.34 (0.87) | 3.5, 2.0 | 4.05 (0.04), 4.69 (0.01) | 0 | 6.6 (4.7) |
| Ex. 62 | 1.528757 (0.000068) | 1.519120 (0.000365) | 0.009637 | 49.00 (0.31) | 3.3, 1.1 | 4.05 (0.04), 4.70 (0.02) | 0 | 1.4 (1.0) |
| Ex 63 | 1.529983 (0.000042) | 1.521921 (0.000311) | 0.008062 | 49.16 (0.18) | 7.8, 5.7 | 3.41 (0.06), 3.93 (0.03) | ≤1 | 1.6 (0.8) |
| Ex. 64 | 1.529939 (0.000053) | 1.521807 (0.000417) | 0.008131 | 49.02 (0.44) | 8.1, 6.0 | 3.48 (0.02), 4.00 (0.02) | 0 | 0.7 (0.3) |
| Ex. 65 | 1.530455 (0.000060) | 1.522924 (0.000249) | 0.007531 | 49.19 (0.21) | 8.9, 7.9 | 3.25 (0.03), 3.76 (0.05) | ≤1 | 2.1 ((3.0) |
| Ex. 66 | 1.531176 (0.000033) | 1.524325 (0.000117) | 0.006852 | 49.05 (0.56) | 9.7, 8.6 | 2.94 (0.01), 3.41 (0.04) | ≤3 | 1.9 (1.4) |
| Ex 67 | 1.532052 (0.000052) | 1.526254 (0.000425) | 0.005799 | 49.26 (0.94) | 10.0, 8.5 | 2.53 (0.01), 2.92 (0.02) | 10-20 | 4.0 (4.3) |
| Ex. 68 | 1.532988 (0.000180) | 1.532955 (0.000190) | 0.000033 | 48.97 (1.01) | 11.0, 9.5 | 2.14 (0.01), 2.51 (0.07) | 10-15 | 1.3 (0.9) |
| Ex. 69 | 1.535000 (0.000058) | 1.534790 (0.000106) | 0.000210 | 49.10 (0.40) | 16.0, 14.7 | 1.46 (0.03), 1.67 (0.02) | 30-50 | 1.5 ((2.0) |
| Ex. 70 | 1.536779 (0.000185) | 1.536767 (0.000167) | 0.000011 | 48.02 (1.14) | 18.4, 17.2 | 0.89 (0.01), 1.03 (0.05) | >50 | 12.6 (2.6) |
| Ex 71 | 1.538655 (0.000181) | 1.538398 (0.000243) | 0.000257 | 48.01 (0.29) | 21.9, 21.2 | 0.42 (0.02), 0.45 (0.03) | >50 | 2.3 (1.4) |

Figure 6:
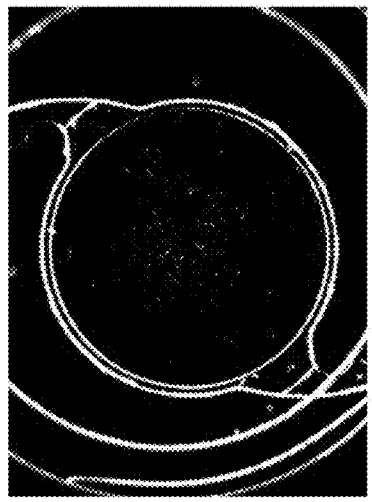
FIG. 6 shows the levels of micro-glistening for examples 66 and 70 by dark field microscopy.
Figure 6:
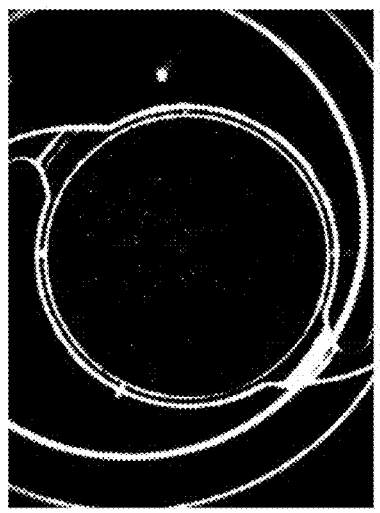
Figure 7:
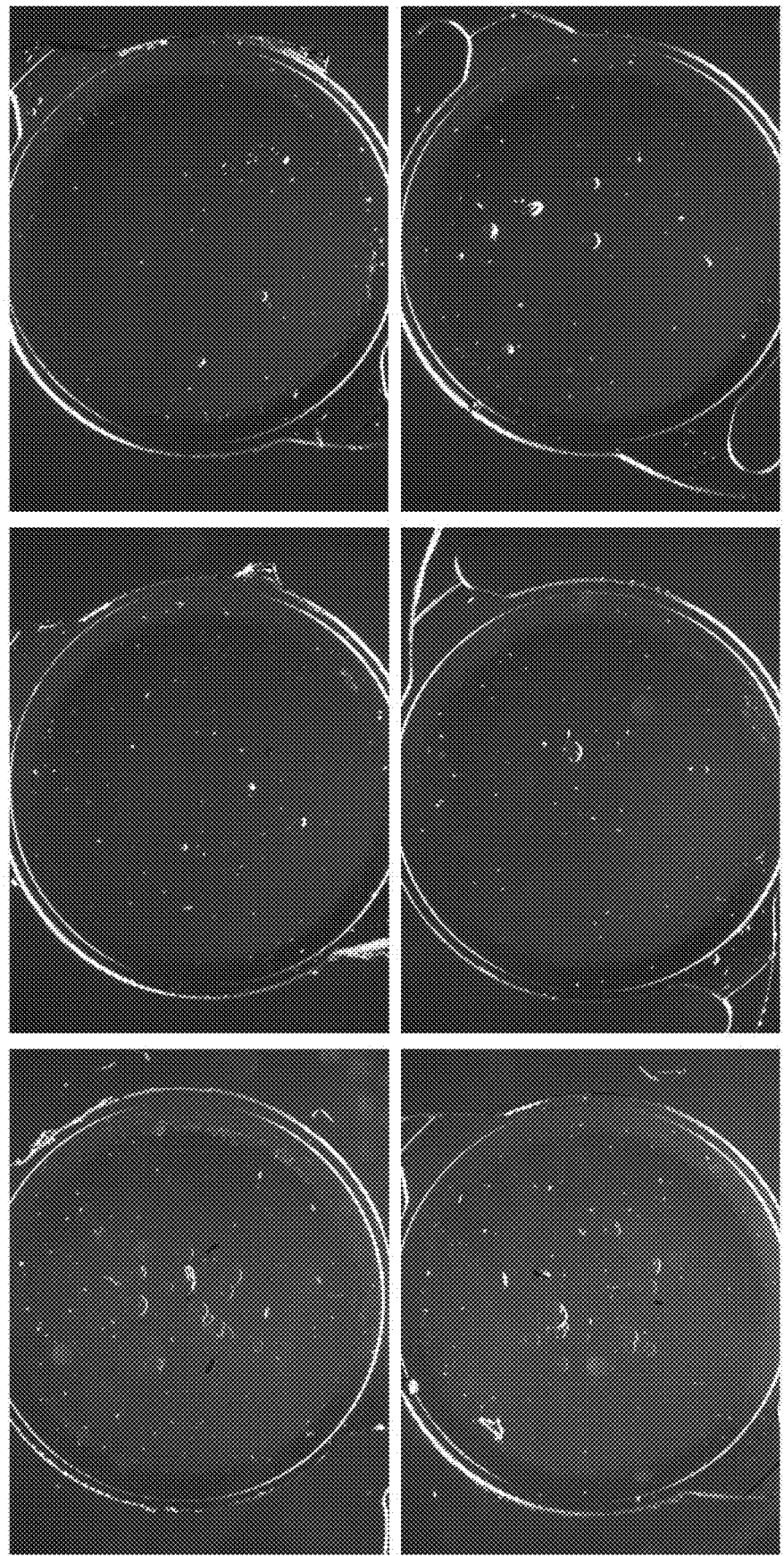
FIG. 7 shows the level of macro-glistening in examples 72-74 by dark field microscopy.
Figure 8:
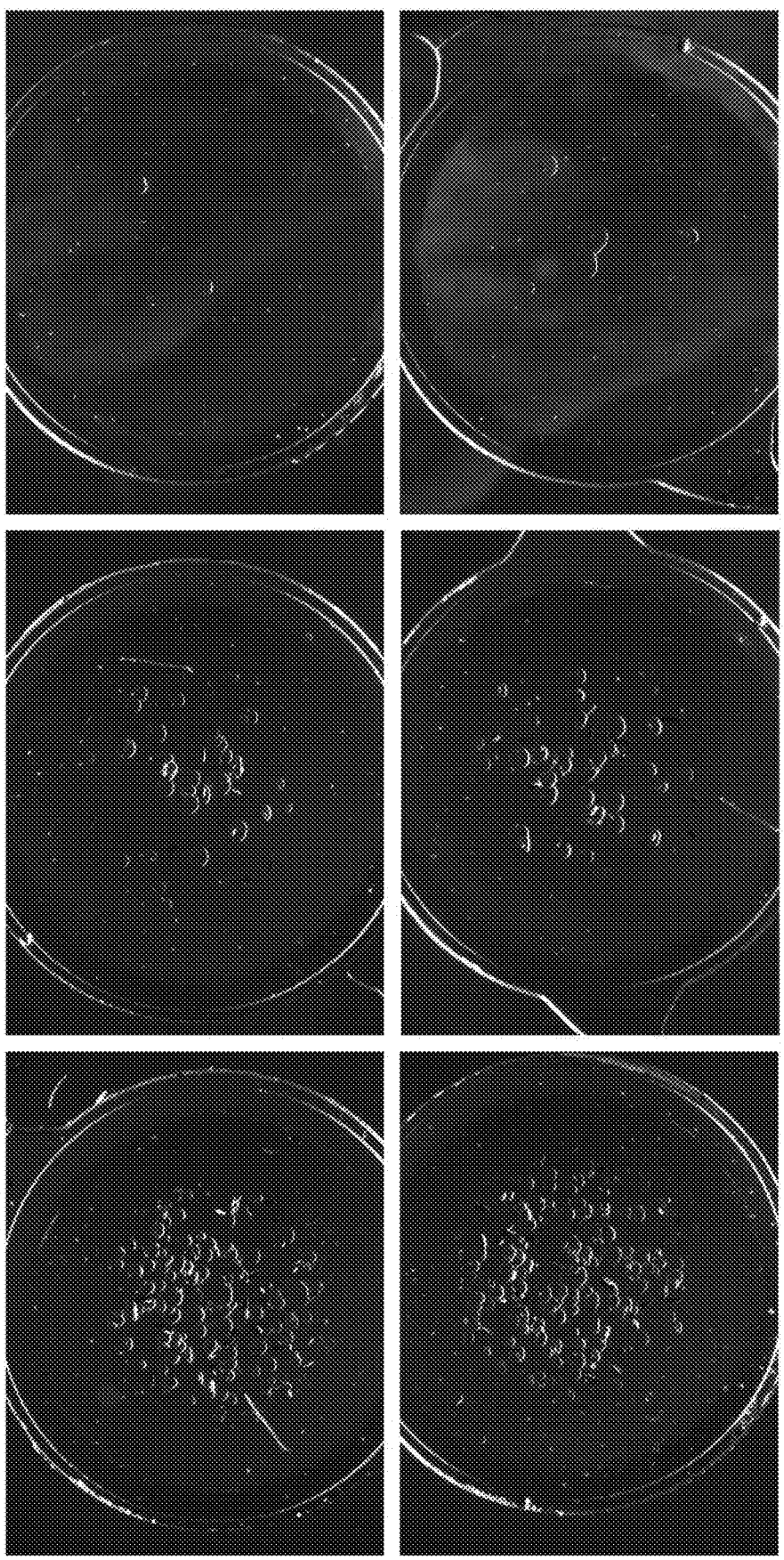
FIG. 8 shows the level of macro-glistening in examples 75-77 by dark field microscopy.
Figure 9:
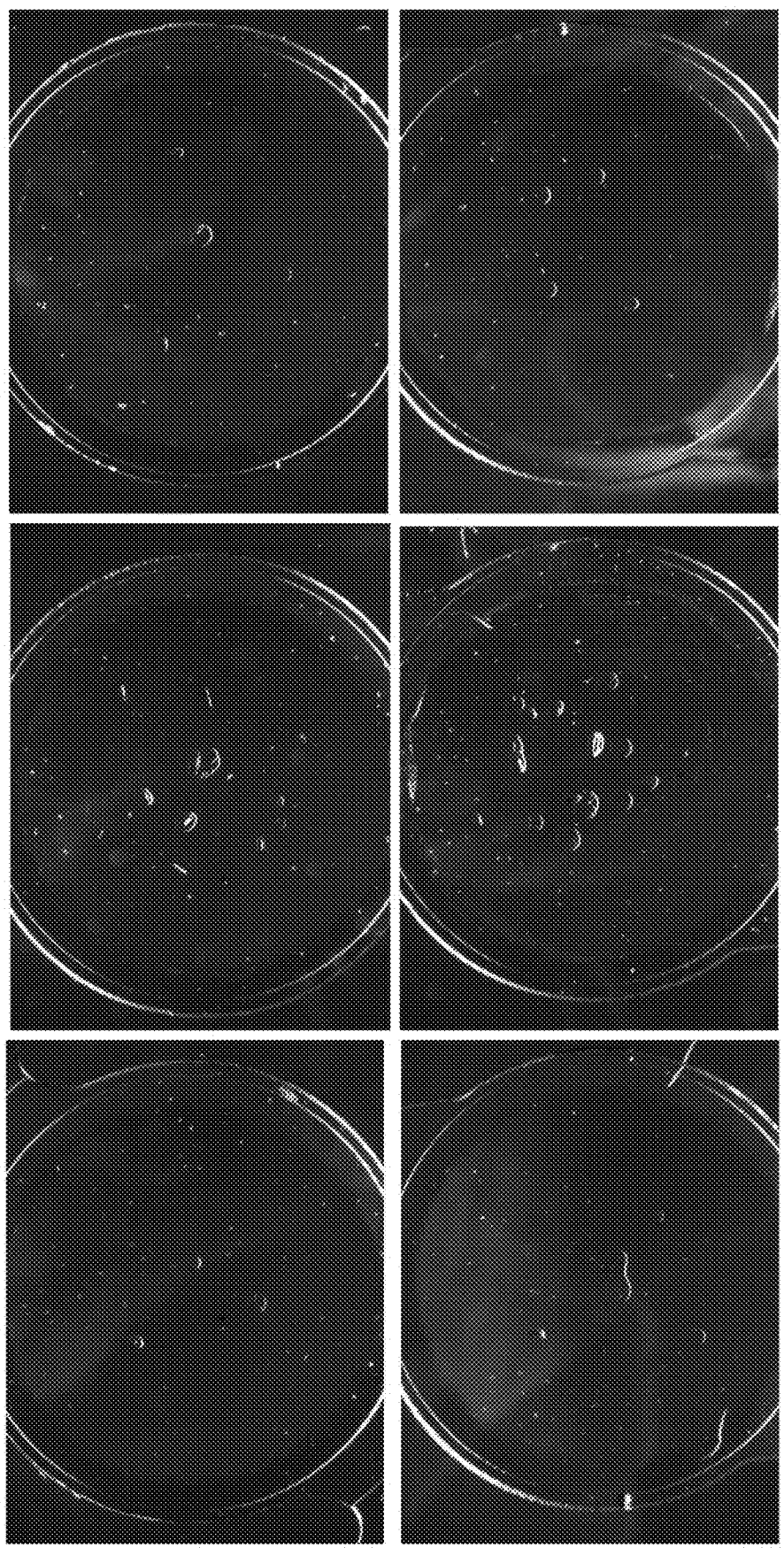
FIG. 9 shows the level of macro-glistening in examples 78-80 by dark field microscopy.
Figure 10:
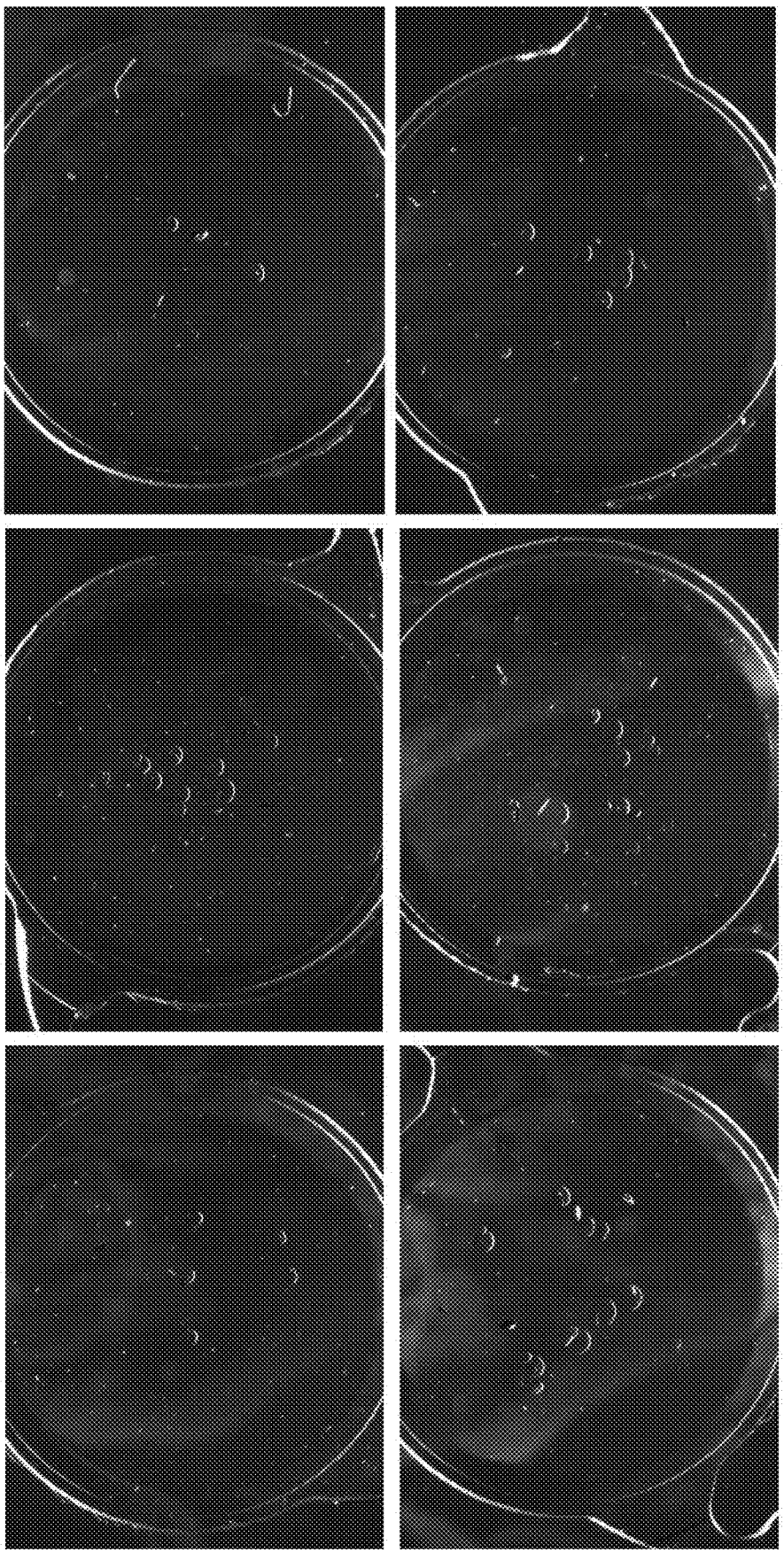
FIG. 10 shows the level of macro-glistening in examples 81-83 by dark field microscopy.
Figure 11:
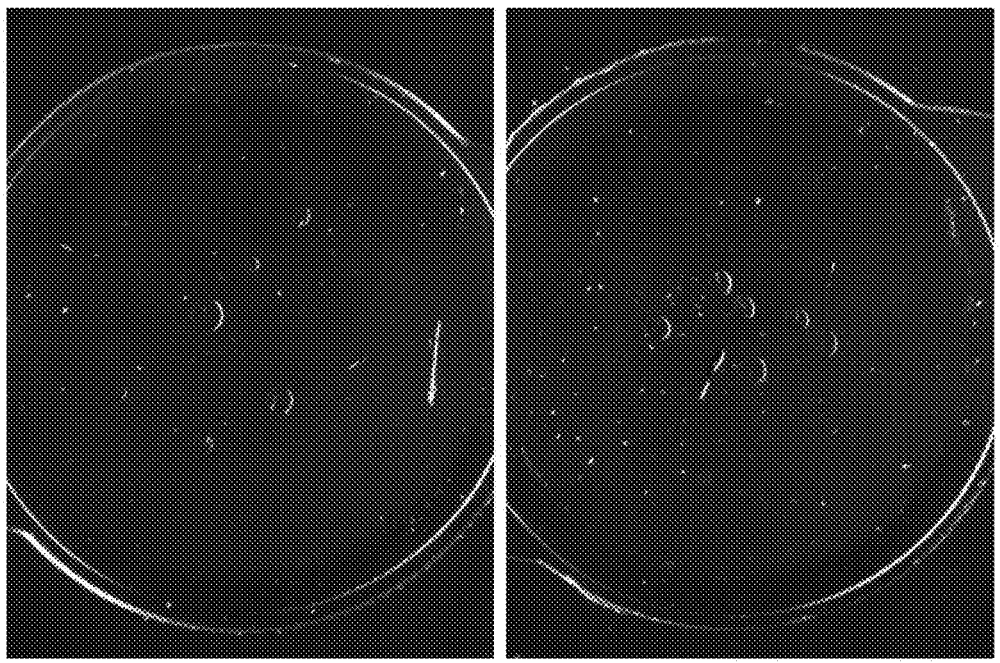
FIG. 11 shows the level of macro-glistening in example 84 by dark field microscopy.

[1]Three buttons, both surfaces measured, average of six measurements
[2]Hydration Method
[3]Four lenses were evaluated
[4]Average density from four lenses For the most part, examples 56-66 showed an excellent balance of properties including refractive indexes over about 1.52 and Abbe numbers greater than about 48, while exhibiting virtually no macro-glistenings and low micro-glistening density. When PEA is replaced with PEMA in the formulation of example 56, the dry RI was 1.528864 (0.000084); the wet RI after 14 days at 37° C. was 1.520183 (0.000694); the ΔRI was 0.008681; the Abbe number at 25° C. was 51.46 (4.99); the % WC at day 7 and day 14, at 37° C. were 3.45 (0.03) and 4.08 (0.04), respectively; the $T_g$ (first and second scans) were 9.7° C. and 6.6° C., respectively; and the range of macro-glistenings per lens was less than one. Dark field micrographs of individual lenses from example 66 having a micro-glistening density of 2.3/mm$^2$ and example 70 having a micro-glistening density of 13.3/mm$^2$ are shown in FIG. 6.

Examples 72-84

Polymer buttons and lenses were prepared from RMM listed in Table 14 according to the procedure for examples 44-51, except that for the polymer buttons only, the light source as TL03 lights having an intensity of 5-6 mW/cm$^2$. For each example, the refractive index, Abbe number, glass transition temperature, and water content were determined and listed in Table 15. The dry refractive index and Abbe number on both surfaces of the polymer buttons were measured at 25° C. and the average was reported. The wet refractive index on both surfaces of the polymer buttons was measured at 25° C. after being suspended in PBS for 14 days at 37° C., and the average was reported. The surfaces of the polymer buttons were thoroughly blotted using lint-free blotting paper to remove surface/excess PBS prior to the wet refractive index measurements. The difference in refractive index ($\Delta$RI) is defined as the wet refractive index minus the dry refractive index. For the water content measurements, the dry polymer buttons were weighed and incubated in de-ionized water at 37° C., and the water content was determined by the "Hydration Method" at 7 days and 14 days. For each example, four lenses were extracted with methanol, gradient equilibrated with PBS, and analyzed for macro-vacuoles or macro-glistenings following the procedure described earlier in "Macro-glistening Test Method". The dark field micrographs of lenses with the lowest and highest number of macro-vacuoles or macro-glistenings for each example are shown in FIGS. 7-11. Lenses from examples 72-74 were incubated for 3 days in PBS at 37° C., whereas lenses from examples 75-84 were incubated for 5 days in PBS at 37° C. The macro-vacuoles or macro-glistenings were large enough to be counted, and the range of the number of macro-vacuoles observed in 4 lenses are listed in Table 15.

TABLE 14

| | Ex. 72 | Ex. 73 | Ex. 74 | Ex. 75 | Ex. 76 | Ex. 77 | Ex. 78 | Ex. 79 | Ex. 80 |
|---|---|---|---|---|---|---|---|---|---|
| Components (weight %) | | | | | | | | | |
| PEG-OH 360 | 14 | 15 | 16 | 14 | 14 | 15 | 15 | 15 | 0 |
| PEG-OH 200 | 0 | 0 | 0 | 0 | 0 | 0 | 0 | 0 | 15 |
| HEMA | 4 | 4 | 4 | 5 | 6 | 5 | 6 | 6 | 6 |
| EGDCA | 62.4 | 61.4 | 61.4 | 61.4 | 60.4 | 60.4 | 59.4 | 59.4 | 59.4 |
| TCDA | 6.25 | 6.25 | 6.25 | 6.25 | 6.25 | 6.25 | 6.25 | 6.25 | 6.25 |
| PPA | 12.5 | 12.5 | 12.5 | 12.5 | 12.5 | 12.5 | 12.5 | 0 | 0 |
| PEA | 0 | 0 | 0 | 0 | 0 | 0 | 0 | 12.5 | 12.5 |
| UVB | 0.7 | 0.7 | 0.7 | 0.7 | 0.7 | 0.7 | 0.7 | 0.7 | 0.7 |
| Omnirad 819 | 0.15 | 0.15 | 0.15 | 0.15 | 0.15 | 0.15 | 0.15 | 0.15 | 0.15 |

| | Ex. 81 | Ex. 82 | Ex. 83 | Ex. 84 |
|---|---|---|---|---|
| Components (weight %) | | | | |
| PEG-OH 360 | 15 | 15 | 15 | 0 |
| PEG-OH 200 | 0 | 0 | 0 | 15 |
| HEMA | 6 | 6 | 6 | 6 |
| EGDCA | 59.4 | 59.4 | 59.4 | 59.4 |
| TCDA | 6.25 | 6.25 | 6.25 | 6.25 |
| CHA | 12.5 | 0 | 0 | 0 |
| CHMA | 0 | 12.5 | 0 | 0 |
| CHEA | 0 | 0 | 12.5 | 12.5 |
| UVB | 0.7 | 0.7 | 0.7 | 0.7 |
| Omnirad 819 | 0.15 | 0.15 | 0.15 | 0.15 |

TABLE 15

| | Dry RI[1] | Wet RI[1] Day 14 | $\Delta$RI | Abbe # (25)[1] | $T_g$ ($1^{st}$, $2^{nd}$ scans) | % WC[2] Day 7, Day 14 At 37° C. | Range in # of Macro-Glistenings per Lens[3] |
|---|---|---|---|---|---|---|---|
| Ex. 72 | 1.529262 (0.000129) | 1.523412 (0.001836) | 0.005850 | 49.55 (0.67) | 1.9, 0.7 | 3.26 (0.09), 3.65 (0.09) | 12-18 |
| Ex. 73 | 1.528845 (0.000027) | 1.521992 (0.001574) | 0.006853 | 49.32 (0.54) | 2.6, 1.1 | 3.56 (0.05), 4.08 (0.09) | 2-5 |
| Ex. 74 | 1.528999 (0.000085) | 1.521973 (0.001536) | 0.007026 | 49.45 (0.65) | 2.7, 1.2 | 3.76 (0.15), 4.13 (0.15) | 4-10 |
| Ex. 75 | 1.529274 (0.000119) | 1.522272 (0.001469) | 0.007002 | 49.91 (1.00) | 2.1, 0.5 | 3.21 (0.07), 3.81 (0.19) | >50 |
| Ex. 76 | 1.529212 (0.000112) | 1.521902 (0.001299) | 0.007310 | 49.36 (0.33) | 1.9, 0.4 | 3.68 (0.05), 4.12 (0.07) | 30-40 |
| Ex. 77 | 1.528887 (0.000112) | 1.521444 (0.001569) | 0.007443 | 48.96 (0.80) | 4.5, 3.1 | 3.85 (0.03), 4.36 (0.02) | 2-5 |
| Ex. 78 | 1.528457 (0.000349) | 1.520182 (0.001691) | 0.008275 | 50.34 (1.74) | 3.4, 2.3 | 4.12 (0.02), 4.66 (0.01) | 3-5 |
| Ex. 79 | 1.529505 (0.000101) | 1.521734 (0.001973) | 0.007771 | 49.22 (0.81) | 6.5, 4.8 | 4.27 (0.01), 4.74 (0.05) | 10-17 |
| Ex. 80 | 1.528683 (0.000174) | 1.521098 (0.002100) | 0.007586 | 50.26 (0.88) | 1.9, 0.4 | 4.13 (0.01), 4.61 (0.01) | 4-5 |
| Ex. 81 | 1.522395 (0.000760) | 1.514011 (0.001387) | 0.008383 | 52.02 (1.50) | 8.2, 5.8 | 4.29 (0.04), 4.79 (0.02) | 6-15 |
| Ex. 82 | 1.523441 (0.000095) | 1.513080 (0.002679) | 0.010360 | 51.96 (0.83) | 0.7, −0.4 | 4.61 (0.04), 5.02 (0.02) | 12-15 |

TABLE 15-continued

|  | Dry RI[1] | Wet RI[1] Day 14 | ΔRI | Abbe # (25)[1] | $T_g$ (1st, 2nd scans) | % WC[2] Day 7, Day 14 At 37° C. | Range in # of Macro-Glistenings per Lens[3] |
|---|---|---|---|---|---|---|---|
| Ex. 83 | 1.522907 (0.000181) | 1.514065 (0.001707) | 0.008842 | 53.10 (1.14) | 2.3, 1.0 | 4.40 (0.01), 4.84 (0.04) | 5-10 |
| Ex. 84 | 1.522877 (0.000109) | 1.511672 (0.000190) | 0.011205 | 51.72 (1.02) | −4.0, −4.8 | 4.19 (0.05), 4.56 (0.06) | 5-10 |

[1]Three polymer buttons, both surfaces measured, average of six measurements
[2]Drying Method
[3]Four Lenses In examples 72-84, formulations having between 14-16 weight percent PEG-OH 360 and 4-6 weight percent HEMA exhibited a low level of macro-glistenings as shown in FIGS. 7-11.

Examples 85-88

Under yellow lighting, the RMMs listed in Table 16 were degassed by sparging with nitrogen gas for at least 3 minutes, back filling the head-space with nitrogen gas, and then immediately transferred into a fill box having a nitrogen gas atmosphere with less than 0.1% (v/v) oxygen gas and an internal temperature at ambient temperature. About 350 microliters of RMM were dispensed inside an O-ring that is placed between two glass plates and held together with clamps, then the apparatus transferred into a cure box held at a temperature between 55° C. and 60° C. and then cured using TL03 lights having an intensity of 3-4 mW/cm² for 15 minutes followed by TL03 lights having an intensity of 6-7 mW/cm² for another 15 minutes. The cured assemblies were manually demolded. All polymer buttons were transparent and not tacky. All polymer buttons were not extracted with any solvent. For each example, the dry refractive index, the wet refractive index, Abbe number, and water content were determined and listed in Table 17.

The dry refractive index and Abbe number on both surfaces of the polymer buttons were measured at 25° C., and the average was reported. The wet refractive index on both surfaces of the polymer buttons was measured at 25° C. after being suspended in PBS for 7 days at 37° C., and the average was reported. The surfaces of the polymer buttons were thoroughly blotted using lint-free blotting paper to remove surface/excess PBS prior to the wet refractive index measurements. The difference in refractive index (ΔRI) is defined as the wet refractive index minus the dry refractive index. For water content measurement, polymer buttons were incubated in PBS at 37° C. for 7 days, and the water content was subsequently determined using the "Drying Method" described earlier.

TABLE 16

| Components (weight %) | Ex. 85 | Ex. 86 | Ex. 87 | Ex. 88 |
|---|---|---|---|---|
| EGDCA | 57.35 | 54.48 | 51.62 | 47.60 |
| PEG-OH 360 | 22 | 25.90 | 29.80 | 35.26 |
| PEMA | 12.5 | 11.88 | 11.25 | 10.38 |
| TCDA | 8 | 7.60 | 7.20 | 6.64 |
| Omnirad 819 | 0.15 | 0.14 | 0.14 | 0.12 |

TABLE 17

|  | Dry RI[1] | Wet RI[1] Day 7, 37° | ΔRI | Abbe # (25)[1] | % WC[2] |
|---|---|---|---|---|---|
| Ex. 85 | 1.526492 (0.010028) | 1.516464 (0.002089) | 0.010028 | 49.88 (0.68) | 5.09 (0.06) |
| Ex. 86 | 1.524288 (0.012844) | 1.511445 (0.001745) | 0.012844 | 51.00 (1.13) | 7.07 (0.03) |
| Ex. 77 | 1.522042 (0.000070) | 1.505598 (0.000576) | 0.016444 | 52.09 (1.86) | 9.57 (0.17) |
| Ex. 88 | 1.518925 (0.000275) | 1.498656 (0.000496) | 0.020269 | 51.45 (2.81) | 12.34 (0.99) |

[1]Three polymer buttons, both surfaces measured, average of six measurements
[2]Drying Method Clauses For reasons of completeness, various aspects of the disclosure are set forth in the following numbered clauses.

Clause 1. A composition made by free radical polymerization of a reactive monomer mixture comprising:
  a. at least one hydrophobic monomer;
  b. at least one monomer selected from hydrophilic monomers and hydroxyalkyl (meth)acrylate monomers, and any combinations thereof; and
  c. a tricyclo[5.2.1.0²,⁶]decanedimethanol di(meth)acrylate cross-linking agent;
  wherein the composition exhibits a refractive index of at least 1.45 and an Abbe number of at least 39 Clause 2. The composition of clause 1, wherein the hydrophobic monomer is a hydrophobic (meth)acrylate monomer.

Clause 3. The composition of clause 2, wherein the hydrophobic (meth)acrylate is selected from an aliphatic (meth)acrylate, an aromatic (meth)acrylate, a cycloaliphatic (meth)acrylate, and any combination thereof.

Clause 4. The composition of clause 3, wherein the hydrophobic (meth)acrylate is a cycloaliphatic (meth)acrylate.

Clause 5. The composition of clause 4, wherein the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth)acrylate, isobornyl derivatives, norbornyl derivatives, ((1R,2S,4R)-bicyclo [2.2.1]hept-5-en-2-yl)methyl (meth)acrylate, ethylene glycol dicyclopentenyl ether (meth)acrylate, poly(ethylene) glycol dicyclopentenyl ether (meth)acrylate, 2-(((3aR,4R, 5S,7R,7aR)-octahydro-1H-4,7-methanoinden-5-yl)oxy) ethyl acrylate, 2-(((3aS,4R,6S,7R,7aR)-3a,4,5,6,7,7ahexahydro-1H-4,7-methanoinden-6-yl)oxy)ethyl acrylate, (3 aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R, 3S, 5f, 7r)-2-methyladamantan-2-yl (meth)acrylate, (1R,3S,5f,7r)-2-methyladamantan-2-yl PEG (meth)acrylate derivates and (1R, 3S, 5f, 7r)-2-methyladamantan-2-yl (meth)acrylate derivatives, and any combination thereof.

Clause 6. The composition of clause 5, wherein the cycloaliphatic (meth)acrylate is selected from cyclohexyl acrylate, cyclohexylmethyl acrylate, cyclohexylmethyl methacrylate, 2-cyclohexylethyl acrylate, 2-cyclohexylethyl methacrylate, ethylene glycol dicyclopentenyl ether (meth)acrylate, and any combination thereof.

Clause 7. The composition of clause 6, wherein the cycloaliphatic (meth)acrylate is ethylene glycol dicyclopentenyl ether (meth)acrylate.

Clause 8. The composition of any one of clauses 4-7, wherein the reactive monomer mixture comprises the cycloaliphatic (meth)acrylate in an amount between about 40 and about 90 weight percent, between about 50 and about 80 weight percent, or between about 50 and about 70 weight percent.

Clause 9. The composition of clause 3, wherein the hydrophobic (meth)acrylate is an aliphatic (meth)acrylate.

Clause 10. The composition of clause 9, wherein the aliphatic (meth)acrylate is a $C_1$-$C_{18}$ alkyl (meth)acrylate.

Clause 11. The composition of clause 10, wherein the $C_1$-$C_{18}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof.

Clause 12. The composition of clause 11, wherein the $C_1$-$C_{18}$ alkyl (meth)acrylate is n-hexyl acrylate.

Clause 13. The composition of any one of clauses 9-12, wherein the reactive monomer mixture comprises the aliphatic (meth)acrylate in an amount between about 1 and about 20 weight percent, or between about 1 and about 10 weight percent.

Clause 14. The composition of clause 3, wherein the hydrophobic (meth)acrylate is an aromatic (meth)acrylate.

Clause 15. The composition of clause 14, wherein the aromatic (meth)acrylate is selected from the group consisting of 2-phenylethyl (meth)acrylate, 2-phenoxyethyl (meth)acrylate, 4-chlorophenoxyethyl (meth)acrylate, 3-phenylpropyl (meth)acrylate, 4-phenylbutyl (meth)acrylate, 3-phenoxypropyl (meth)acrylate, 1,3-bis-phenylthiol-2-propyl (meth)acrylate, poly(ethylene glycol) phenyl ether (meth)acrylate, and any combination thereof.

Clause 16. The composition of clause 15, wherein the aromatic (meth)acrylate is 2-phenylethyl acrylate.

Clause 17. The composition of clause 15, wherein the aromatic (meth)acrylate is 2-phenylethyl methacrylate.

Clause 18. The composition of clause 15, wherein the aromatic (meth)acrylate is a combination of 2-phenylethyl acrylate and 2-phenylethyl methacrylate.

Clause 19. The composition of clause 15, wherein the aromatic (meth)acrylate is a combination of 2-phenylethyl methacrylate and 3-phenylpropyl acrylate.

Clause 20. The composition of any one of clauses 14-19, wherein the reactive monomer mixture comprises the aromatic (meth)acrylate in an amount between about 7 and about 25 weight percent, between about 10 and about 20 weight percent, or between about 12 and about 15 weight percent.

Clause 21. The composition of any one of clauses 1-20, wherein the reactive monomer mixture comprises at least one hydrophilic monomer.

Clause 22. The composition of clause 21, wherein the at least one hydrophilic monomer is selected from vinyl pyrrolidone, N-vinyl N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl)acrylamide, N-(2-hydroxyethyl)(meth)acrylamide, N-(2-hydroxypropyl)(meth)acrylamide, N-(3-hydroxypropyl)(meth)acrylamide, poly(ethylene glycol) methyl ether (meth)acrylate, poly(ethylene glycol) (meth)acrylate, and any combination thereof.

Clause 23. The composition of clause 22, wherein the at least one hydrophilic monomer is a poly(ethylene glycol)-containing monomer.

Clause 24. The composition of clause 23, wherein the poly(ethylene glycol)-containing monomer is selected from poly(ethylene glycol) methacrylate and poly(ethylene glycol) methyl ether methacrylate, and a combination thereof.

Clause 25. The composition of clause 23 or clause 24, wherein the poly(ethylene glycol)-containing monomer has a number-average molecular weight ($M_n$) of about 200 g/mol to about 1000 g/mol, or about 200 g/mol to about 400 g/mol.

Clause 26. The composition of clause 23, wherein the poly(ethylene glycol)-containing monomer has formula:

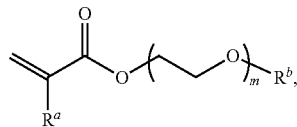

wherein $R^a$ and $R^b$ are each independently selected from hydrogen and methyl, and m is an integer from 2 to 25.

Clause 27. The composition of clause 26, wherein $R^a$ is methyl and $R^b$ is hydrogen.

Clause 28. The composition of any one of clauses 26 and 27, wherein m is an integer from 2 to 8.

Clause 29. The composition of any one of clauses 1-28, wherein the reactive monomer mixture comprises the at least one hydrophilic monomer in an amount between about 1 and about 40 weight percent, between about 10 and about 30 weight percent, between about 12 and about 22 weight percent, or between about 14 and about 20 weight percent.

Clause 30. The composition of any one of clauses 1-29, wherein the reactive monomer mixture comprises at least one hydroxyalkyl (meth)acrylate monomer.

Clause 31. The composition of clause 30, wherein the hydroxyalkyl (meth)acrylate monomer is selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

Clause 32. The composition of clause 31, wherein the hydroxyalkyl (meth)acrylate monomer is 2-hydroxyethyl methacrylate.

Clause 33. The composition of any one of clauses 1-32, wherein the reactive monomer mixture comprises the at least one hydroxyalkyl (meth)acrylate monomer in an amount about 1 and about 10 weight percent, between about 2 and about 8 weight percent, or between about 4 and about 6 weight percent.

Clause 34. The composition of any one of clauses 1-33, wherein the reactive monomer mixture comprises a combination of a hydrophilic monomer and a hydroxyalkyl (meth)acrylate monomer.

Clause 35. The composition of clause 34, wherein the hydrophilic monomer is a poly(ethylene glycol)-containing (meth)acrylate monomer and the hydroxyalkyl (meth)acrylate monomer is 2-hydroxyethyl (meth)acrylate Clause 36. The composition of clause 35, wherein the hydrophilic monomer is selected from poly(ethylene glycol) methacrylate and poly(ethylene glycol) methyl ether methacrylate, and the hydroxyalkyl (meth)acrylate monomer is 2-hydroxyethyl acrylate.

Clause 37. The composition of any one of clauses 1-36, wherein the tricyclo[$5.2.1.0^{2,6}$]decanedimethanol di(meth)acrylate cross-linking agent is tricyclo[$5.2.1.0^{2,6}$]decanedimethanol diacrylate.

Clause 38. The composition of any one of clauses 1-37, wherein the reactive monomer mixture comprises the tricyclo[$5.2.1.0^{2,6}$]decanedimethanol di(meth)acrylate cross-linking agent in an amount between about 1 and about 20 weight percent, between about 3 and about 15 weight percent, or between about 3 and about 10 weight percent.

Clause 39. The composition of any one of clauses 1-38, wherein: the hydrophobic monomer is ethylene glycol dicyclopentenyl ether (meth)acrylate; the hydrophilic monomer is selected from the group consisting of poly(ethylene glycol) methacrylate, poly(ethylene glycol) methyl ether methacrylate, 2-hydroxyethyl methacrylate, and any combination thereof; and the crosslinking agent is tricyclo[$5.2.1.0^{2,6}$] decanedimethanol diacrylate.

Clause 40. The composition of any of clauses 1-39, wherein the reactive monomer mixture further comprises a polyamide.

Clause 41. The composition of clause 40, wherein the polyamide is selected from poly(vinyl pyrrolidone), poly(N-vinyl-N-methyl acetamide), poly(N-vinyl acetamide), poly(dimethyl acrylamide), and a copolymer or a mixture thereof.

Clause 42. The composition of clause 41, wherein the polyamide is poly(vinyl pyrrolidone).

Clause 43. The composition of clause 40, wherein the polyamide is a copolymer.

Clause 44. The composition of any one of clauses 40-43, wherein the reactive monomer mixture comprises the polyamide in an amount between about 0.1 weight percent and about 5 weight percent, between about 0.5 weight percent and about 3 weight percent, or between about 0.5 weight percent and about 2 weight percent.

Clause 45. The composition of any one of clauses 1-44, further comprising at least one UV/HEV absorbing compound in the reactive monomer mixture.

Clause 46. The composition of clause 45, wherein the UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido) ethyl methacrylate, 2-(2-cyano-2-(9H-xanthen-9-ylidene) acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof.

Clause 47. The composition of clause 45 or clause 46, wherein the reactive monomer mixture comprises the UV/HEV absorbing compound in an amount between about 0.1 and about 5 weight percent, between about 1 and about 4 weight percent, or between about 1 and about 3 weight percent.

Clause 48. The composition of any one of clauses 1-47, further comprising at least one diluent in the reactive monomer mixture.

Clause 49. The composition of any one of clauses 1-48, having a water content of between about 0 weight percent and about 15 weight percent, between about 1 weight percent and about 10 weight percent, or between about 1 weight percent and about 8 weight percent.

Clause 50. The composition of any one of clauses 1-49, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 51. The composition of any one of clauses 1-50, wherein the free radical polymerization is a photopolymerization using a bisacylphosphine oxide initiator.

Clause 52. An ophthalmic device comprising the composition of any one of clauses 1-51.

Clause 53. The ophthalmic device of clause 52 wherein the ophthalmic device comprises an intraocular lens, contact lens, corneal inlay, corneal outlay, or corneal insert.

Clause 54. The ophthalmic device of clause 53, wherein the ophthalmic device comprises an intraocular lens.

Clause 55. A method for making an ophthalmic device, the method comprising:
  a. providing a composition of any one of clauses 1-51; and
  b. forming an ophthalmic device.

Clause 56. The method of clause 55, further comprising the step of extracting the ophthalmic device with a solvent.

Clause 57. The method of clause 56, further comprising the step of hydrating the extracted ophthalmic device with at least one aqueous solution.

Clause 58. A method for making an ophthalmic device, the method comprising:
  a. preparing a blank from the composition any of clauses 1-51;
  b. machining an ophthalmic device from the blank.

Clause 59. The method of clause 58, further comprising the step of extracting the ophthalmic device with a solvent.

Clause 60. The method of clause 59, further comprising the step of hydrating the extracted ophthalmic device with at least one aqueous solution.

Clause 61. The method of any one of clauses 55-60, further comprising an irradiation step using a femtosecond two photon laser.

Clause 62. The method of any of clauses 55-61, further comprising a step of sterilizing the ophthalmic device.

Clause 63. A method for making an ophthalmic device, the method comprising molding the device from the composition any of clauses 1-51.

Clause 64. A composition made by free radical polymerization of a reactive monomer mixture comprising:
  a. at least one cycloaliphatic (meth)acrylate monomer containing more than one cycloaliphatic ring;
  b. at least one monomer selected from hydrophilic monomers and hydroxyalkyl (meth)acrylate monomers, and any combination thereof;
  c. at least one cross-linking agent;
  wherein the composition exhibits a refractive index of at least 1.45 and an Abbe number of at least 39.

Clause 65. The composition of clause 64, wherein the at least one cycloaliphatic (meth)acrylate monomer containing more than one cycloaliphatic ring comprises two or more separate monocyclic cycloaliphatic rings, or a single bicyclic, tricyclic, bridged, fused, and/or spirocyclic cycloaliphatic ring system.

Clause 66. The composition of clause 64 or clause 65, wherein the at least one cycloaliphatic (meth)acrylate monomer containing more than one cycloaliphatic ring is selected from norbornyl (meth)acrylate, isobornyl (meth)acrylate, isobornyl derivatives, norbornyl derivatives, ((1R,2S,4R)-bicyclo[2.2.1]hept-5-en-2-yl)methyl (meth)acrylate, ethylene glycol dicyclopentenyl ether (meth)acrylate, poly(ethylene) glycol dicyclopentenyl ether (meth)acrylate, 2,2-bis (cyclopent-1-en-1-yloxy)ethyl (meth)acrylate, 2-(((3aR,4R,5S,7R,7aR)-octahydro-1H-4,7-methanoinden-5-yl)oxy) ethyl acrylate, 2-(((3aS,4R,6S,7R,7aR)-3a,4,5,6,7,7a-hexahydro-1H-4,7-methanoinden-6-yl)oxy)ethyl acrylate, (3aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R,3S,5f,7r)-2-methyladamantan-2-yl (meth)acrylate, (1R,3S,5f,7r)-2-methyladamantan-2-yl PEG (meth)acrylate derivates and (1R,3S,5f,7r)-2-methyladamantan-2-yl (meth)acrylate derivatives, and any combination thereof.

Clause 67. The composition of any one of clauses 64-66, wherein the at least one cycloaliphatic (meth)acrylate monomer containing more than one cycloaliphatic ring is ethylene glycol dicyclopentenyl ether acrylate.

Clause 68. The composition of any one of clauses 64-67, wherein the reactive monomer mixture comprises the at least one cycloaliphatic (meth)acrylate monomer containing more than one cycloaliphatic ring in an amount between about 40 and about 90 weight percent, between about 50 and about 80 weight percent, or between about 50 and about 70 weight percent.

Clause 69. The composition of any one of clauses 64-68, wherein the reactive monomer mixture comprises at least one hydrophilic monomer.

Clause 70. The composition of clause 69, wherein the at least one hydrophilic monomer is selected from vinyl pyrrolidone, N-vinyl N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl)acrylamide, N-(2-hydroxyethyl)(meth)acrylamide, N-(2-hydroxypropyl)(meth)acrylamide, N-(3-hydroxypropyl)(meth)acrylamide, poly(ethylene glycol) methyl ether (meth)acrylate, poly(ethylene glycol) (meth)acrylate, and any combination thereof.

Clause 71. The composition of clause 69, wherein the at least one hydrophilic monomer is a poly(ethylene glycol)-containing monomer.

Clause 72. The composition of clause 71, wherein the poly(ethylene glycol)-containing monomer is selected from poly(ethylene glycol) methacrylate and poly(ethylene glycol) methyl ether methacrylate, and a combination thereof.

Clause 73. The composition of clause 71 or clause 72, wherein the poly(ethylene glycol)-containing monomer has a number-average molecular weight ($M_n$) of about 200 g/mol to about 1000 g/mol, or about 200 g/mol to about 400 g/mol.

Clause 74. The composition of clause 71, wherein the poly(ethylene glycol)-containing monomer has formula:

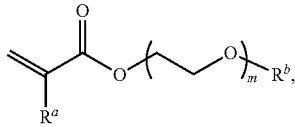

wherein $R^a$ and $R^b$ are each independently selected from hydrogen and methyl, and m is an integer from 2 to 25.

Clause 75. The composition of clause 74, wherein $R^a$ is methyl and $R^b$ is hydrogen.

Clause 76. The composition of any one of clauses 74 and 75, wherein m is an integer from 2 to 8.

Clause 77. The composition of any one of clauses 64-76, wherein the reactive monomer mixture comprises the at least one hydrophilic monomer in an amount between about 1 and about 40 weight percent, between about 10 and about 30 weight percent, between about 12 and about 22 weight percent, or between about 14 and about 20 weight percent.

Clause 78. The composition of any one of clauses 64-77, wherein the reactive monomer mixture comprises at least one hydroxyalkyl (meth)acrylate monomer.

Clause 79. The composition of clause 78, wherein the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

Clause 80. The composition of clause 79, wherein the hydroxyalkyl (meth)acrylate monomer is 2-hydroxyethyl methacrylate.

Clause 81. The composition of any one of clauses 64-80, wherein the reactive monomer mixture comprises the at least one hydroxyalkyl (meth)acrylate monomer in an amount about 1 and about 10 weight percent, between about 2 and about 8 weight percent, or between about 4 and about 6 weight percent.

Clause 82. The composition of any one of clauses 64-81, wherein the reactive monomer mixture comprises a combination of a hydrophilic monomer and a hydroxyalkyl (meth)acrylate monomer.

Clause 83. The composition of clause 82, wherein the hydrophilic monomer is a poly(ethylene glycol)-containing (meth)acrylate monomer and the hydroxyalkyl (meth)acrylate monomer is 2-hydroxyethyl (meth)acrylate.

Clause 84. The composition of clause 83, wherein the hydrophilic monomer is selected from poly(ethylene glycol) methacrylate and poly(ethylene glycol) methyl ether methacrylate, and the hydroxyalkyl (meth)acrylate monomer is 2-hydroxyethyl acrylate.

Clause 85. The composition of any one of clauses 64-84, wherein the at least one cycloaliphatic (meth)acrylate monomer containing more than one cycloaliphatic ring is ethylene glycol dicyclopentenyl ether acrylate, and the at least one hydrophilic monomer is selected from poly(ethylene glycol) methacrylate and poly(ethylene glycol) methyl ether methacrylate.

Clause 86. The composition of any one of clauses 64-85, wherein the reactive monomer mixture further comprises at least one cycloaliphatic (meth)acrylate containing one cycloaliphatic ring.

Clause 87. The composition of clause 86, wherein the cycloaliphatic (meth)acrylate containing one cycloaliphatic ring has at least one cycloaliphatic group comprising at least one carbon-carbon double bond.

Clause 88. The composition of clause 86, wherein the cycloaliphatic (meth)acrylate containing one cycloaliphatic ring is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, and any combination thereof.

Clause 89. The composition of clause 88, wherein the cycloaliphatic (meth)acrylate containing one cycloaliphatic ring is selected from cyclohexyl acrylate, cyclohexylmethyl acrylate, 2-cyclohexylethyl acrylate, 2-cyclohexylethyl methacrylate, 3-cyclohexylpropyl acrylate, and any combination thereof.

Clause 90. The composition of any one of clauses 86-89, wherein the reactive monomer mixture comprises the cycloaliphatic (meth)acrylate containing one cycloaliphatic ring in amount between about 10 and about 25 weight percent, between about 10 and about 20 weight percent, or between about 12 and about 15 weight percent.

Clause 91. The composition of any one of clauses 64-90, wherein the reactive monomer mixture further comprises at least one aromatic (meth)acrylate.

Clause 92. The composition of clause 91, wherein the at least one aromatic (meth)acrylate is selected from 2-phenylethyl (meth)acrylate, 2-phenoxyethyl (meth)acrylate, 3-phenylpropyl (meth)acrylate, 4-phenylbutyl (meth)acrylate, 3-phenoxypropyl (meth)acrylate, 1,3-bis(phenylthio)-2-propyl (meth)acrylate, poly(ethylene glycol) phenyl ether (meth)acrylate, and any combination thereof.

Clause 93. The composition of clause 91 or clause 92, wherein the at least one aromatic (meth)acrylate is 2-phenylethyl acrylate.

Clause 94. The composition of any one of clauses 91-93, wherein the reactive monomer mixture comprises the aromatic (meth)acrylate in an amount between about 10 and about 25 weight percent, between about 10 and about 20 weight percent, or between about 12 and about 15 weight percent.

Clause 95. The composition of any one of clauses 64-94, wherein the reactive monomer mixture further comprises a hydroxyalkyl (meth)acrylate.

Clause 96. The composition of clause 95, wherein the hydroxyalkyl (meth)acrylate comprises a linear, branched, or cyclic hydroxyalkyl group having between 1 and 25 carbon atoms.

Clause 97. The composition of clause 95 or clause 96, wherein the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

Clause 98. The composition of any one of clauses 95-97, wherein the hydroxyalkyl (meth)acrylate is 2-hydroxyethyl methacrylate.

Clause 99. The composition of any one of clauses 95-98, wherein the reactive monomer mixture comprises the hydroxyalkyl (meth)acrylate in an amount between about 1 and about 10 weight percent, between about 2 and about 8 weight percent, or between about 4 and about 6 weight percent.

Clause 100. The composition of any one of clauses 64-99, wherein the cross-linking agent is selected from the group consisting of a non-cycloaliphatic cross-linking agent, a cycloaliphatic cross-linking agent, and any combination thereof.

Clause 101. The composition any one of clauses 64-100, wherein the cross-linking agent is a cycloaliphatic cross-linking agent comprising a cycloaliphatic group having between one and four cycloaliphatic rings.

Clause 102. The composition of clause 101, wherein the cycloaliphatic cross-linking agent is tricyclo[$5.2.1.0^{2,6}$]decanedimethanol di(meth)acrylate.

Clause 103. The composition of any one of clauses 64-102, wherein the reactive monomer mixture comprises the cross-linking agent in an amount between about 1 and about 20 weight percent, between about 3 and about 15 weight percent, or between about 3 and about 10 weight percent.

Clause 104. The composition of any of clauses 64-103, wherein the reactive monomer mixture further comprises a polyamide.

Clause 105. The composition of clause 104, wherein the polyamide is selected from poly(vinyl pyrrolidone), poly(N-vinyl-N-methyl acetamide), poly(N-vinyl acetamide), poly (dimethyl acrylamide), and a copolymer or a mixture thereof.

Clause 106. The composition of clause 105, wherein the polyamide is poly(vinyl pyrrolidone).

Clause 107. The composition of clause 104, wherein the polyamide is a copolymer.

Clause 108. The composition of any one of clauses 104-107, wherein the reactive monomer mixture comprises the polyamide in an amount between about 0.1 weight percent and about 5 weight percent, between about 0.5 weight percent and about 3 weight percent, or between about 0.5 weight percent and about 2 weight percent.

Clause 109. The composition of any one of clauses 64-108, further comprising at least one UV/HEV absorbing compound in the reactive monomer mixture.

Clause 110. The composition of clause 109, wherein the UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido) ethyl methacrylate, 2-(2-cyano-2-(9H-xanthen-9-ylidene) acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, or any combination thereof.

Clause 111. The composition of clause 109 or clause 110, wherein the reactive monomer mixture comprises the UV/HEV absorbing compound in an amount between about 0.1 and about 5 weight percent, between about 1 and about 4 weight percent, or between about 1 and about 3 weight percent.

Clause 112. The composition of any one of clauses 64-111, further comprising at least one diluent in the reactive monomer mixture.

Clause 113. The composition of any one of clauses 64-112, having a water content of between about 0 weight percent and about 15 weight percent, between about 1 weight percent and about 10 weight percent, or between about 1 weight percent and about 8 weight percent.

Clause 114. The composition of any one of clauses 64-113, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 115. The composition of any one of clauses 64-114, wherein the free radical polymerization is a photo-polymerization using a bisacylphosphine oxide initiator.

Clause 116. An ophthalmic device comprising the composition of any one of clauses 64-115.

Clause 117. The ophthalmic device of clause 116 wherein the ophthalmic device comprises an intraocular lens, contact lens, corneal inlay, corneal outlay, or corneal insert.

Clause 118. The ophthalmic device of clause 117, wherein the ophthalmic device comprises an intraocular lens.

Clause 119. A method for making an ophthalmic device, the method comprising:

c. providing a composition of any one of clauses 64-115; and d. forming an ophthalmic device.

Clause 120. The method of clause 119, further comprising the step of extracting the ophthalmic device with a solvent.

Clause 121. The method of clause 120, further comprising the step of hydrating the extracted ophthalmic device with at least one aqueous solution.

Clause 122. A method for making an ophthalmic device, the method comprising:

c. preparing a blank from the composition any of clauses 64-115;

d. machining an ophthalmic device from the blank.

Clause 123. The method of clause 122, further comprising the step of extracting the ophthalmic device with a solvent.

Clause 124. The method of clause 123, further comprising the step of hydrating the extracted ophthalmic device with at least one aqueous solution.

Clause 125. The method of any one of clauses 119-124, further comprising an irradiation step using a femtosecond two photon laser.

Clause 126. The method of any of clauses 119-125, further comprising a step of sterilizing the ophthalmic device.

Clause 127. A method for making an ophthalmic device, the method comprising molding the device from the composition any of clauses 64-115.

Clause 128. A composition made by free radical polymerization of a reactive monomer mixture comprising:

a. at least one cycloaliphatic (meth)acrylate;
b. at least one aromatic (meth)acrylate;
c. at least one aliphatic (meth)acrylate; and
d. at least one cross-linking agent;

wherein the composition exhibits a refractive index of at least 1.45 and an Abbe number of at least 39.

Clause 129. The composition of clause 128, wherein the cycloaliphatic (meth)acrylate comprises a cycloaliphatic group having between one and four cycloaliphatic rings.

Clause 130. The composition of clause 128 or clause 129, wherein the cycloaliphatic (meth)acrylate has at least one cycloaliphatic group comprising at least one carbon-carbon double bond.

Clause 131. The composition of clause 128 or clause 129, wherein the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth)acrylate, isobornyl derivatives, norbornyl derivatives, ((1R, 2S,4R)-bicyclo[2.2.1]hept-5-en-2-yl)methyl (meth)acrylate, ethylene glycol dicyclopentenyl ether (meth)acrylate, poly(ethylene) glycol dicyclopentenyl ether (meth)acrylate, (1R, 3S, 5f, 7r)-2-methyladamantan-2-yl (meth)acrylate, (1R, 3S, 5f, 7r)-2-methyladamantan-2-yl PEG (meth)acrylate derivates and (1R, 3S, 5f, 7r)-2-methyladamantan-2-yl (meth)acrylate derivatives, and any combination thereof.

Clause 132. The composition of clause 128 or clause 129, wherein the cycloaliphatic (meth)acrylate is selected from cyclohexyl acrylate, cyclohexylmethyl acrylate, cyclohexylmethyl methacrylate, 2-cyclohexylethylacrylate, 2-cyclohexylethyl methacrylate, 3-cyclohexylpropylacrylate, ethylene glycol dicyclopentenyl ether acrylate, and any combination thereof.

Clause 133. The composition of any one of clauses 128-132, wherein the reactive monomer mixture comprises the cycloaliphatic (meth)acrylate in amount between about 20 and about 80 weight percent, between about 40 and about 80 weight percent, or between about 60 and about 80 weight percent.

Clause 134. The composition of any one of clauses 128-133, wherein the aromatic (meth)acrylate is selected from 2-phenylethyl (meth)acrylate, 2-phenoxyethyl (meth)acrylate, 3-phenylpropyl (meth)acrylate, 4-phenylbutyl (meth)acrylate, 3-phenoxypropyl (meth)acrylate, 1,3-bisphenylthiol-2-propyl (meth)acrylate, poly(ethylene glycol) phenyl ether (meth)acrylate, and any combination thereof.

Clause 135. The composition of clause 134, wherein the aromatic (meth)acrylate is selected from 2-phenylethyl acrylate, 2-phenylethyl methacrylate, 3-phenylpropyl acrylate, and combinations thereof.

Clause 136. The composition of any one of clauses 128-133, wherein the aromatic (meth)acrylate has at least one aliphatic group comprising at least one carbon-carbon double bond.

Clause 137. The composition of clause 136 wherein the aromatic (meth)acrylate is cinnamyl (meth)acrylate.

Clause 138. The composition of any one of clauses 128-137, wherein the reactive monomer mixture comprises the aromatic (meth)acrylate in an amount between about 5 and about 50 weight percent, between about 10 and about 40 weight percent, or between about 15 and about 40 weight percent.

Clause 139. The composition of any one of clauses 128-138, wherein the aliphatic (meth)acrylate comprises a linear or branched alkyl group containing between 1 and 25 carbon atoms.

Clause 140. The composition of any one of clauses 128-139, wherein the aliphatic (meth)acrylate has at least one aliphatic group comprising at least one carbon-carbon double bond.

Clause 141. The composition of any one of clauses 128-139, wherein the aliphatic (meth)acrylate comprises a linear alkyl group containing between 4 and 8 carbon atoms.

Clause 142. The composition of clause 141, wherein the aliphatic (meth)acrylate is n-hexyl acrylate.

Clause 143. The composition of any one of clauses 128-142, wherein the reactive monomer mixture comprises the aliphatic (meth)acrylate in an amount between 1 and 40 weight percent, between about 1 and about 20 weight percent, or between about 1 and about 10 weight percent.

Clause 141. The composition of any one of clauses 128-143, wherein the cross-linking agent is selected from the group consisting of a non-cycloaliphatic cross-linking agent, a cycloaliphatic cross-linking agent, and any combination thereof.

Clause 145. The composition of clause 144, wherein the cross-linking agent is a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, and any combination thereof.

Clause 146. The composition of clause 145, wherein the non-cycloaliphatic cross-linking agent is ethylene glycol dimethacrylate.

Clause 147. The composition of clause 146, wherein the cross-linking agent is a cycloaliphatic cross-linking agent comprising a cycloaliphatic group having between one and four cycloaliphatic rings.

Clause 148. The composition of clause 147, wherein the cycloaliphatic cross-linking agent is tricyclo[5.2.1.0$^{2,6}$]decanedimethanol di(meth)acrylate.

Clause 149. The composition of clause 148 or clause 148, wherein the reactive monomer mixture comprises the cycloaliphatic cross-linking agent in an amount between about 1 and about 20 weight percent, between about 3 and about 15 weight percent, or between about 3 and about 10 weight percent.

Clause 150. The composition of any of clauses 128-149, wherein the reactive monomer mixture further comprises a polyamide.

Clause 151. The composition of clause 150, wherein the polyamide is selected from poly(vinyl pyrrolidone), poly(N-vinyl-N-methyl acetamide), poly(N-vinyl acetamide), poly (dimethyl acrylamide), and a copolymer or a mixture thereof.

Clause 152. The composition of clause 151, wherein the polyamide is poly(vinyl pyrrolidone).

Clause 153. The composition of clause 150, wherein the polyamide is a copolymer.

Clause 154. The composition of any one of clauses 150-153, wherein the reactive monomer mixture comprises the polyamide in an amount between about 0.1 weight percent and about 5 weight percent, between about 0.5 weight percent and about 3 weight percent, or between about 0.5 weight percent and about 2 weight percent.

Clause 155. The composition of any one of clauses 128-154, further comprising at least one hydroxy silicone monomer.

Clause 156. The composition of clause 155, wherein the hydroxy silicone monomer comprises mono-n-butyl terminated mono-(2-hydroxy-3-methacryloxypropyloxy)-propyl terminated polydimethylsiloxane, 3-(3-(1,1,1,3,5,5,5-heptamethyltrisiloxan-3-yl)propoxy)-2-hydroxypropyl methacrylate, 3-(3-(1,5-di-tert-butyl-1,1,3,5,5-pentamethyltrisiloxan-3-yl)propoxy)-2-hydroxypropyl methacrylate, or any combination thereof.

Clause 157. The composition of clause 155 or clause 156, wherein the reactive monomer mixture comprises the hydroxy silicone monomer in an amount between about 1 and about 25 weight percent, between about 5 and about 20 weight percent, or between about 10 and about 20 weight percent.

Clause 158. The composition of any one of clauses 128-157, further comprising at least one hydroxyalkyl (meth)acrylate.

Clause 159. The composition of clause 158, wherein the hydroxyalkyl (meth)acrylate comprises a linear, branched, or cyclic hydroxyalkyl group having between 1 and 25 carbon atoms.

Clause 160. The composition of clause 159, wherein the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth) acrylate, 1,1-dimethyl-2-hydroxyethyl (meth)acrylate, 4-hydroxybutyl (meth)acrylate, and any combination thereof.

Clause 161. The composition of clause 160, wherein the hydroxyalkyl (meth)acrylate is 4-hydroxybutyl acrylate or 2-hydroxyethyl methacrylate.

Clause 162. The composition of any one of clauses 158-161, wherein the reactive monomer mixture comprises the hydroxyalkyl (meth)acrylate in an amount between about 1 and about 25 weight percent, between about 5 and about 20 weight percent, or between about 10 and about 20 weight percent.

Clause 163. The composition of any one of clauses 128-162, further comprising at least one UV/HEV absorbing compound in the reactive monomer mixture.

Clause 164. The composition of clause 163, wherein the UV/HEV absorbing compound is a compound of Formula I, 2-(2'-hydroxy-5-methacrylyloxyethylphenyl)-2H-benzotriazole, 2-(2-cyano-2-(9H-thioxanthen-9-ylidene)acetamido) ethyl methacrylate, 2-(2-cyano-2-(9H-xanthen-9-ylidene) acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate or any combination thereof.

Clause 165. The composition of clause 163 or clause 164, wherein the reactive monomer mixture comprises the UV/HEV absorbing compound in an amount between about 0.1 and about 5 weight percent, between about 1 and about 4 weight percent, or between about 1 and about 3 weight percent.

Clause 166. The composition of any one of clauses 128-165, further comprising at least one hydrophilic monomer.

Clause 167. The composition of clause 166, wherein the hydrophilic monomer is selected from vinyl pyrrolidone, N-vinyl-N-methyl acetamide, N-methyl methacrylamide, N-vinyl acetamide, N, N-dimethyl acrylamide, poly(ethylene glycol) methyl ether (meth)acrylate, poly(ethylene glycol) (meth)acrylate, and any combination thereof.

Clause 168. The composition of clause 166, wherein the hydrophilic monomer has at least one aliphatic group having at least one double bond.

Clause 169. The composition of any one of clauses 128-168, further comprising at least one diluent in the reactive monomer mixture.

Clause 170. The composition of any one of clauses 128-169, having a water content of between about 0 weight percent and about 15 weight percent, between about 1 weight percent and about 10 weight percent, or between about 1 weight percent and about 8 weight percent.

Clause 171. The composition of any one of clauses 128-170, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 172. The composition of any one of clauses 128-171, wherein the free radical polymerization is a photopolymerization using a bisacylphosphine oxide initiator.

Clause 173. An ophthalmic device comprising the composition of any one of clauses 128-172.

Clause 174. The ophthalmic device of clause 173 wherein the ophthalmic device comprises an intraocular lens, contact lens, corneal inlay, corneal outlay, or corneal insert.

Clause 175. The ophthalmic device of clause 174, wherein the ophthalmic device comprises an intraocular lens.

Clause 176. A method for making an ophthalmic device, the method comprising:
 a. providing a composition of any one of clauses 128-172; and
 b. forming an ophthalmic device.

Clause 177. The method of clause 176, further comprising the step of extracting the ophthalmic device with a solvent.

Clause 178. The method of clause 177, further comprising the step of hydrating the extracted ophthalmic device with at least one aqueous solution.

Clause 179. A method for making an ophthalmic device, wherein the forming is performed by either:
  a. preparing a blank from the composition any of clauses 128-172 and machining an ophthalmic device from the blank; or
  b. molding a lens from the composition any of clauses 128-172; or
  c. molding a lens from the composition any of clauses 128-172 and refining the surface by machining.

Clause 180. The method of clause 179, further comprising the step of extracting the ophthalmic device with a solvent.

Clause 181. The method of clause 290, further comprising the step of hydrating the extracted ophthalmic device with at least one aqueous solution.

Clause 182. The method of any one of clauses 176-181, further comprising an irradiation step using a femtosecond two photon laser.

Clause 183. The method of any of clauses 176-182, further comprising a step of sterilizing the ophthalmic device.

Clause 184. A method for making an ophthalmic device, the method comprising molding the device from the composition any of clauses 128-172.

Clause 185. A composition made by free radical polymerization of a reactive monomer mixture comprising:
  a. at least one cycloaliphatic (meth)acrylate;
  b. at least one aliphatic (meth)acrylate; and
  c. at least one cross-linking agent;
  wherein the composition exhibits a refractive index of at least 1.45 and an Abbe number of at least 39.

Clause 186. The composition of clause 185, wherein the cycloaliphatic (meth)acrylate comprises a cycloaliphatic group having between one and four cycloaliphatic rings.

Clause 187. The composition of clause 185 or clause 186, wherein the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth) acrylate, isobornyl derivatives, norbornyl derivatives, ((1R, 2S,4R)-bicyclo[2.2.1]hept-5-en-2-yl)methyl (meth)acrylate, ethylene glycol dicyclopentenyl ether (meth)acrylate, poly (ethylene) glycol dicyclopentenyl ether (meth)acrylate, 2-(((3 aR,4R,5 S, 7R, 7aR)-octahydro-1H-4,7-m ethanoinden-5-yl)oxy)ethyl acrylate, 2-(((3 aS,4R,6 S,7R,7aR)-3a,4,5,6,7,7a-hexahydro-1H-4,7-methanoinden-6-yl)oxy)ethyl acrylate, (3 aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R, 3 S, 5f, 7r)-2-methyladamantan-2-yl (meth)acrylate, (1R, 3 S, 5f, 7r)-2-methyladamantan-2-yl PEG (meth)acrylate derivates and (1R, 3 S, 5f, 7r)-2-methyladamantan-2-yl (meth)acrylate derivatives, and any combination thereof.

Clause 188. The composition of any one of clauses 185-187, wherein the cycloaliphatic (meth)acrylate is selected from cyclohexyl acrylate, cyclohexylmethyl acrylate, cyclohexylmethyl methacrylate, 2-cyclohexylethyl acrylate, 2-cyclohexylethyl methacrylate, 3-cyclohexylpropylacrylate, ethylene glycol dicyclopentenyl ether acrylate, and any combination thereof.

Clause 189. The composition of any one of clauses 185-188, wherein the reactive monomer mixture comprises the cycloaliphatic (meth)acrylate in an amount between about 20 and about 80 weight percent, between about 40 and about 80 weight percent, or between about 60 and about 80 weight percent.

Clause 190. The composition of any one of clauses 185-189, wherein the aliphatic (meth)acrylate comprises a linear or branched alkyl group containing between 1 and 25 carbon atoms.

Clause 191. The composition of clause 190, wherein the aliphatic (meth)acrylate comprises a linear or branched alkyl group containing between 4 and 8 carbon atoms.

Clause 192. The composition of clause 191, wherein the aliphatic (meth)acrylate is isobutyl acrylate or n-hexyl acrylate.

Clause 193. The composition of any one of clauses 185-192, wherein the reactive monomer mixture comprises the aliphatic (meth)acrylate in an amount between about 1 and about 40 weight percent, between about 1 and about 20 weight percent, or between about 1 and about 10 weight percent.

Clause 194. The composition of any one of clauses 185-193, wherein the cross-linking agent is selected from a non-cycloaliphatic cross-linking agent, a cycloaliphatic cross-linking agent, and any combination thereof.

Clause 195. The composition of clause 194, wherein the cross-linking agent is a non-cycloaliphatic cross-linking agent selected from ethylene glycol di(meth)acrylate, diethylene glycol di(meth)acrylate, triethylene glycol di(meth) acrylate, tetraethylene glycol di(meth)acrylate, trimethylolpropane tri(meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, and any combination thereof.

Clause 196. The composition of clause 195, wherein the non-cycloaliphatic cross-linking agent is ethylene glycol dimethacrylate.

Clause 197. The composition of clause 194, wherein the cross-linking agent is a cycloaliphatic cross-linking agent comprising a cycloaliphatic group having between one and four cycloaliphatic rings.

Clause 198. The composition of clause 197, wherein the cycloaliphatic cross-linking agent is tricyclo[$5.2.1.0^{2,6}$]decanedimethanol di(meth)acrylate.

Clause 199. The composition of any one of clauses 185-198, wherein the reactive monomer mixture comprises the cross-linking agent in an amount between about 1 and about 20 weight percent, between about 1 and about 15 weight percent, or between about 1 and about 5 weight percent.

Clause 200. The composition of any one of clauses 185-199, further comprising an aromatic (meth)acrylate.

Clause 201. The composition of clause 200, wherein the aromatic (meth)acrylate is selected from 2-phenylethyl (meth)acrylate, 2-phenoxyethyl (meth)acrylate, 3-phenylpropyl (meth)acrylate, 3-phenoxypropyl (meth)acrylate, 1,3-bis-phenylthiol-2-propyl (meth)acrylate, poly(ethylene glycol) phenyl ether (meth)acrylate, and any combination thereof.

Clause 202. The composition of clause 201, wherein the aromatic (meth)acrylate is selected from 2-phenylethyl acrylate, 2-phenylethyl methacrylate, 3-phenylpropyl acrylate, and combinations thereof.

Clause 203. The composition of any one of clauses 200-202, wherein the reactive monomer mixture comprises the aromatic (meth)acrylate in an amount between about 5 and about 50 weight percent, between about 10 and about 40 weight percent, or between about 15 and about 40 weight percent.

Clause 204. The composition of any one of clauses 185-203, further comprising at least one hydroxyalkyl (meth)acrylate.

Clause 205. The composition of clause 204, wherein the hydroxyalkyl (meth)acrylate comprises a linear, branched, or cyclic hydroxyalkyl group having between 1 and 25 carbon atoms.

Clause 206. The composition of clause 205, wherein the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

Clause 207. The composition of clause 206, wherein the hydroxyalkyl (meth)acrylate is 4-hydroxybutyl acrylate or 2-hydroxyethyl methacrylate.

Clause 208. The composition of any one of clauses 204-207, wherein the reactive monomer mixture comprises the hydroxyalkyl (meth)acrylate in an amount between about 1 and about 25 weight percent, between about 5 and about 20 weight percent, or between about 10 and about 20 weight percent.

Clause 209. The composition of any one of clauses 185-209, wherein the reactive monomer mixture further comprises at least one hydrophilic monomer.

Clause 210. The composition of clause 209, wherein the at least one hydrophilic monomer is selected from vinyl pyrrolidone, N-vinyl N-methyl acetamide, N-methyl methacrylamide, N-vinyl acetamide, N,N-dimethyl acrylamide, N-hydroxyethylacrylamide, N-(2-hydroxypropyl)acryl amide, N-(3-hydroxypropyl)acrylamide, N-(2-hydroxyethyl)(meth)acrylamide, N-(2-hydroxypropyl)(meth)acrylamide, N-(3 hydroxypropyl)(meth)acrylamide, poly(ethylene glycol) methyl ether (meth)acrylate, poly(ethylene glycol) (meth)acrylate, and any combination thereof.

Clause 211. The composition of any one of clauses 185-209, wherein the reactive monomer mixture further comprises a polyamide.

Clause 212. The composition of clause 211, wherein the polyamide is selected from poly(vinyl pyrrolidone), poly(N-vinyl N-methyl acetamide), poly(N-vinyl acetamide), poly(dimethyl acrylamide), and a copolymer or a mixture thereof.

Clause 213. The composition of clause 212, wherein the polyamide is poly(vinyl pyrrolidone).

Clause 214. The composition of clause 213, wherein the polyamide is a copolymer.

Clause 215. The composition of any one of clauses 185-214, wherein the reactive monomer mixture comprises the polyamide in an amount between about 0.1 weight percent and about 5 weight percent, between about 0.5 weight percent and about 3 weight percent, or between about 0.5 weight percent and about 2 weight percent.

Clause 216. The composition of any one of clauses 185-215, further comprising at least one UV/HEV absorbing compound in the reactive monomer mixture.

Clause 217. The composition of clause 216, wherein the UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, or any combination thereof.

Clause 218. The composition of clause 216 or clause 217, wherein the reactive monomer mixture comprises the UV/HEV absorbing compound in an amount between about 0.1 and about 5 weight percent, between about 1 and about 4 weight percent, or between about 1 and about 3 weight percent.

Clause 219. The composition of any one of clauses 185-218, further comprising at least one diluent in the reactive monomer mixture.

Clause 220. The composition of any one of clauses 185-219, having a water content of between about 0 weight percent and about 15 weight percent, between about 1 weight percent and about 10 weight percent, or between about 1 weight percent and about 8 weight percent.

Clause 221. The composition of any one of clauses 185-220, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 222. The composition of any one of clauses 185-221, wherein the free radical polymerization is a photopolymerization using a bisacylphosphine oxide initiator.

Clause 223. An ophthalmic device comprising the composition of any one of clauses 185-222.

Clause 224. The ophthalmic device of clause 223, wherein the ophthalmic device comprises an intraocular lens, contact lens, corneal inlay, corneal outlay, or corneal insert.

Clause 225. The ophthalmic device of clause 224, wherein the ophthalmic device comprises an intraocular lens.

Clause 226. A method for making an ophthalmic device, the method comprising:
 a. providing a composition of any one of clauses 185-225; and
 b. forming an ophthalmic device.

Clause 227. The method of clause 226, further comprising the step of extracting the ophthalmic device with a solvent.

Clause 228. The method of clause 227, further comprising the step of hydrating the extracted ophthalmic device with at least one aqueous solution.

Clause 229. A method for making an ophthalmic device, the method comprising either:
 a. preparing a blank from the composition any of clauses 185-225 and
 b. machining an ophthalmic device from the blank.

Clause 230. The method of clause 229, further comprising the step of extracting the ophthalmic device with a solvent.

Clause 231. The method of clause 230, further comprising the step of hydrating the extracted ophthalmic device with at least one aqueous solution.

Clause 232. The method of any one of clauses 226-231, further comprising an irradiation step using a femtosecond two photon laser.

Clause 233. The method of any of clauses 226-232, further comprising a step of sterilizing the ophthalmic device.

Clause 234. A method for making an ophthalmic device, the method comprising molding the device from the composition of any one of clauses 185-225.

Clause 235. A composition made by free radical polymerization of a reactive monomer mixture comprising:
 a. at least one hydrophobic monomer;
 b. at least one acrylate monomer of the following formula (I):

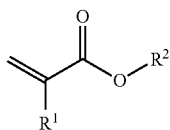

(I)

wherein R¹ is selected from hydrogen and methyl, and wherein R² is a non-aromatic moiety having at least one carbon-carbon double bond; and c. at least one cross-linking agent.

Clause 236. The composition of clause 235, wherein the hydrophobic monomer is a hydrophobic (meth)acrylate monomer.

Clause 237. The composition of clause 236, wherein the hydrophobic (meth)acrylate is selected from an aliphatic (meth)acrylate, an aromatic (meth)acrylate, a cycloaliphatic (meth)acrylate, and any combination thereof.

Clause 238. The composition of clause 237, wherein the hydrophobic (meth)acrylate is an aliphatic (meth)acrylate.

Clause 239. The composition of clause 238, wherein the aliphatic (meth)acrylate is a $C_1$-$C_{18}$ alkyl (meth)acrylate.

Clause 240. The composition of clause 239, wherein the $C_1$-$C_{18}$ alkyl (meth)acrylate is selected from the group consisting of ethyl (meth)acrylate, n-butyl (meth)acrylate, iso-butyl (meth)acrylate, t-butyl (meth)acrylate, n-hexyl (meth)acrylate, 2-ethylhexyl (meth)acrylate, octyl (meth)acrylate, iso-decyl (meth)acrylate, heptadecyl (meth)acrylate, dodecyl (meth)acrylate, 2-propylheptyl (meth)acrylate, stearyl (meth)acrylate, and any combination thereof.

Clause 241. The composition of clause 240, wherein the $C_1$-$C_{18}$ alkyl (meth)acrylate is n-hexyl acrylate.

Clause 242. The composition of clause 237, wherein the hydrophobic (meth)acrylate is an aromatic (meth)acrylate.

Clause 243. The composition of clause 242, wherein the aromatic (meth)acrylate is selected from the group consisting of 2-phenylethyl (meth)acrylate, 2-phenoxyethyl (meth)acrylate, 4-chlorophenoxyethyl (meth)acrylate, 3-phenylpropyl (meth)acrylate, 4-phenylbutyl (meth)acrylate, 3-phenoxypropyl (meth)acrylate, 1,3-bis-phenylthiol-2-propyl (meth)acrylate, poly(ethylene glycol) phenyl ether (meth)acrylate, and any combination thereof.

Clause 244. The composition of clause 243, wherein the aromatic (meth)acrylate is 2-phenylethyl acrylate.

Clause 245. The composition of clause 243, wherein the aromatic (meth)acrylate is 2-phenylethyl methacrylate.

Clause 246. The composition of clause 243, wherein the aromatic (meth)acrylate is a combination of 2-phenylethyl acrylate and 2-phenylethyl methacrylate.

Clause 247: The composition of clause 243, wherein the aromatic (meth)acrylate is a combination of 2-phenylethyl methacrylate and 3-phenylpropyl acrylate.

Clause 248. The composition of clause 237, wherein the hydrophobic (meth)acrylate is a cycloaliphatic (meth)acrylate.

Clause 249. The composition of clause 248, wherein the cycloaliphatic (meth)acrylate is selected from cyclohexyl (meth)acrylate, cyclohexyl PEG (meth)acrylate derivatives, cyclohexyl (meth)acrylate derivatives, cyclopentyl (meth)acrylate, cyclohexylmethyl (meth)acrylate, 2-cyclohexylethyl (meth)acrylate, 3-cyclohexylpropyl (meth)acrylate, norbornyl (meth)acrylate, isobornyl (meth)acrylate, isobornyl derivatives, norbornyl derivatives, ((1R,2S,4R)-bicyclo[2.2.1]hept-5-en-2-yl)methyl (meth)acrylate, ethylene glycol dicyclopentenyl ether (meth)acrylate, poly(ethylene) glycol dicyclopentenyl ether (meth)acrylate, 2-(((3aR,4R,5S,7R,7aR)-octahydro-1H-4,7-methanoinden-5-yl)oxy)ethyl acrylate, 2-(((3aS,4R,6S,7R,7aR)-3a,4,5,6,7,7ahexahydro-1H-4,7-methanoinden-6-yl)oxy)ethyl acrylate, (3 aS,4S,5R,7S,7aS)-octahydro-1H-4,7-methanoinden-5-yl acrylate, (3aS,4S,5R,7S,7aS)-3a,4,5,6,7,7a-hexahydro-1H-4,7-methanoinden-5-yl acrylate, (1R, 3S, 5f, 7r)-2-methyladamantan-2-yl (meth)acrylate, (1R, 3S, 5f, 7r)-2-methyladamantan-2-yl PEG (meth)acrylate derivates and (1R, 3S, 5f, 7r)-2-methyladamantan-2-yl (meth)acrylate derivatives, and any combination thereof.

Clause 250. The composition of clause 249, wherein the cycloaliphatic (meth)acrylate is selected from cyclohexyl acrylate, cyclohexylmethyl acrylate, cyclohexylmethyl methacrylate, 2 cyclohexylethyl acrylate, 2-cyclohexylethyl methacrylate, and any combination thereof.

Clause 251. The composition of any one of clauses 235-250, wherein R² comprises an alkenyl or cycloalkenyl moiety.

Clause 252. The composition of clause 251, wherein R² comprises a cyclopentenyl, cyclopentadienyl, cyclohexenyl, cyclohexadienyl, bicyclo[2.2.1]hept-5-en-2-yl, hexahydro-1H-4,7-methanoindenyl, or allyl moiety.

Clause 253. The composition of any one of clauses 235-250, wherein the acrylate monomer of formula (I) is selected from ((1R,2S,4R)-bicyclo[2.2.1]hept-5-en-2-yl) methyl acrylate, 2-(((3aS,4R,6S,7R,7aR)-3a,4,5,6,7,7a-hexahydro-1H-4,7-methanoinden-6-yl)oxy)ethyl acrylate, (3aS,4S,5R,7S,7aS)-3a,4,5,6,7,7a-hexahydro-1H-4,7-methanoinden-5-yl acrylate, 2 (cyclopenta-2,4-dien-1-yloxy)ethyl acrylate, cyclopenta-2,4-dien-1-yl acrylate, cyclopent-3-en-1-yl acrylate, 2-(cyclopent-3-en-1-yloxy) ethyl acrylate, cyclohexa-2,4-dien-1-yl acrylate, 2-(cyclohexa-2,4-dien-1-yloxy)ethyl acrylate, 2-(cyclohex-3-en-1-yloxy)ethyl acrylate, cyclohex-3-en-1-yl acrylate, 2-(2-(2-(2-(cyclohex-3-en-1-yloxy)ethoxy)ethoxy)ethoxy)ethyl acrylate, N,N-diallyl acrylamide, allyl acrylate, and 2-(allyloxy)ethyl acrylate.

Clause 254. The composition of any one of clauses 235-253, wherein the composition further comprises a hydroxyl-containing monomer.

Clause 255. The composition of clause 254, wherein the hydroxyl-containing monomer is a hydroxyalkyl (meth) acrylate.

Clause 256. The composition of clause 255, wherein the hydroxyalkyl (meth)acrylate is selected from 2-hydroxyethyl (meth)acrylate, 2-hydroxypropyl (meth)acrylate, 3-hydroxypropyl (meth)acrylate, 2,3-dihydroxypropyl (meth) acrylate, 1,1-dimethyl-2-hydroxyethyl (meth)acrylate, 4-hydroxybutyl (meth)acrylate, and any combination thereof.

Clause 257. The composition of clause 256, wherein the hydroxyalkyl (meth)acrylate is 4-hydroxybutyl acrylate or 2-hydroxyethyl methacrylate.

Clause 258. The composition of clause 254, wherein the hydroxyl-containing monomer is a hydroxysilicone monomer.

Clause 259. The composition of clause 258, wherein the hydroxysilicone monomer is selected from 3-(3-(1,1,1,3,5,5,5-heptamethyltrisiloxan-3-yl)propoxy)-2-hydroxypropyl methacrylate (SiMAA), mono-n-butyl terminated monomethacryloxypropyl terminated polydimethylsiloxane (mPDMS), and mono-(2-hydroxy-3-methacryloxypropyl)-propyl ether terminated mono-n-butyl terminated polydimethylsiloxane (OH-mPDMS).

Clause 260. The composition of any one of clauses 235-259, wherein the reactive monomer mixture further comprises at least one hydrophilic monomer.

Clause 261. The composition of clause 260, wherein the at least one hydrophilic monomer is selected from vinyl pyrrolidone, N-vinyl N-methyl acetamide, N-methyl methacrylamide, N-vinyl acetamide, N,N-dimethyl acrylamide, N-hydroxyethylacrylamide, N-(2-hydroxypropyl)acrylamide, N-(3-hydroxypropyl)acrylamide, N-(2-hydroxyethyl)(meth)acrylamide, N-(2-hydroxypropyl)(meth)acrylamide, N-(3-hydroxypropyl)(meth)acrylamide, poly(ethylene glycol) methyl ether (meth)acrylate, poly(ethylene glycol) (meth)acrylate, and any combination thereof.

Clause 262. The composition of any one of clauses 235-261, wherein the cross-linking agent is selected from the group consisting of a non-cycloaliphatic cross-linking agent, a cycloaliphatic cross-linking agent, and any combination thereof.

Clause 263. The composition of clause 262, wherein the cross-linking agent is a non-cycloaliphatic cross-linking agent selected from ethylene glycol di(meth)acrylate, diethylene glycol di(meth)acrylate, triethylene glycol di(meth)acrylate, tetraethylene glycol di(meth)acrylate, trimethylolpropane tri(meth)acrylate, glycerol tri(meth)acrylate, triallyl cyanurate, methylene bis(meth)acrylamide, poly(ethylene glycol) di(meth)acrylate, bis(2-hydropropyl (meth)acrylate) terminated polydimethylsiloxanes, and any combination thereof.

Clause 264. The composition of clause 263, wherein the non-cycloaliphatic cross-linking agent is ethylene glycol dimethacrylate.

Clause 265. The composition of clause 262, wherein the cross-linking agent is a cycloaliphatic cross-linking agent comprising a cycloaliphatic group having between one and four cycloaliphatic rings.

Clause 266. The composition of clause 265 wherein the cycloaliphatic cross-linking agent is tricyclo[5.2.1.0$^{2,6}$]decanedimethanol di(meth)acrylate.

Clause 267. The composition of any one of clauses 235-266, wherein the reactive monomer mixture comprises the cross-linking agent in an amount between about 1 and about 20 weight percent, between about 3 and about 15 weight percent, or between about 3 and about 10 weight percent.

Clause 268. The composition of any one of clauses 235-261, wherein the cross-linking agent has formula:

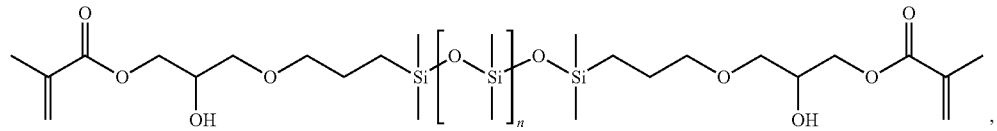

wherein n is an integer from 5 to 50.

Clause 269. The composition of clause 268, wherein n is 15, 16, 17, 18, 19, 20, 21, 22, 23, 24, or 25.

Clause 270. The composition of clause 269, wherein n is 20.

Clause 271. The composition of any one of clauses 134-136, wherein the reactive monomer mixture comprises the cross-linking agent in an amount of about 15% to about 22% by weight, or between about 16% to about 20% by weight.

Clause 272. The composition of any clause 271, wherein the cross-linking agent is present in the reactive monomer mixture in an amount of about 18% by weight.

Clause 273. The composition of any one of clauses 235-272, wherein the reactive monomer mixture further comprises a polyamide.

Clause 274. The composition of clause 273, wherein the polyamide is selected from poly(vinyl pyrrolidone), poly(N-vinyl N-methyl acetamide), poly(N-vinyl acetamide), poly (dimethyl acrylamide), and a copolymer or a mixture thereof.

Clause 275. The composition of clause 274, wherein the polyamide is poly(vinyl pyrrolidone) or poly(N-vinyl N-methyl acetamide).

Clause 276. The composition of clause 273, wherein the polyamide is a copolymer.

Clause 277. The composition of any one of clauses 273-276, wherein the reactive monomer mixture comprises the polyamide in an amount between about 0.1 weight percent and about 5 weight percent, or between about 0.25 weight percent and about 2 weight percent.

Clause 278. The composition of any one of clauses 235-277, further comprising at least one UV/HEV absorbing compound in the reactive monomer mixture.

Clause 279. The composition of clause 278, wherein the UV/HEV absorbing compound is a compound of Formula II, 2-(2'-hydroxy-5-methacrylyloxyethylphenyl)-2H-benzotriazole, 2-(2-cyano-2-(9H-thioxanthen-9-ylidene)acetamido) ethyl methacrylate, 2-(2-cyano-2-(9H-xanthen-9-ylidene) acetamido)ethyl methacrylate, 2-(2-cyano-2-(10-methylacridin-9(10H)-ylidene)acetamido)ethyl methacrylate 3-(3-(tert-butyl)-5-(5-chloro-2H-benzo[d][1,2,3]triazol-2-yl)-4-hydroxyphenyl)propyl methacrylate, or any combination thereof.

Clause 280. The composition of clause 278 or clause 279, wherein the reactive monomer mixture comprises the UV/HEV absorbing compound in an amount between about 0.1 and about 5 weight percent, between about 1 and about 4 weight percent, or between about 1 and about 3 weight percent.

Clause 281. The composition of any one of clauses 235-280, further comprising at least one diluent in the reactive monomer mixture.

Clause 282. The composition of any one of clauses 235-281, having a water content of between about 0 weight percent and about 15 weight percent, about 1 weight percent and about 10 weight percent, or about 1 weight percent and about 8 weight percent.

Clause 283. The composition of any one of clauses 235-282, wherein the composition has a refractive index of at least 1.45 and an Abbe number of at least 45; wherein the composition has a refractive index of at least 1.48 and an Abbe number of at least 50; or wherein the composition has a refractive index of at least 1.50 and an Abbe number of at least 50.

Clause 284. The composition of any one of clauses 235-283, wherein the free radical polymerization is a photopolymerization using a bisacylphosphine oxide initiator.

Clause 285. An ophthalmic device comprising the composition of any one of clauses 235-284.

Clause 286. The ophthalmic device of clause 285 wherein the ophthalmic device comprises an intraocular lens, contact lens, corneal inlay, corneal outlay, or corneal insert.

Clause 287. The ophthalmic device of clause 286, wherein the ophthalmic device comprises an intraocular lens.

Clause 288. A method for making an ophthalmic device, the method comprising:
a. providing a composition of any one of clauses 235-284; and
b. forming an ophthalmic device.

Clause 289. The method of clause 288, further comprising the step of extracting the ophthalmic device with a solvent.

Clause 290. The method of clause 289, further comprising the step of hydrating the extracted ophthalmic device with at least one aqueous solution.

Clause 291. A method for making an ophthalmic device, the method comprising either:
a. preparing a blank from the composition any of clauses 235-284; and
b. machining an ophthalmic device from the blank.

Clause 292. The method of clause 291, further comprising the step of extracting the ophthalmic device with a solvent.

Clause 293. The method of clause 292, further comprising the step of hydrating the extracted ophthalmic device with at least one aqueous solution.

Clause 294. The method of any one of clauses 288-293, further comprising an irradiation step using a femtosecond two photon laser.

Clause 295. The method of any of clauses 288-294, further comprising a step of sterilizing the ophthalmic device.

Clause 296. A method for making an ophthalmic device, the method comprising molding the device from the composition any of clauses 235-284.

We claim:

1. A composition made by free radical polymerization of a reactive monomer mixture comprising:
   (a) at least one hydrophobic monomer;
   (b) at least one hydrophilic monomer that is a poly(ethylene glycol) methyl ether methacrylate; and
   (c) a tricyclo[5.2.1.0$^{2,6}$]decanedimethanol di(meth)acrylate cross-linking agent;
wherein the composition exhibits a refractive index of at least 1.45 and an Abbe number of at least 39.

2. The composition of claim 1, wherein the hydrophobic monomer is a hydrophobic (meth)acrylate monomer selected from an aliphatic (meth)acrylate, an aromatic (meth)acrylate, a cycloaliphatic (meth)acrylate, and any combination thereof.

3. The composition of claim 2, wherein the hydrophobic (meth)acrylate is a cycloaliphatic (meth)acrylate selected from cyclohexyl acrylate, cyclohexylmethyl acrylate, cyclohexylmethyl methacrylate, 2-cyclohexylethyl acrylate, 2-cyclohexylethyl methacrylate, ethylene glycol dicyclopentenyl ether acrylate, and any combination thereof.

4. The composition of claim 2, wherein the hydrophobic (meth)acrylate is an aliphatic (meth)acrylate selected from $C_1$-$C_{18}$ alkyl (meth)acrylates.

5. The composition of claim 2, wherein the hydrophobic (meth)acrylate is an aromatic (meth)acrylate selected from the group consisting of 2-phenylethyl (meth)acrylate, 2-phenoxyethyl (meth)acrylate, 4-chlorophenoxyethyl (meth)acrylate, 3-phenylpropyl (meth)acrylate, 4-phenylbutyl (meth)acrylate, 3-phenoxypropyl (meth)acrylate, 1,3-bisphenylthiol-2-propyl (meth)acrylate, poly(ethylene glycol) phenyl ether (meth)acrylate, and any combination thereof.

6. The composition of claim 1, wherein the reactive monomer mixture comprises at least one hydroxyalkyl (meth)acrylate monomer selected from 2-hydroxyethyl (meth)acrylate, 2-hydroxypropyl (meth)acrylate, 3-hydroxypropyl (meth)acrylate, 2,3-dihydroxypropyl (meth)acrylate, 1,1-dimethyl-2-hydroxyethyl (meth)acrylate, 4-hydroxybutyl (meth)acrylate, and any combination thereof.

7. The composition of claim 1, wherein the reactive monomer mixture comprises a mixture of the hydrophilic monomer and a hydroxyalkyl (meth)acrylate monomer, wherein the hydroxyalkyl (meth)acrylate monomer is 2-hydroxyethyl acrylate.

8. The composition of claim 1, wherein the tricyclo[5.2.1.0$^{2,6}$]decanedimethanol di(meth)acrylate cross-linking agent is tricyclo[5.2.1.0$^{2,6}$]decanedimethanol diacrylate.

9. The composition of claim 1, further comprising at least one UV/HEV absorbing compound in the reactive monomer mixture wherein the UV/HEV absorbing compound is selected from 2-(2'-hydroxy-5-methacrylyloxyethylphenyl)-2H-benzotriazole, 2-(2-cyano-2-(9H-thioxanthen-9-ylidene)acetamido)ethyl methacrylate, 2-(2-cyano-2-(9H-xanthen-9-ylidene)acetamido)ethyl methacrylate, 2-(2-cyano-2-(10-methylacridin-9(10H)-ylidene)acetamido)ethyl methacrylate, 3-(3-(tert-butyl)-5-(5-chloro-2H-benzo[d][1,2,3]triazol-2-yl)-4-hydroxyphenyl)propyl methacrylate, a compound of formula II:

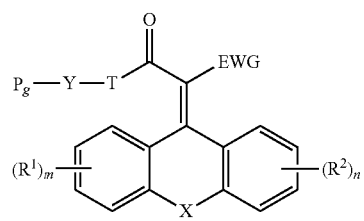

Formula II wherein:
m and n are independently 0, 1, 2, 3, or 4;
T is a bond, O, or NR;
X is O, S, NR, SO, or SO$_2$;
Y is a linking group;
P$_g$ is a polymerizable group;
R at each occurrence is independently H, $C_1$-$C_6$ alkyl, cycloalkyl, heterocycloalkyl, aryl, heteroaryl, or Y—P$_g$;
R$^1$ and R$^2$, when present, are independently at each occurrence $C_1$-$C_6$ alkyl, $C_1$-$C_6$ alkoxy, $C_1$-$C_6$ thioalkyl, $C_3$-$C_7$ cycloalkyl, aryl, halo, hydroxy, amino, NR$^3$R$^4$, or benzyl, wherein R$^3$ and R$^4$ are independently H or $C_1$-$C_6$ alkyl, or two adjacent R$^1$ or R$^2$ groups, together with the carbon atoms to which they are attached, combine to form a cycloalkyl or aryl ring; and
EWG is an electron withdrawing group;
and any combination thereof.

10. The composition of claim 1, further comprising at least one diluent in the reactive monomer mixture.

11. The composition of claim 1, having a water content of between about 0 weight percent and about 15 weight percent.

12. The composition of claim 1, wherein the composition has a refractive index of at least 1.45 and an Abbe number of at least 45.

13. The composition of claim 1, wherein the free radical polymerization is a photopolymerization using a bisacylphosphine oxide initiator.

14. An ophthalmic device comprising the composition of claim 1.

15. The ophthalmic device of claim 14 wherein the ophthalmic device comprises an intraocular lens, contact lens, corneal inlay, corneal outlay, or corneal insert.

16. A method for making an ophthalmic device, the method comprising:
(a) providing a composition made by free radical polymerization of a reactive monomer mixture of claim 1; and
(b) forming an ophthalmic device.

17. The composition of claim 3, wherein the cycloaliphatic (meth)acrylate is ethylene glycol dicyclopentenyl ether acrylate.

18. The composition of claim 6, wherein the hydroxyalkyl (meth)acrylate monomer is 4-hydroxybutyl acrylate.

19. The composition of claim 4, wherein the aliphatic (meth)acrylate comprises a $C_4$-$C_8$ linear alkyl group.

20. The composition of claim 2, wherein the reactive monomer mixture comprises the at least one cycloaliphatic (meth)acrylate in an amount between 50 and 80 weight percent.

21. The composition of claim 1, wherein the reactive monomer mixture comprises the tricyclo[$5.2.1.0^{2,6}$]decanedimethanol di(meth)acrylate cross-linking agent in an amount between 1 and 20 weight percent.

22. The composition of claim 11, having a water content of between about 1 weight percent and about 10 weight percent.

23. The composition of claim 11, having a water content of between about 1 weight percent and about 8 weight percent.

24. The composition of claim 12, wherein the composition has a refractive index of at least 1.48 and an Abbe number of at least 50.

25. The composition of claim 12, wherein the composition has a refractive index of at least 1.50 and an Abbe number of at least 50.

* * * * *